US010828399B2

(12) United States Patent
Burdick et al.

(10) Patent No.: US 10,828,399 B2
(45) Date of Patent: Nov. 10, 2020

(54) THREE DIMENSIONAL PRINTING OF SUPRAMOLECULAR (HYDRO)GELS

(71) Applicant: The Trustees of the University of Pennsylvania, Philadelphia, PA (US)

(72) Inventors: Jason Alan Burdick, Philadelphia, PA (US); Chris Highley, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 494 days.

(21) Appl. No.: 15/079,257

(22) Filed: Mar. 24, 2016

(65) Prior Publication Data

US 2016/0279868 A1    Sep. 29, 2016

Related U.S. Application Data

(60) Provisional application No. 62/139,076, filed on Mar. 27, 2015.

(51) Int. Cl.
*A61L 27/54* (2006.01)
*C09D 11/14* (2006.01)
(Continued)

(52) U.S. Cl.
CPC .............. *A61L 27/54* (2013.01); *A61L 27/20* (2013.01); *A61L 27/38* (2013.01); *A61L 27/52* (2013.01); *B29C 64/106* (2017.08); *B29C 64/112* (2017.08); *C09D 11/101* (2013.01); *C09D 11/14* (2013.01); *C09D 11/38* (2013.01); *B29K 2105/0061* (2013.01); *B29K 2995/0056* (2013.01); *B33Y 10/00* (2014.12); *B33Y 70/00* (2014.12)

(58) Field of Classification Search
CPC ... B29C 64/106; B29C 64/112; B29C 64/124; B29C 64/307; B29C 64/321; B29C 64/343; A61L 27/52; A61L 27/20; A61L 27/38; A61L 27/54; B29K 2105/0061; B29K 2995/0056; C08L 5/08; C09D 11/101; C09D 11/14; C09D 11/38; B33Y 10/00; B33Y 70/00
See application file for complete search history.

(56) References Cited

U.S. PATENT DOCUMENTS 7,191,456 B2    3/2007  Guo et al.
7,520,091 B2    4/2009  Friedman
(Continued)

FOREIGN PATENT DOCUMENTS

WO    WO 2014/028209 A1    2/2014

OTHER PUBLICATIONS

Roddell et al., "Rational Design of Network Properties in Guest-Host Assembled and Shear-Thinning Hyaluronic Acid Hydrogels", Biomacromolecules, Sep. 2013, 14, 4125-4134 (Year: 2013).*
(Continued)

*Primary Examiner* — Philip C Tucker
*Assistant Examiner* — Jimmy R Smith, Jr.
(74) *Attorney, Agent, or Firm* — BakerHostetler

(57) ABSTRACT

The present disclosure is directed to methods of printing 3-D structures using supramolecular gels, and the structures that result therefrom.

21 Claims, 30 Drawing Sheets
(29 of 30 Drawing Sheet(s) Filed in Color)

(51) Int. Cl.
| | |
|---|---|
| A61L 27/20 | (2006.01) |
| A61L 27/52 | (2006.01) |
| A61L 27/38 | (2006.01) |
| B29C 64/112 | (2017.01) |
| B29C 64/106 | (2017.01) |
| B33Y 10/00 | (2015.01) |
| B33Y 70/00 | (2020.01) |
| C09D 11/38 | (2014.01) |
| C09D 11/101 | (2014.01) |
| B29K 105/00 | (2006.01) |

(56) References Cited

U.S. PATENT DOCUMENTS

| | | | | |
|---|---|---|---|---|
| 2011/0212501 A1* | 9/2011 | Yoo | ........................ | A61L 27/54 435/174 |
| 2012/0089238 A1* | 4/2012 | Kang | .................... | B29C 64/112 623/23.72 |
| 2016/0167312 A1* | 6/2016 | Feinberg | ................ | B33Y 10/00 264/239 |
| 2018/0030192 A1* | 2/2018 | Kai | ........................ | A61L 27/52 |

OTHER PUBLICATIONS

Kesti, et al., "A versatile bioink for three-dimensional printing of cellular scaffolds based on thermally and photo-triggered tandem gelation", Acta Biomaterial., available online Sep. 23, 2014, 162-172.*
Fakhari and Berkland, "Applications and Emerging Trends of Hyaluronic Acid in Tissue Engineering, as a Dermal Filler, and in Osteoarthritis Treatment", Acta Biomaterial., Jul. 2013, 9(7), 7081-7092.*
Aguado et al., "Improving Viability of Stem Cells During Syringe Needle Flow Through the Design of Hydrogel Cell Carriers", Tissue Engineering, Apr. 2012, Part A, 18, 806-815.
Anderson et al., "A Combinatorial Library of Photocrosslinkable and Degradable Materials", Adv. Materials, Sep. 2006, vol. 18, 2614-2618.
Appel et al., "Supramolecular polymeric hydrogels", Chem. Soc. Rev., Aug. 2012, 41, 6195-6214.
Bakarich et al., "Extrusion printing of ionic-covalent entanglement hydrogels with high toughness", Journal of Materials Chemistry B, Aug. 2013, 1, 4939-4946.
Boland et al., "Drop-on-demand printing of cells and materials for designer tissue constructs", Materials Science & Engineering, Apr. 2007, 27, 372-376.
Burdick et al., "Hyaluronic Acid Hydrogels for Biomedical Applications", Advanced Materials, Mar. 2011, 23, H41-H56.
Choi et al., "Microfluidic scaffolds for tissue engineering", Nature Materials, Nov. 2007, 6, 908-915.
Compton et al., "3D-Printing of Lightweight Cellular Composites", Advanced Materials, Jun. 2014, 26, 5930-5935.
Cui et al., "Direct Human Cartilage Repair Using Three-Dimensional Bioprinting Technology", Tissue Engineering, Jun. 2012, Part A, 18, 1304-1312.
Cushing et al., "Hydrogel Cell Cultures", Science, May 2007, 316, 1133-1134.
Derby, "Printing and Phototyping of Tissues and Scaffolds", Science, Nov. 2012, 338, 921-926.
Golden et al., "Fabrication of microfluidic hydrogels using gelatin as a sacrificial element", Lab on a Chip, Jun. 2007, 7, 720-725.
Guvendiren et al., "Engineering synthetic hydrogel microenvironments to instruct stem cells", Current Opinion in Biotechnology, Oct. 2013, 24, 841-846.
Guvendiren et al., "Shear-thinning (hydro)gels for biomedical applications", Soft Matter, 2012, 8, 260-272.
Highley et al., "Direct 3D Printing of Shear-Thinning Hydrogels into Self-Healing Hydrogels", Advanced Materials, Jul. 2015, 87, 5075-5079.

Highley et al., "Recent Advances in Hyaluronic Acid Hydrogels for Biomedical Applications", Current Opinion in Biotechnology, Aug. 2016, 40, 35-40.
Hockaday et al., "Rapid 3D printing of anatomically accurate and mechanically heterogeneous aortic valve hydrogel scaffolds", Biofabrication, Sep. 2012, 4, 035005, 12 pages.
Ifkovits et al., "Review: Photopolymerizable and Degradable Biomaterials for Tissue Engineering Applications", Tissue Engineering, Oct. 2007, 13, 2369-2385.
Kolesky et al., "3D Bioprinting of Vascularized, Heterogeneous Cell-Laden Tissue Constructs", Advanced Materials, Feb. 2014, 26, 3124-3130.
Kong et al., "3D Printed Quantum Dot Light-Emitting Diodes", Nano Letters, Oct. 2014, 14, 7017-7023.
Ladd et al., "3D Printing of Free Standing Liquid Metal Microstructures", Advanced Materials, Jul. 2013, 25, 5081-5085.
Li et al., "Rapid Formation of a Supramolecular Polypeptide-DNA Hydrogel for In Situ Three-Dimensional Multilayer Bioprinting", Angewandte Chemie International Edition, Mar. 2015, 54, 3957-3961.
Lu et al., "Injectable Shear-Thinning Hydrogels Engineered with a Self-Assembling Dock-and-Lock Mechanism", Biomaterials, Mar. 2012, 33, 2145-2133.
Lu et al., "Secondary Photocrosslinking of Injectable Shear-Thinning Dock-and-Lock Hydrogels", Advanced Healthcare Materials, Jul. 2013, 2, 1028-1036.
Malda et al., "25$^{th}$ Anniversary Article: Engineering Hydrogels for Biofabrication", Advanced Materials, Aug. 2013, 25, 5011-5027.
Miller et al., "Rapid casting of patterned vascular networks for perfusable engineered three-dimensional tissues", Nature Materials, Jul. 2012, 11, 768-774.
Mironov et al., "Organ printing: computer-aided jet-based 3D tissue engineering", Trends in Biotechnology, Apr. 2003, 21, 157-161.
Murphy et al., "3D bioprinting of tissues and organs", Nature Biotechnology, Aug. 2014, 32, 773-785.
Nguyen et al., "Photopolymerizable hydrogels for tissue engineering applications", Biomaterials, Nov. 2002, 23, 4307-4314.
Pataky et al., "Microdrop Printing of Hydrogel Bioinks into 3D Tissue-Like Geometries", Advanced Materials, Jan. 2012, 24, 391-396.
Pati et al., "Printing three-dimensional tissue analogues with decellularized extracellular matrix bioink", Nature Communications, Jun. 2014, 5, 3935, 11 pages.
Radisic et al., "Medium perfusion enables engineering of compact and contractile tissue", Am. J. Physiol. Heart Circ. Physiol., Feb. 2004, 286, H507-H516.
Roddell et al., "Rational Design of Network Properties in Guest-Host Assembled and Shear-Thinning Hyaluronic Acid Hydrogels", Biomacromolecules, Sep. 2013, 14, 4125-4134.
Roddell et al., "Shear-Thinning Supramolecular Hydrogels with Secondary Autonomous Covalent Crosslinking to Modulate Viscoelastic Properties In Vivo", Advanced Functional Materials, Oct. 2015, 25, 636-644.
Rutz et al., "A Multimaterial Bioink Method for 3D Printing Tunable, Cell-Compatible Hydrogels", Advanced Materials, Jan. 2015, 27, 1607-1614.
Sahoo et al., "Hydrolytically Degradable Hyaluronic Acid Hydrogels with Controlled Temporal Structures", Biomacromolecules, Apr. 2008, 9, 1088-1092.
Seiffert et al., "Physical chemistry of supramolecular polymer networks", Chem. Soc. Rev., 2012, 41, 909-930.
Skardal et al., "Photocrosslinkable Hyaluronan-Gelatin Hydrogels for Two-Step Bioprinting", Tissue Engineering, Aug. 2010, Part A, 16, 2675-2685.
Smeds et al., "Photocrosslinkable polysaccharides for in situ hydrogel formation", Biomed. Mater. Res., Nov. 2000, 54, 115-121.
Tan et al., "Electrospinning of photocrosslinked and degradable fibrous scaffolds", J. Biomed Matl. Res., Dec. 2008, vol. 87(4), 1034-1043.
Tölle et al., "Emulsifier-Free Graphene Dispersions with High Graphene Content for Printed Electronics and Freestanding Graphene Films", Advanced Functional Materials, Jan. 2012, 22, 1136-1144.

(56) References Cited

OTHER PUBLICATIONS

Visser et al., "Biofabrication of multi-material anatomically shaped tissue constructs", Biofabrication, Sep. 2013, 5, 035007, 9 pages.
Wang et al., "Generation of Three-Dimensional Hepatocyte/Gelatin Structures with Rapid Prototyping System", Tissue Engineering, Jan. 2006, 12, 83-90.
Wu et al., "Omnidirectional Printing of 3D Microvascular Networks", Advanced Healthcare Materials, Mar. 2011, 23, H178-H183.
Wu et al., "Solid free-form fabrication of drug delivery devices", Journal of Controlled Release, Jun. 1996, 40, 77-87.
Xu et al., "Complex heterogeneous tissue constructs containing multiple cell types prepared by inkjet printing technology", Biomaterials, Jan. 2013, 34, 130-139.
Yan et al., "Injectable Solid Peptide Hydrogel as a Cell Carrier: Effects of Shear Flow on Hydrogels and Cell Payload", Langmuir, Apr. 2012, 28, 6076-6087.

\* cited by examiner

A
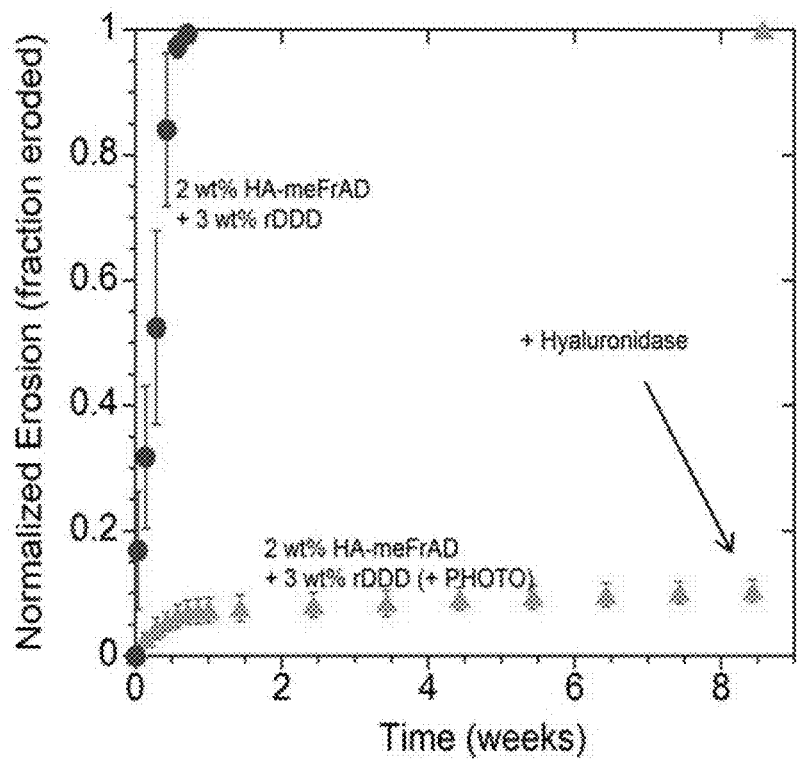
B
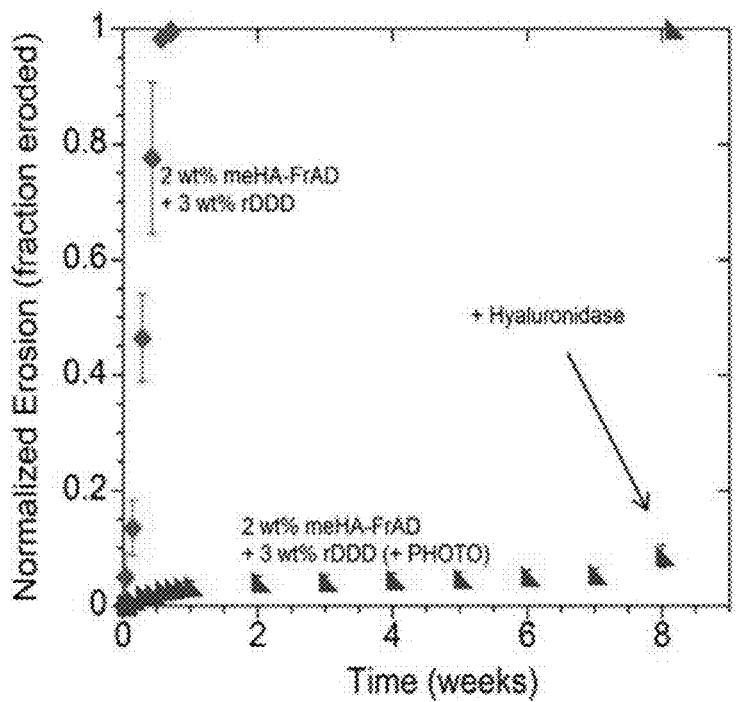
FIG. 9(A/B)

A
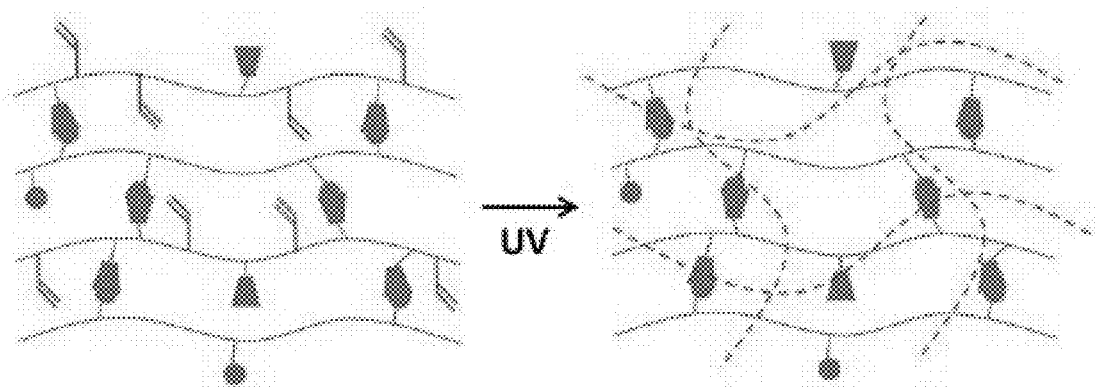
(B
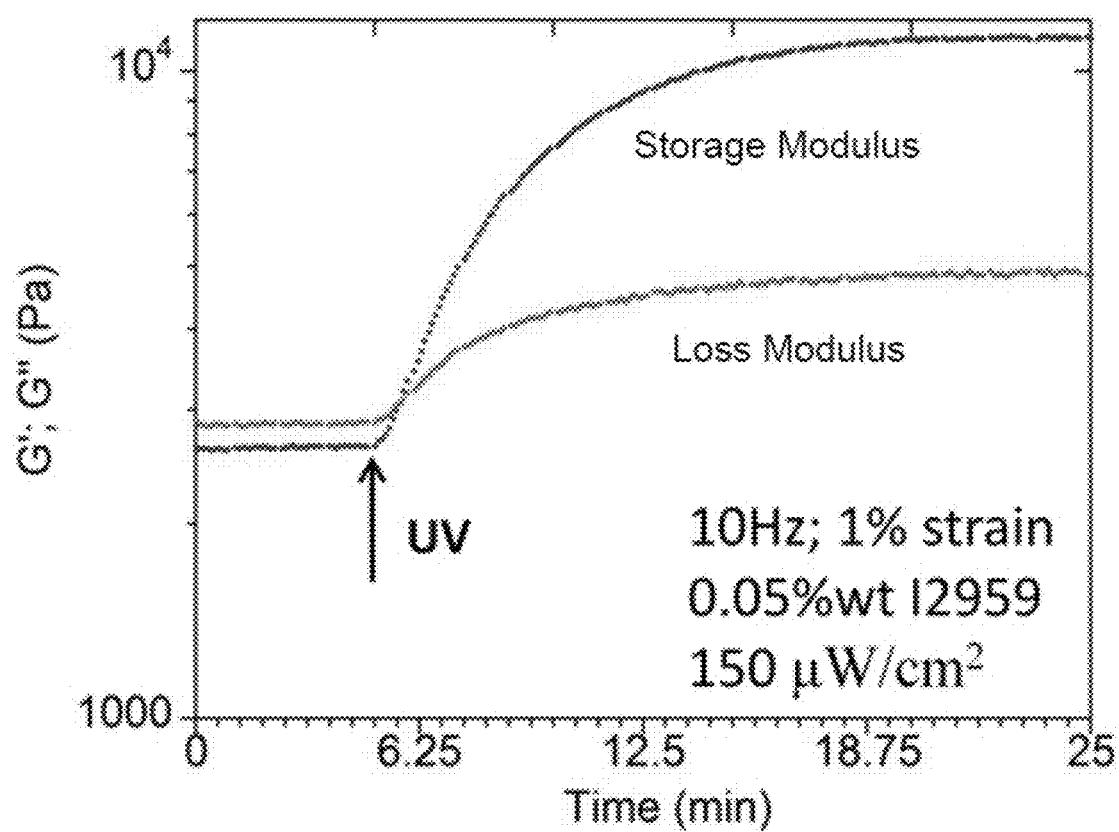
FIG. 10(A/B)

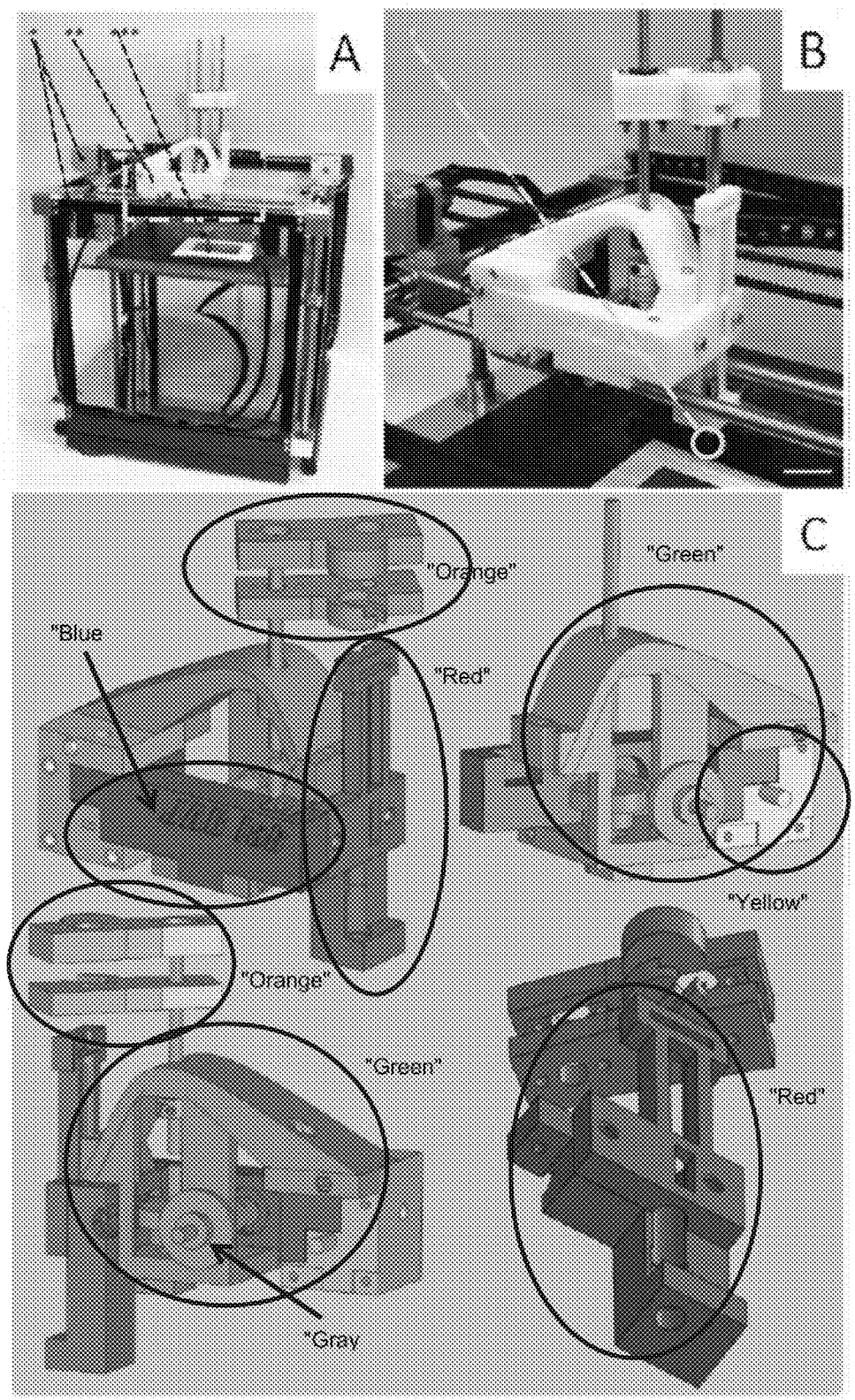
FIG. 11(A-C)

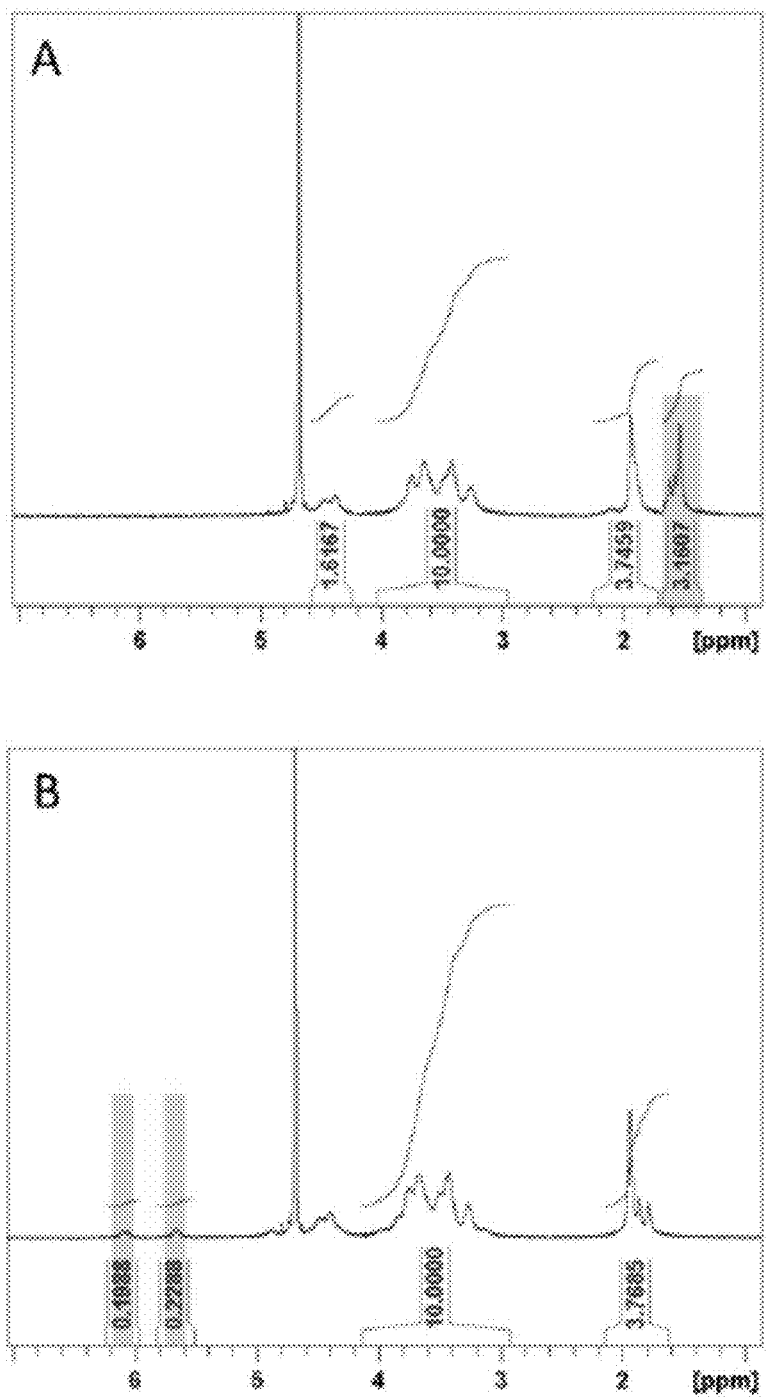
FIG. 12(A/B)

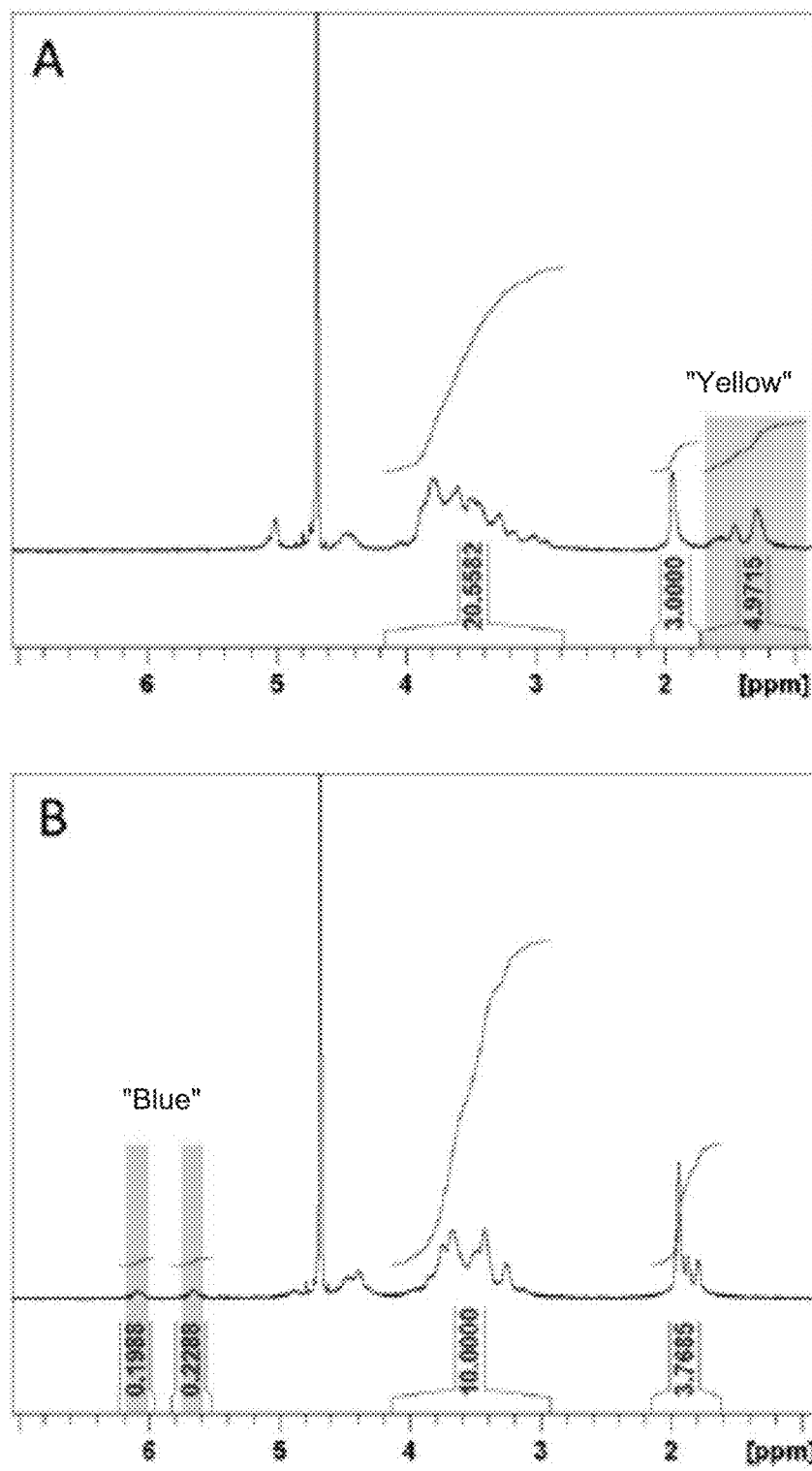
FIG. 13(A/B)

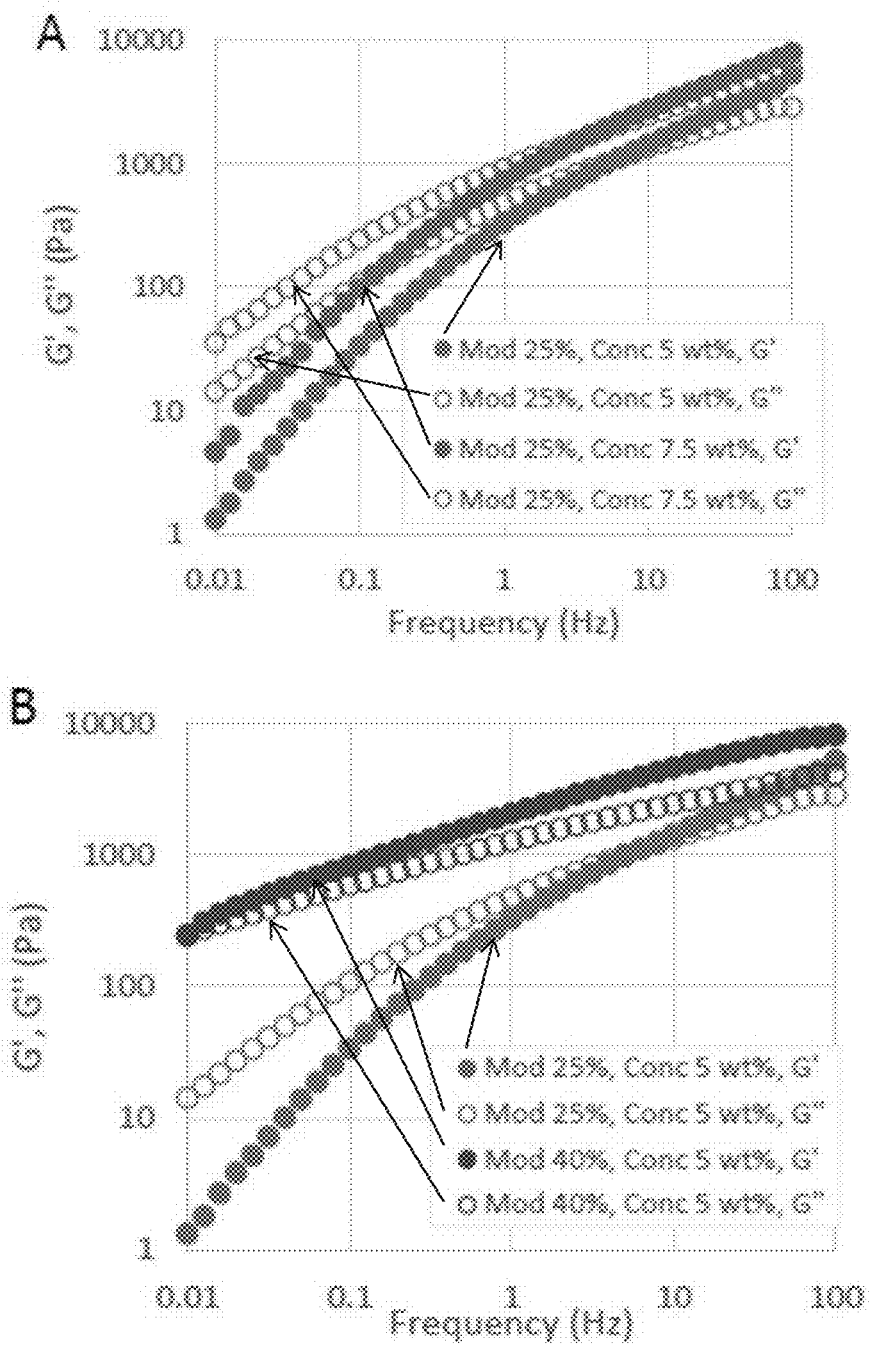
FIG. 15(A/B)

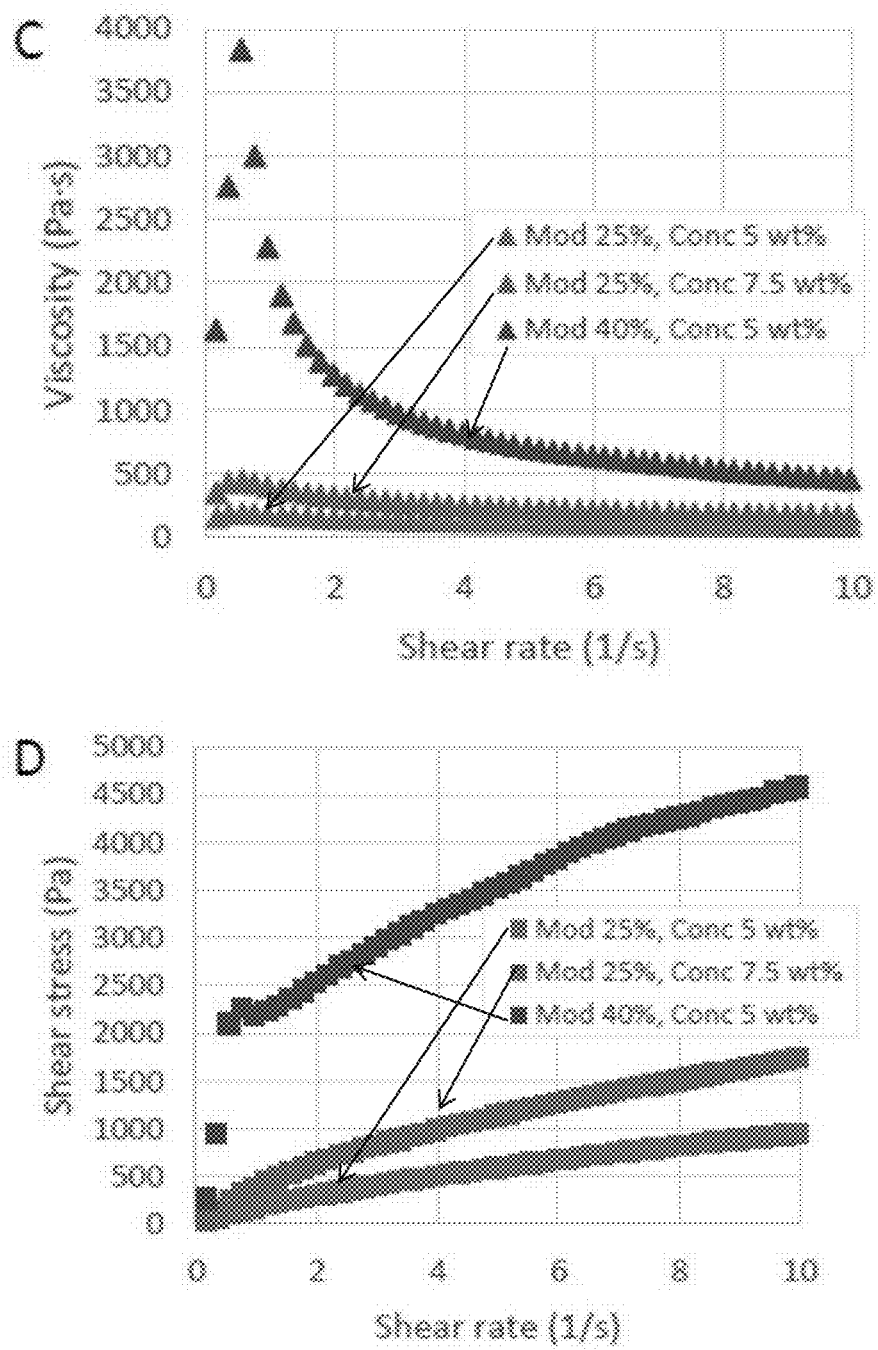
FIG. 15(C/D)

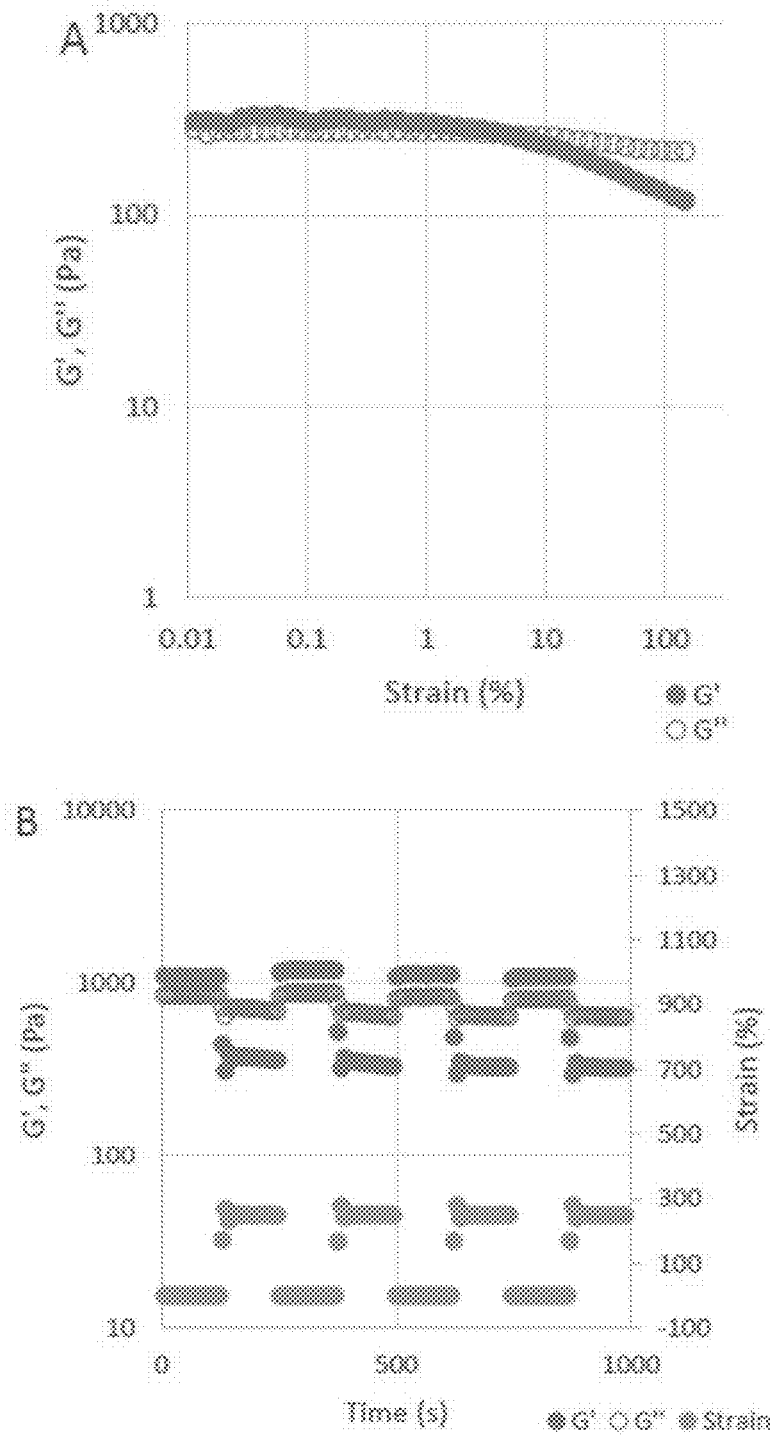
FIG 16(A/B)

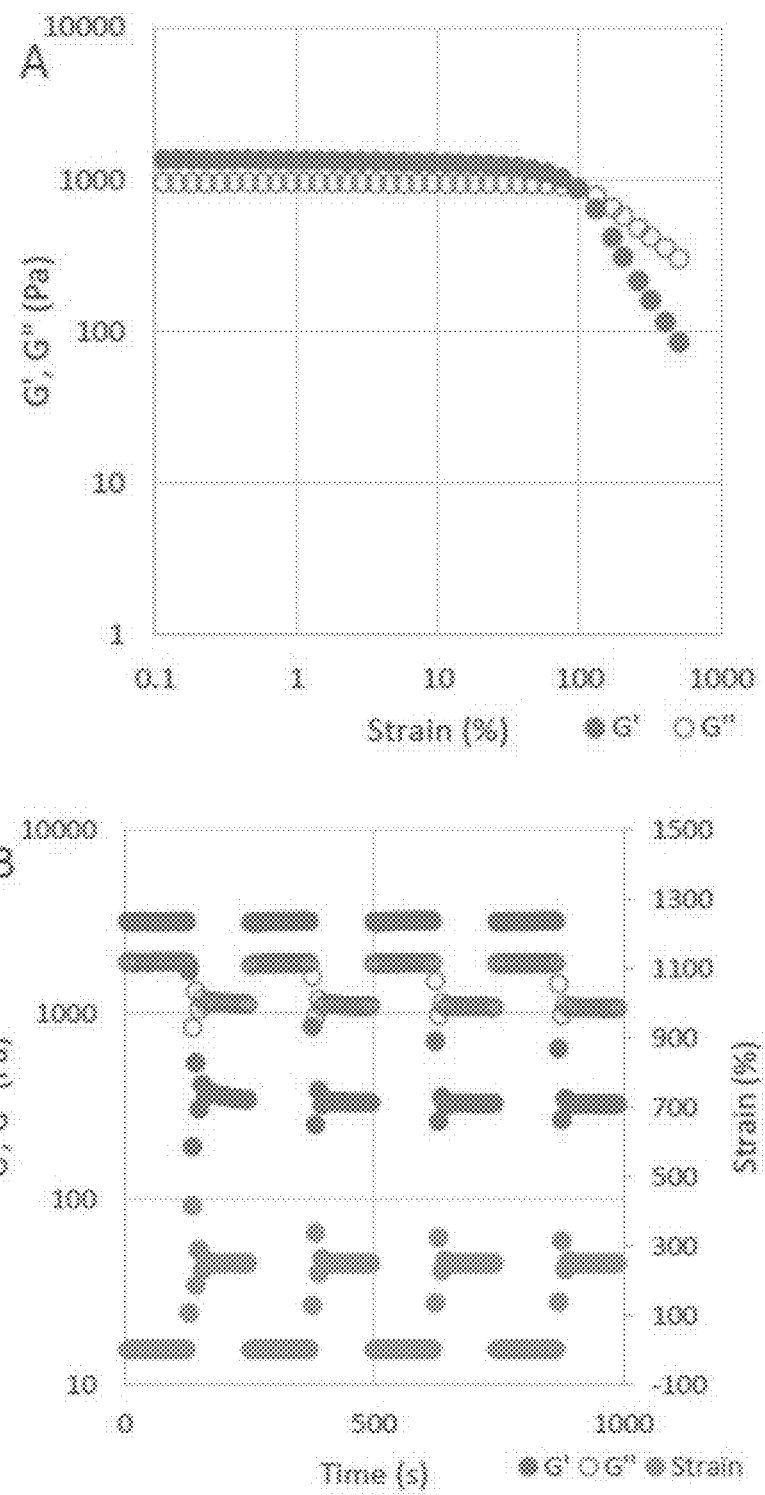
FIG. 17(A/B)

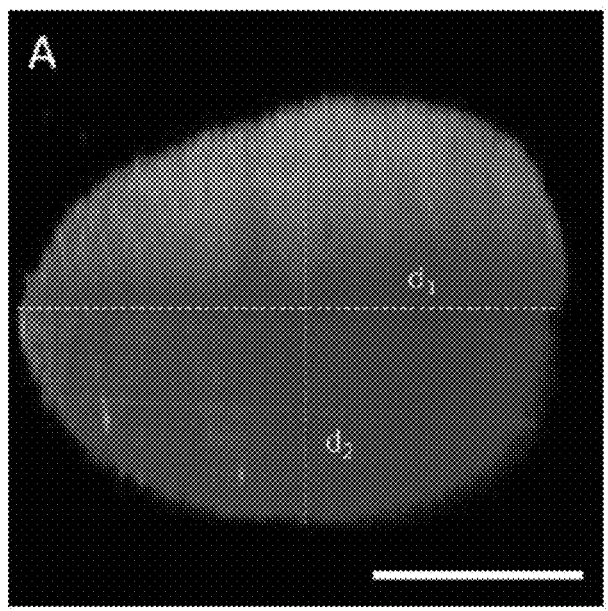
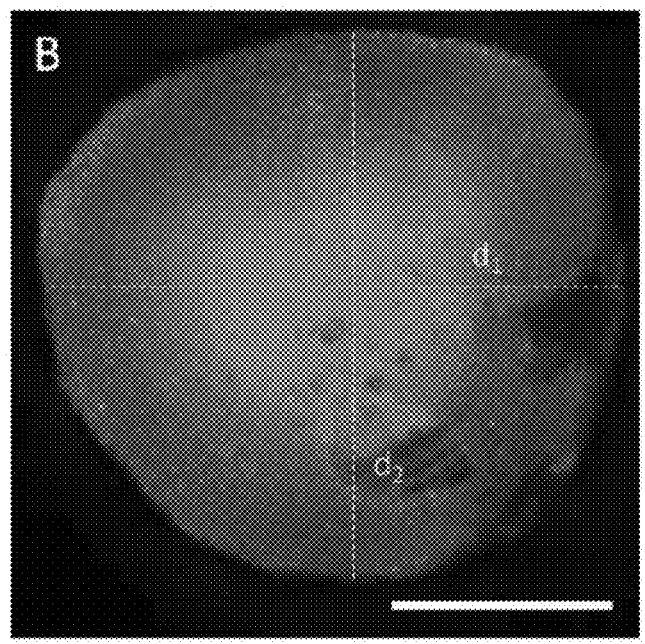
| | $d_1$ (μm) | $d_2$ (μm) | $d_2/d_1$ |
|---|---|---|---|
| A | 1291 | 980 | 0.76 |
| B | 1327 | 1305 | 0.98 |
FIG. 18(A/B)

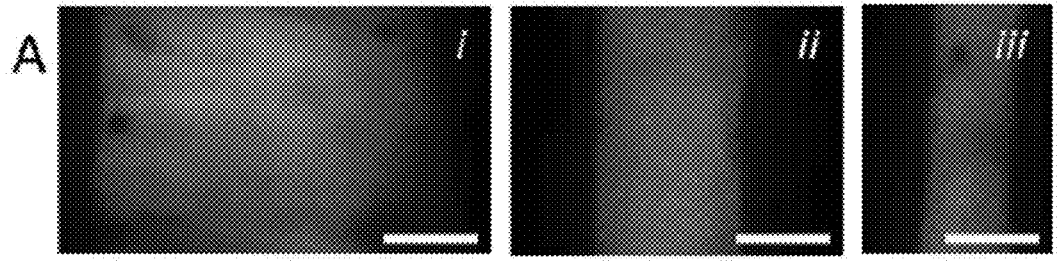
| | $d_{ave}$ (μm) | vol (nL)/mm | rate, flow (relative) |
|---|---|---|---|
| i | 761.9 ± 28.8 | 455 ± 0.7 | 12 |
| ii | 331.7 ± 11.7 | 86.4 ± 0.1 | 1 |
| iii | 222.6 ± 29.7 | 38.9 ± 0.7 | 0.25 |
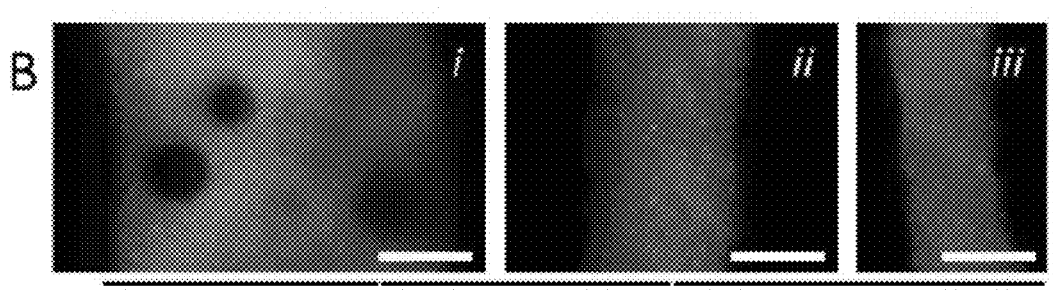
| | $d_{ave}$ (μm) | vol (nL)/mm | rate, translation (relative) |
|---|---|---|---|
| i | 759.2 ± 30.8 | 452 ± 0.7 | 0.5 |
| ii | 336.3 ± 15.4 | 88.9 ± 0.2 | 1 |
| iii | 224.0 ± 25.3 | 39.4 ± 0.5 | 4 |
FIG. 19(A/B)

|  | $d_1$ (μm) | $d_2$ (μm) |
|---|---|---|
| Day 0 | 187 | 843 |
| Day 3 | 189 | 884 |
| Day 7 | 185 | 888 |

FIG. 20 (cont.)

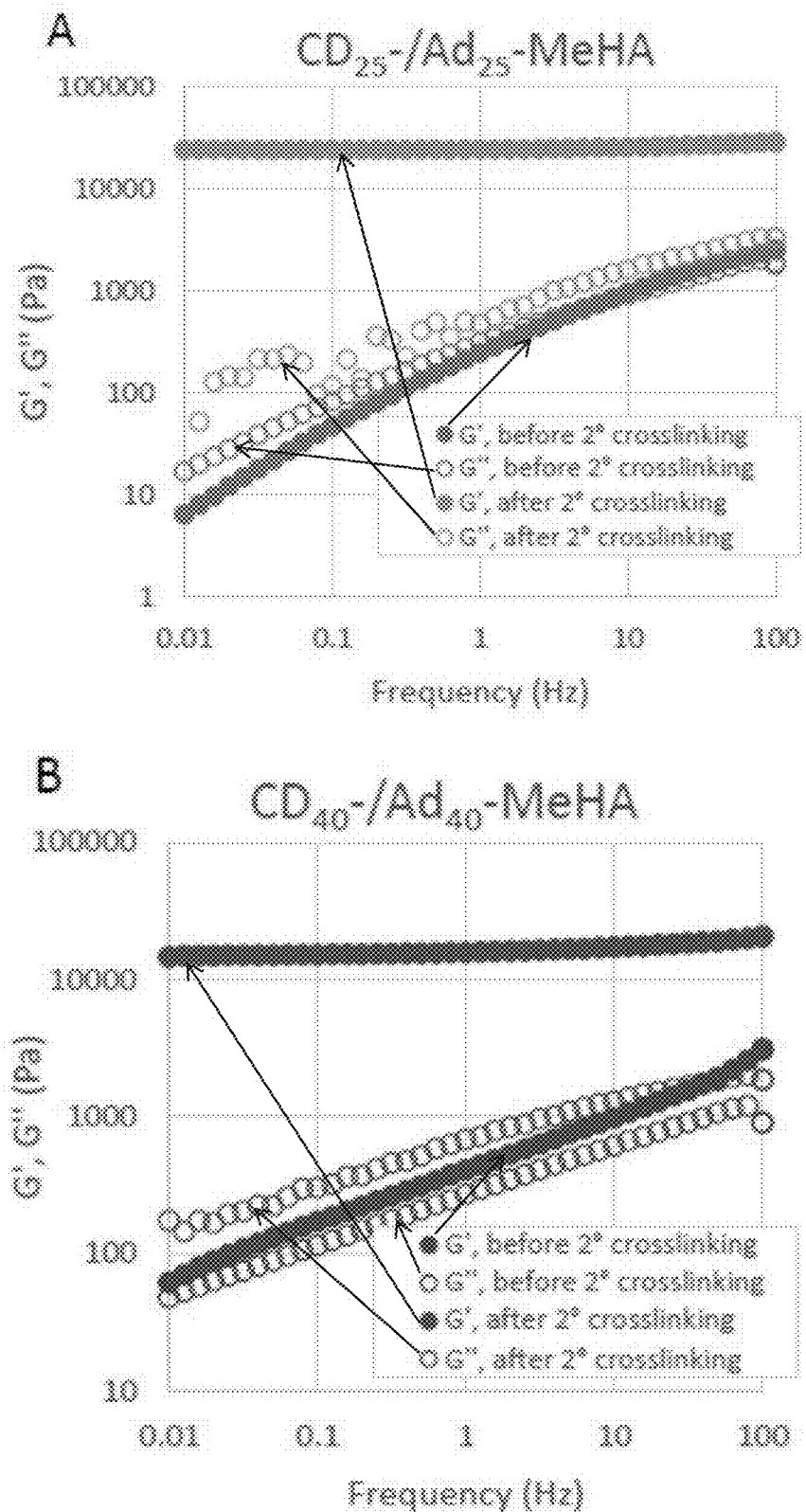
FIG. 22(A/B)

THREE DIMENSIONAL PRINTING OF SUPRAMOLECULAR (HYDRO)GELS

CROSS REFERENCE TO RELATED APPLICATIONS

This application claims the benefit of the priority of U.S. Provisional Patent Application No. 62/139,076, filed Mar. 27, 2015, which is incorporated by reference.

TECHNICAL FIELD

The present disclosure is directed to compositions and methods directed to three-dimensional printing using gels, especially supramolecular (hydro)gels.

BACKGROUND

Current three dimensional printing (3-DP) technologies which deposit material to build up a structure—for example by ink jetting or extrusion of material from a print head—build constructs one layer at a time. This limits the structuring of material into three-dimensional (3-D) space to depend on the existence of a previously deposited support or on a material's ability to support its own structure, as in the case of sugar-based lattices, for example. Another limitation related to the materials used in 3-DP deposition techniques is that a printer is not able to return to an arbitrary point in 3-D space to deposit additional material.

Given the increased attention and need to produce complex, three-dimensional structures for applications including medical, biomedical, and electronics, there is a need for improved methods for producing such structures.

SUMMARY

The present disclosure is directed to methods of printing 3-D structures using supramolecular (hydro)gels, and the structures which result therefrom. These supramolecular (hydro)gels are shear-thinning (which allows for their extrusion through needles) and rapidly self-healing (which allows the disrupted bonds to form again). Depending on the supramolecular chemistry used, properties of these materials can also be varied, including mechanical/rheological properties and dynamic properties such as kinetics of bond formation, or colloidal associations and/or dissociations. Methods employing supramolecular (hydro)gels are preferred.

Various embodiments of the present disclosure provide methods of manufacturing three-dimensional (3-D) structures, each method comprising delivering a volume of a first ink material into a volume of at least one template material, thereby forming a two- or three dimensional patterned volume of the first ink material within the volume of the at least one template material, the at least one template material comprising a self-healing supramolecular (hydro)gel capable of maintaining the shape and dimensional stability of the two- or three-dimensional pattern of the delivered volume of the first ink material.

In other embodiments, the method may be repeated one or more times, for example, providing methods further comprising delivering a volume of a second ink and optionally subsequent volumes of subsequent ink materials (a) into the volume of the at least one template material; (b) into a volume of at least one of an earlier delivered ink material, or (c) into both the volume of the at least one template material and a volume of at least one of the earlier delivered ink materials, thereby forming a two- or three dimensional patterned volume of the second and optionally subsequent ink material, where the at least one template material comprises a self-healing supramolecular (hydro)gel capable of maintaining the shape and dimensional stability of the two- or three-dimensional pattern of the delivered volumes of the ink materials. In certain embodiments the first, second, or optionally subsequent ink materials each comprise a supramolecular (hydro)gel that is compositionally different from the supramolecular (hydro)gel of at least one of the template materials. In other embodiments, each of the first, second, or optionally subsequent ink materials are compositionally the same or different from the other ink materials.

Typically, but not necessarily, at least one of the ink materials is delivered by injection into the respective volume of the preceding ink or template material. In these cases, the dimensions of the injection device, for example a needle, cannula, catheter, or other tubing, may define the dimensions of the injected volume(s). Similarly, it is useful, though not necessary, that one or more of these inks comprise a shear thinning material that sets to a solid or semi-solid upon delivery into the respective volume of the preceding ink or template material.

In some embodiments, depending on the nature of the final article prepared by such methods, at least one of the ink materials, the template material, or any combination thereof independently comprise a pharmaceutically active drug or neutraceutical; a population of cells; a peptide or peptide derivative; one or more types of nanoparticles or quantum dots; a fluorescent or phosphorescent material; a magnetic material; or combination thereof.

In some embodiments, at least one of the ink materials, the template material, or any combination thereof independently comprise a settable, shear-thinning supramolecular (hydro)gel comprising a polymer network, said polymer network comprising non-covalent crosslinks and at least one set of chemical moieties being capable of participating in at least one chemical covalent cross-linking reaction. Further embodiments provide that one or more of these crosslinking pairs are activated, or triggered, to crosslink. Method and compositions providing for these methods are described herein.

The inventive methods also comprise those methods further comprising selectively removing at least a portion of any one of the at least one ink materials, the template material, or any combination thereof. This selective removal can be done before, after, or in the absence of crosslinking, depending on the nature of the desired product and/or the nature of the inks and template materials. Such selective removal, depending on its nature, can result in a structure comprising the template material having channels, tunnels, internal cavities or voids. In some cases, the channels, tunnels, internal cavities, or voids may be interconnected in one, two, or three dimensions within the structure.

In other embodiments, the methods further comprise selectively removing at least a portion of the template material, resulting in a shaped structure comprising at least one of the ink materials. In other embodiments, the methods further comprise selecting at least a portion of one or more inks and at least a portion of the template material, thereby providing a shaped structure containing internal structures.

The disclosure also contemplates those articles or structures prepared by the inventive methods, either as intermediates or final products. Such articles are described herein.

BRIEF DESCRIPTION OF THE DRAWINGS

The application file contains at least one drawing executed in color. Copies of this patent or patent application publication with color drawings will be provided by the Office upon request and payment of the necessary fee.

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 2 exemplifies the use of any bond of this type, where the bonding stabilizing the material structure can be disrupted and easily reformed. Section i) shows the supramolecular bonding between Ad and CD moieties on a polymer backbone. They have a strong tendency to remain associated. Section ii) application of a stimulus (e.g., heat or shear, in the case of Ad/CD) causes molecules to dissociate. iii) A supramolecular gel network illustrated, where, upon the application of a stimulus, bonds stabilizing the gel dissociate and material solubilizes, behaving as a solution instead of a gel. Removal of the stimulus would enable reformation of the (hydro)gel.

FIG. 5 shows a cartoon illustrating the use of a previously printed ink as the support for further inks. This allows layered deposition from a single point (for example). i) A needle with a first ink (e.g., red) can be positioned at a point in 3D space within a support gel and the ink extruded. ii) A needle with a second ink (e.g., green) is positioned at the same point in 3D, and iii) the second ink is extruded. In this manner, a third ink (e.g., blue) could be deposited, and so on.

FIG. 6 shows potential chemistry to be used where either adamantane or β-cyclodextrin modified HA also contains a methacrylate group that can undergo a radical polymerization to covalently crosslink the polymers (again, these are model chemistries which might be substituted with other supramolecularly-covalently-interacting moieties). FIG. 7 shows i) that the methacrylation of the supramolecular support (or ink) does not affect the printing process. Here, a methacrylated support material is used to receive a printed ink. The bottom image shows a series of bifurcating and rejoining channels printed into such a support material. ii) Exposure to UV light (in the presence of a photoinitiator molecule) allows crosslinking of the methacrylates within the support region (crosslinking indicated by dashed blue lines). The bottom image shows a zoomed-out view of the channels printed into the methacrylated support during UV crosslinking. iii) An applied stimulus of heat or shear will subsequently disrupt supramolecular bonding, allowing removal of material that is not stabilized via secondary crosslinking. This allows, for example, printed material to be removed, leaving channels and voids within the support (hydro)gel (conversely, printed materials can be stabilized and the supports around them removed). The bottom image shows the purged channels, no longer containing the printed material, through which liquid could flow.

FIG. 8 shows i) an example where an ink, which has been modified to have the secondary methacrylates, in addition to supramolecular chemistries, is printed into a support (hydro)gel which does not have the ability to form covalent bonds and could thus be removed by disruption of its supramolecular bonds. ii) UV-initiated crosslinking induces stabilization of the printed material. iii) Supramolecular bonds can be disrupted, allowing the removal of the support (hydro)gel, while the printed material remains in place. iv) Secondary crosslinking enabled the printing of a complex 3D structure, here four-sided pyramid, which was subsequently released from its support material. The view of the structure is from directly above its top vertex as it rests on the base formed by the printed material joining the other three vertices.

FIGS. 9A/B illustrate the improvements in bioerosion available in photopolymerizing to crosslink an exemplary acrylate-modified a DnL (hydro)gel.

FIG. 10A shows a schematic of the chemical cross-linking of exemplary methacrylate vinyl groups upon photopolymerization stabilized the (hydro)gel network. FIG. 10B shows the stability of these crosslinked (hydro)gels. The (hydro)gels were formed by mixing of Ad-HA and CD-MeHA components at 7.5 wt % where CD and Ad functionality are in a 1:1 ratio. The solvent used for preparation was PBS containing 4-(2-hydroxyethoxy)phenyl-(2-hydroxy-2-propyl)ketone (Irgacure 2959, 12959) at 0.05 wt % as a radical initiator Throughout photopolymerization (initiated with ultraviolet light, 365 nm, 150 $\mu W/cm^2$), an increase in moduli was observed and shear-thinning behavior subsequently found to be arrested. A frequency sweep confirmed the secondary covalent cross-linking results in a solid (hydro)gel.

FIG. 11 shows an illustrative example of a 3D printer as described herein. FIG. 11A is 3D printer with custom syringe extruder attached (dashed box). The single star points to two of the six stepper motors. The double star points to the mounting point of the custom syringe extruder to the included thermoplastic extruder. The triple star points to the print platform. FIG. 11B is a close up of the syringe extruder mounted on the 3D printer with a starred circle indicating location of the syringe needle. The scalebar is about 2 cm. FIG. 11C are images of a CAD model for custom syringe extruder. The colored components are the individual parts that were custom built and printed to assemble the syringe extruder, and the grey components represent gears, shafts, and the lead screw, which were among parts that also included washers, screws, and bearings, that were purchased from commercial vendors.

FIGS. 12A-C are $^1$H-NMR spectra of (A) Ad-HA (degree of mod ~0.25), (B) the MeHA used in the synthesis of Ad-MeHA, and (C) Ad-MeHA (degree of mod ~0.4).

FIGS. 13A-C are $^1$H-NMR spectra of (A) CD-HA (degree of mod ~0.4), (B) the MeHA used in the synthesis of CD-MeHA, C) and CD-MeHA (degree of mod also ~0.4).

FIGS. 15A-D illustrate the rheological characterization of CD-HA/Ad-HA (hydro)gels with guest:host ratio of 1:1 and variable concentrations (5 or 7.5 wt/v %) and degree of modification (25 or 40%).

FIGS. 16A/B show the rheological characteristics of a representative ink gel sample (25% modified Ad-HA mixed with 25% modified CD-HA, such that Ad and CD are present at a 1:1 stoichiometric ratio, 5 wt/v % polymer concentration).

FIGS. 17A-C show the rheological characteristics of a representative support gel sample (40% modified Ad-HA mixed with 40% modified CD-HA, such that Ad and CD are present at a 1:1 stoichiometric ratio, 4 wt/v % polymer concentration).

FIGS. 18A/B are images of filaments. FIG. 18A is an image of the filament printed into a support gel, stabilized by secondary crosslinking, and imaged from the side through a glass window in the sample holder. FIG. 18B is an image of the same filament after removing the gel from the holder, sectioning it with a microtome blade, and imaging from the end. Scalebars: 500 µm. Measurements of the filament dimensions illustrate how the printed filaments appear distorted from the confocal z-stacks. This is likely due to changes in the refractive index within the (hydro)gels relative to water that are not accounted for during imaging.

FIGS. 19A/B are images of filaments of differing widths which were printed from a single 27 gauge needle by adjusting the volume extruded per unit of linear motion. This was done by altering (A) the rate of flow (dimensions given with standard deviation) while keeping the translation speed constant or (B) the translation speed while maintaining a constant rate of flow Filament diameters were quantified for all groups. Compliance and pressure losses within the syringe pump underlie non-linear relationships between rates of extrusion per distance traveled and deposited volumes at high and low flow. Scalebars: 200 µm.

FIGS. 22A/B are graphs showing covalent crosslinking of CD-MeHA and Ad-MeHA (hydro)gels by photopolymerization, leading to increased storage moduli and reduced frequency dependence. (A) Rheological frequency sweep of a 5 wt/v % (hydro)gel of 25%-modified CD-MeHA and Ad-MeHA before and after secondary covalent crosslinking. (B) The same measurements performed for 5 wt/v % (hydro)gels composed of 40%-modified CD-MeHA and Ad-MeHA before and after secondary covalent crosslinking.

DETAILED DESCRIPTION OF ILLUSTRATIVE EMBODIMENTS

Figure 1:
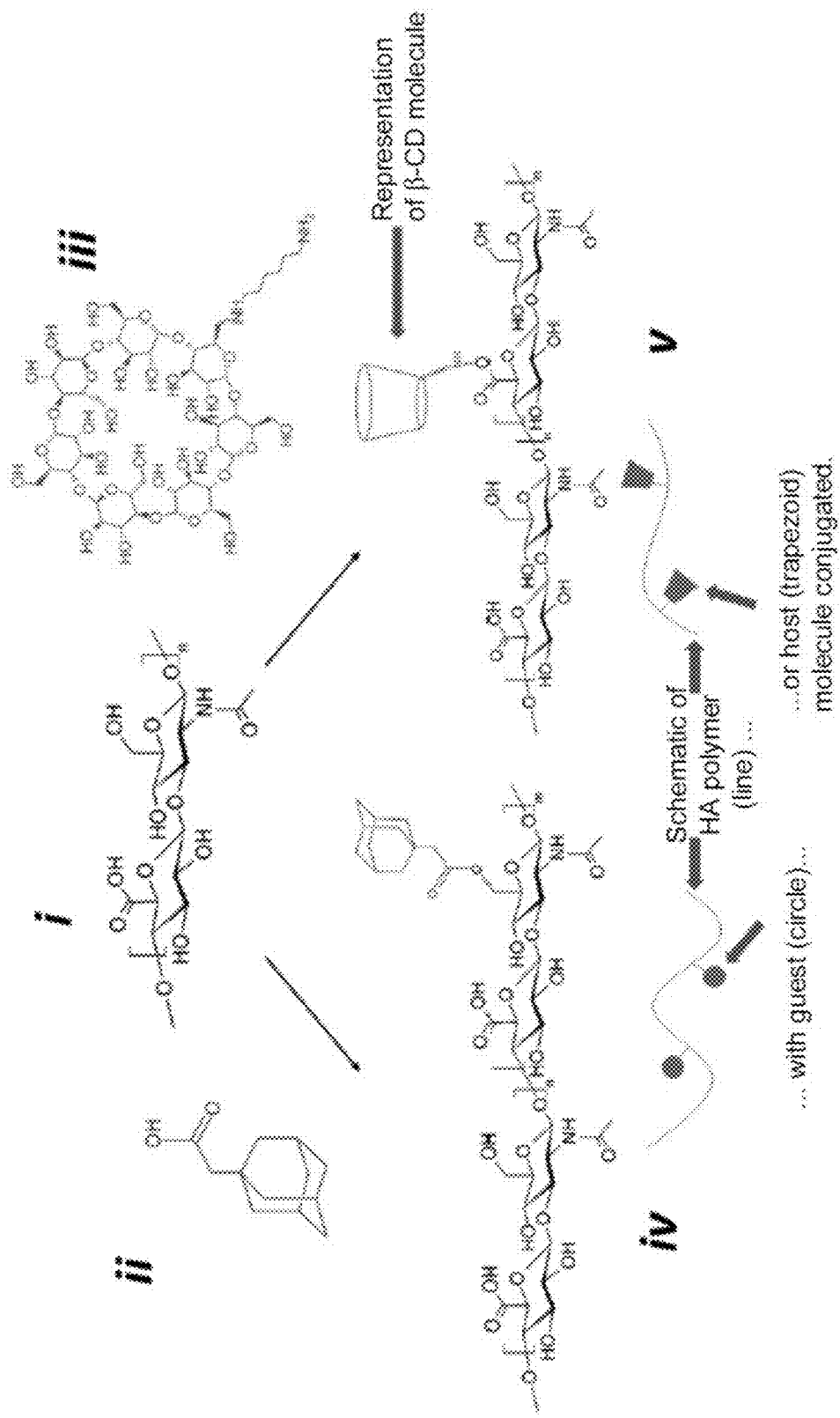
FIG. 1 shows exemplary supramolecular chemistry considered within the scope of the present disclosure: i) shows hyaluronic acid, useful as a backbone polymer; ii) adamantane, a useful guest molecule; iii) Beta-cyclodextrin, a useful host molecule; iv) HA with adamantane conjugated and cartoon representation beneath; and v) HA with a cyclodextrin conjugate, and cartoon representation beneath

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the ability of the template supramolecular (hydro)gel to support ink structures directly injected into the template at any place in 3-D space and the ability to self-heal upon penetration by a cannulus, needle, or other comparable instrument used to deliver the ink within the template. For example, while others are attempting to develop 3-D printing using gel or (hydro)gel technologies, these gels are often built layer-by-layer from a surface and involve crosslinking during the extrusion process and not through shear-thinning and self-healing as described herein.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled the relevant art. However, so as to avoid misunderstanding, the meanings of certain terms will be specifically defined or clarified.

As used herein, the term "gel" is intended to connote that meaning also normally associated with that term—i.e., a material comprising at least one solid matter that is stabilized by bonds giving it a 3-D structure, but whose molecular structure/network can be infiltrated by the molecules of a liquid, where such infiltration may or may not alters the shape or dimensions of the 3-D structure. As used herein, the term "(hydro)gel" is intended to connote that meaning also normally associated with that term—i.e., a three-dimensional hydrophilic network comprising hydrophilic polymers, in which water is the dispersion medium, and are capable of maintaining their structural integrity. (Hydro)gels are highly swollen (they can contain over 99.9% water) natural or synthetic polymers. (Hydro)gels also possess a degree of flexibility very similar to natural tissue, due to their significant water content. Supra-molecular gels or (hydro)gels are a specific class of materials, which are described elsewhere herein. As used herein, the term "(hydro)gel" is intended to connote separate embodiments where one embodiment is a gel and another embodiment is a (hydro)gel.

Similarly, in the present context, the term shear thinning has a meaning normally associated with that term—i.e., an effect where a fluid's viscosity (the measure of a fluid's resistance to flow) decreases with an increasing rate of shear stress. As contemplated herein, such shear-thinning (hydro)gels are composed of two or more polymers or oligomers that are held together in unique structural relationships by forces other than those of full covalent bonds. Non-covalent bonding is critical in the described shear-thinning and self-healing properties. There are four commonly mentioned types of non-covalent interactions: hydrogen bonds, ionic bonds, van der Waals forces, and hydrophobic interactions, each of which is employed in various embodiments of the shear-thinning (hydro)gels contemplated herein.

The present disclosure is directed to a new method of printing 3-D structures using supramolecular (hydro)gels. These gels are preferably shear-thinning (which allows for their extrusion through needles) and rapidly self-healing (which allows the disrupted bonds to form again). Depending on the supramolecular chemistry used, properties of these materials can also be tuned, including mechanical/rheological properties and dynamic properties such as kinetics of bond formation. Some of the materials described in the present disclosure are considered (hydro)gels, and the supramolecular chemistry is described in terms of a guest-host bonding of adamantane (Ad) and β-cyclodextrin (CD) that are linked to polymer chains (see, e.g., FIG. 1). While supramolecular (hydro)gels are preferred embodiments, the present disclosure is not limited to these embodiments and other classes of materials, for example sol-gels and colloidal suspensions, may also be employed.

Figure 2:
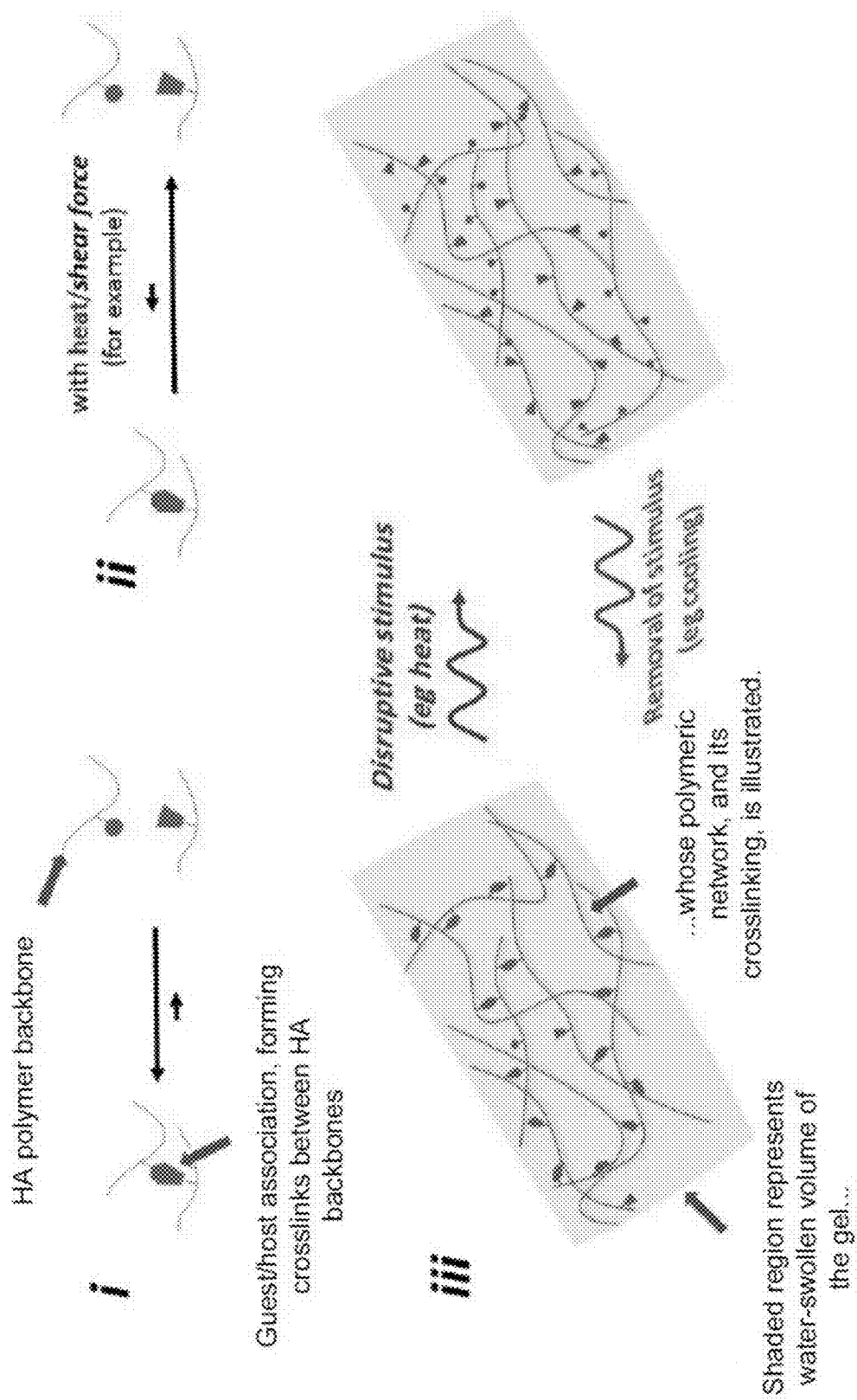
FIG. 2 illustrates one mechanism of supramolecular adamantane/β-cyclodextrin ("Ad/CD") bonding and network stabilization.

In some embodiments, the supramolecular materials may serve as the printed "ink", the template material that receives printed material, or both. In some embodiments, the supramolecular bonding in an ink material enables a solid or (hydro)gel to be pushed through a channel, as in extrusion from a needle, as the driving stimulus of applied force causes bond dissociation that allows the material to behave in a fluid-like fashion. After the force is removed (for example, once the material leaves the needle and there are no tensile or compressive forces acting on the ink) bonds reform to stabilize the structure (see, e.g., FIG. 2). In the case of the supramolecular template, the bonding offers a means of filling the print volume with a support (hydro)gel, as opposed to air or liquid. Because the bonds dissociate during the application of force, a print head (e.g. needle) can be moved through the material, depositing an ink, which is then enclosed in the (hydro)gel as bonds reform (see, e.g., FIG. 3). Any breaks in the material left by the needle will be healed by bonds that reform Unlike air or liquid, the supramolecular template supports the ink at all places within its 3-D volume. It is thus possible to print structures that would collapse in other media—for example overhangs, spirals, or spherical pockets of material with no other ink below them (see, e.g., FIG. 4).

In some embodiments, the methods of manufacturing a three-dimensional (3-D) structure comprise delivering a volume of a first ink material into a volume of at least one template material, thereby forming a two- or three dimensional patterned volume of the first ink material within the volume of the at least one template material. The template material comprises a self-healing supramolecular (hydro)gel capable of maintaining the substantial shape and dimensional stability of the two- or three dimensional pattern of the delivered volume of the first ink material.

Such methods may be repeated at least once and applied serially, or in parallel. In those cases where the printed material is a supramolecular material, once it has been printed, it can subsequently serve in the role of a support (hydro)gel. Thus, it is possible to print material in a given location in 3-D space, and then return to that location and print more material (see, e.g., FIG. 5). This capability is unique among 3-D printing technologies, and enables, for example, the layering of printed materials within/around one another, or the joining of regions of printed materials to create interpenetrating structures.

In certain embodiments, the methods further comprise delivering a volume of a second ink and optionally subsequent volumes of subsequent ink materials (a) into the volume of the at least one template material; (b) into a volume of at least one of an earlier delivered ink material, or (c) into both the volume of the at least one template material and a volume of at least one of the earlier delivered ink materials, thereby forming a two- or three dimensional patterned volume of the second and optionally subsequent ink material, the at least one template material comprising a self-healing supramolecular (hydro)gel capable of maintaining the substantial shape and dimensional stability of the two- or three dimensional pattern of the delivered volume of the ink materials.

The respective ink materials may be delivered by any suitable means, but in preferred embodiments, at least one of the ink materials is delivered by injection into or through the respective volume of the preceding ink or template material. Such injection may be accomplished by using a needle, cannula, catheter, or other tubing. It should be apparent that, in such cases, the dimensions of the internal volumes of the ink material(s) is defined by the internal dimensions of the injection devices used. As devices ranging from nanotube cellular probes through standard micron or millimeter dimensioned needles or other such devices are known, and can be used by these inventive methods, these internal structures may be defined as having at least one cross-sectional dimension (typically the diameter of a channel) in a range of from about 100 nm to about 500 nm, from about 500 nm to about 1000 nm, from about 1 micron to about 5 microns, from about 5 microns to about 10 microns, from about 10 microns to about 50 microns, from about 50 microns to about 100 microns, from about 100 microns to about 500 microns, from about 500 microns to about 1000 microns, from about 1 millimeter to about 5 millimeters, from about 5 millimeters to about 10 millimeters, or larger, or any combination of two or more of these ranges. Note also that, depending on the nature of the specific ink materials used, their further processing (for example, polymerization or crosslinking as described below) may result in expansion or contraction of the initially injected volumes, which may need to be considered in defining the ultimately desired dimensions. While the delivery devices typically have circular or ovoid cross-sections, devices with other cross-sectional shapes (e.g., triangles, squares. or other polygonal shapes, stars, etc.) can be employed to derive correspondingly shaped channels or tunnels.

Similarly, the lengths of internal channels or dimensions of internal voids can be any of the dimensions described above, as these are defined by the size of the original templates, which can be on the order of from about 100 nm to 1000 nm, from about 1 micron to about 1000 microns, from about 1 mm to about 10 mm, 100 mm, 1000 mm, or even larger. The templates can also be shape molded prior to providing (injecting) the ink materials, thereby providing articles nearly shape fit for their ultimate use, even before introduction of the inks, or subsequent selective removal techniques.

The term "self-healing supramolecular (hydro)gel" is described elsewhere herein, but an important characteristic of such materials is the ability to self-heal—i.e., to retain its essential shape, but also repair defects within its structure—for example, to close internal air (or other gas)-filled channels left by the penetration and subsequent removal of the insertion devices used to inject the inks into the template or into or through other inks Without necessarily being bound by the correctness of any particular theory, it is believed that such self-healing arises because of the shear thinning nature of the material, including those having host-guest pairing of moieties providing internal dynamic forces (e.g., hydrodynamic forces in the case of (hydro)gels) that cause intermolecular movement within the (hydro)gel framework. This phenomenon is further described elsewhere herein.

The templates of the present disclosure may comprise one or more materials, provided that at least one of the materials into which the inks are delivered fulfills the requirements of this self-healing, and preferably is a shear-thinning supramolecular (hydro)gel. Such a structure may comprise a layered structure in which a supramolecular (hydro)gel is sandwiched between two non-shear thinning polymers. Alternatively, the template may comprise a supramolecular (hydro)gel comprising dispersed organic and/or inorganic materials or devices. The structure of the template material is maintained through the printing process by bonds that are broken by the process of extrusion but reform afterwards. The network of material held together by these bonds may also entrap other materials, such as uncrosslinked polymeric material, proteins, or other molecules. The key is that the solid matter that makes up both the support and printed (hydro)gel material can be disrupted with stimulus and reassemble once the stimulus is gone, providing the structure that defines the print and also supports it in 3-D space.

These supramolecular (hydro)gels provide structure and support for the volume(s) of delivered ink(s); i.e., they provide sufficient support to maintain the "shape and dimensional stability" of the delivered ink. This stability may arise simply from physical forces exhibited by the materials, or the one or more inks may actually chemically bond to other inks or the template. It should be apparent that the term "shape and dimensional stability" refers to the ability to maintain and control the substantial shape and dimensions of the delivered volume(s) of ink(s) such that these are reflective of those necessary for the intended use of the final structure. Alternatively, this may be described as the stability in deposited shape and location that can be predicted from (hydro)gel properties and hardware capabilities based on measured properties of the printing (materials and hardware) system, such as swelling, diffusion, and reorganization of the (hydro)gel network with aging, and including printer resolution and print head capabilities (e.g. effects of its motion on the material). While some applications may be more forgiving than others, in some independent embodiments, the dimensions of the delivered volumes vary less than 50%, less than 25%, less than 10%, less than 5%, less than 1%, less than 0.5%, less than 0.1%, or maintain their original delivered dimensions during subsequent processing. Such variances may be caused, for example, by changes during crosslinking of one or more ink or template.

Each of the ink materials of the present disclosure is preferably, but not necessarily, shear-thinning. Also, each of the ink materials is preferably, but not necessarily, a supramolecular (hydro) gel. In either of these cases, the at least one of the ink materials may comprise a shear thinning material that sets to a solid or semi-solid upon delivery into the respective volume of preceding ink or template material. In certain non-limiting embodiments, for example, polymerizable non-shear-thinning inks, subsequently polymerized, can be used. In other non-limiting examples, polymerizable non-shear-thinning inks, left unpolymerized, can be used. In the former case, subsequent removal of the template can leave a polymerized 3-D article. In the latter case, polymerizing the template and removing the fluid ink can be used to develop a channeled template article.

In various embodiments, the first, second, or optionally subsequent ink materials each comprises a (hydro)gel (optionally supramolecular) that is compositionally different than the supramolecular (hydro)gel of at least one of the template materials. Additionally, each of the first, second, or optionally subsequent ink materials or template material, may be compositionally the same as or different from the other materials.

The flexibility of the present disclosure provides for an enormous range of options of final or intermediate products. In but one, non-limiting example, using three inks and two template materials in which the first template material (discontinuous phase which is not a supramolecular (hydro) gel) is dispersed in the second template material (continuous phase which is a supramolecular (hydro)gel), the three inks could be independently a supramolecular hydrophobic gel, a crosslinkable supramolecular (hydro)gel, and an epoxy resin. In a second, non-limiting example, involving one template and three inks, the first ink may be delivered to form a curved tube within the template, the second ink comprising a different material than the first may be introduced to be disposed entirely within the first ink volume (e.g., in a concentric volume), and the third ink being introduced to pass through the template and intersect (pass through) the concentric first and second ink volumes. Other combinations or derivative volumes may be considered.

Figure 6:
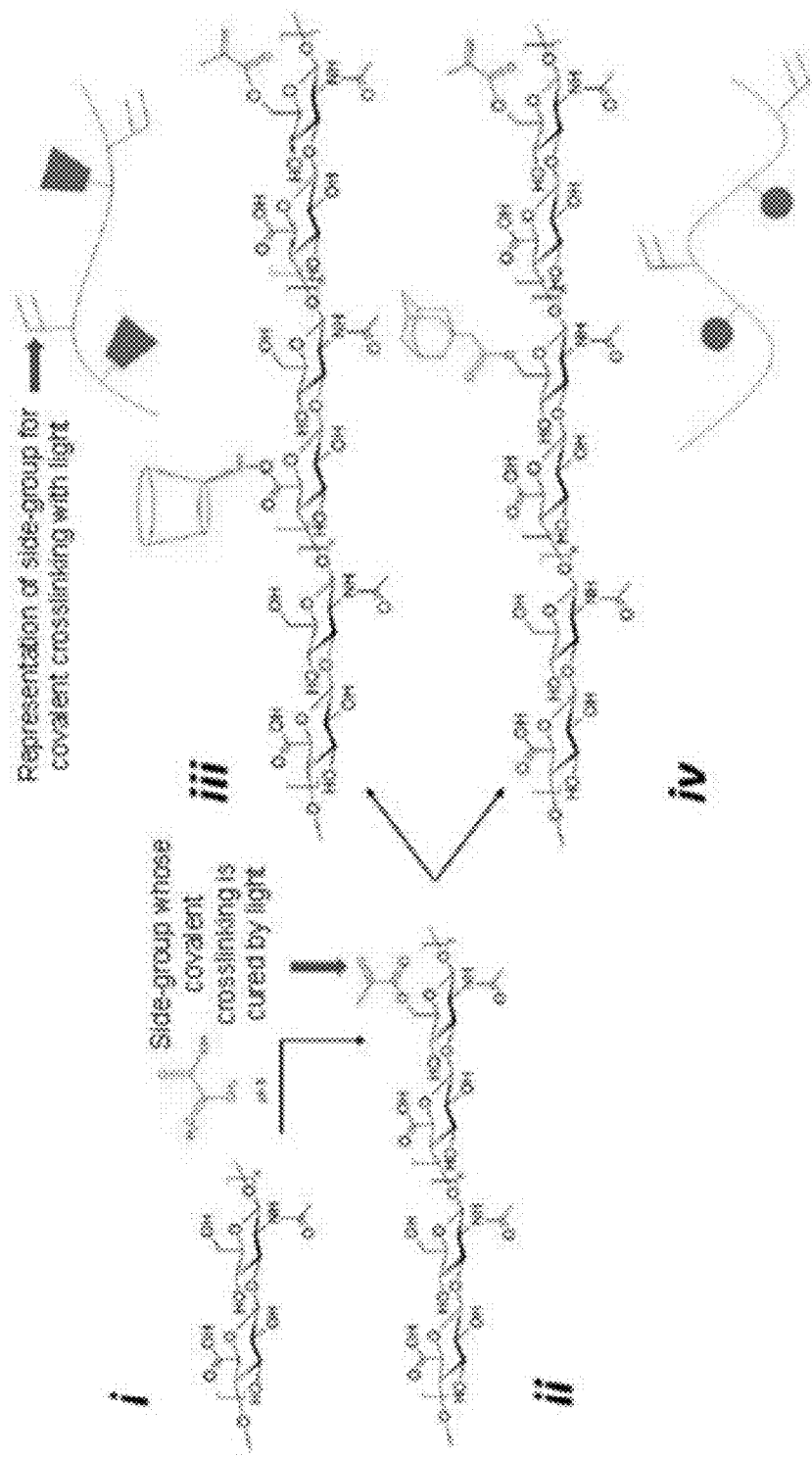
FIGS. 6-8 illustrate how secondary crosslinking allows inks or scaffolds to be stabilized against disruptive stimuli.

In still other embodiments, the methods may comprise use of materials in which any one of the at least one ink materials, at least one template material, or any combination thereof independently comprise a selectively-settable, shear-thinning supramolecular (hydro)gel comprising a polymer network, said polymer network comprising non-covalent crosslinks and at least one set of chemical moieties being capable of participating in at least one chemical covalent cross-linking reaction. That is, either one or more ink materials or one or more template material may comprise secondary crosslinking mechanisms that allow stabilization (see, e.g., FIG. 6). When such potential cross-linking sets of chemical moieties are present, further embodiments provide independently triggering one or more of these reactions, thereby providing a structure having at least one crosslinked element. Such chemistries are described more fully below.

This ability to selectively crosslink portions of the ink materials or template materials (or both) enables any printed structures to be stabilized and the support material removed or vice versa. The latter case, where the printed material is removed and the support stabilized, allows for the printing of channels (see, e.g., FIG. 7). The former case enables the printing of complex 3D structures that cannot be achieved through other 3D printing methods (see, e.g., FIG. 8). The disruption of supramolecular bonds can be easily achieved through the application of various perturbations, for example chemicals that disrupt bonding, or physical forces or energy that cause bonds to dissociate.

The disclosure also contemplates those embodiments, further comprising selective removing at least a portion of any one of the at least one ink materials, the template material, or any combination thereof. This selective removal may be accomplished whether or not any portion of the assembly has been cross-linked, and if so crosslinked, before or after such crosslinking Such a selective removal may result in a structure comprising the template material having channels, tunnels, internal cavities or voids. In some embodiments, the resulting channels, tunnels, internal cavities, or voids may be interconnected in one, two, or three dimensions within the structure. The dimensions of these channels, tunnels, internal cavities, or voids may be as described above for these features.

In other embodiments, the methods further comprise selectively removing at least a portion of the template material. Again, this selective removal may be accomplished whether or not any portion of the assembly has been cross-linked, and if so crosslinked, before or after such crosslinking. The selective removal of the template material may result in a shaped structure comprising at least one of the ink materials, either cured or uncured.

The selective removal of a portion of one or more inks or a portion of the template material may be done serially, such that, for example, the removal of a portion of the template material precedes or follows (or both) any selective removal of one or more ink materials. Such removals, for example, may result in shaped structures comprising residual template materials containing internal channels.

The flexibility of the present disclosure is further developed by the ability to incorporate materials or devices within any one or more of the inks or any portion of the template material. For example, in certain embodiments, any one of the at least one of the ink materials, the template material, or any combination thereof, may independently comprise pharmaceutically active drugs or neutraceuticals; populations of cells (including mammalian stem cells and progenitor cells); peptides or peptide derivatives; one or more types of nanoparticles (carbon, metallic, semiconductor, or inorganic oxide, carbide, or nitride) or quantum dots; conductive fillers (such as nanoscale carbon or metals), fluorescent or phosphorescent materials; magnetic materials; or combination thereof. Any one or more of these materials may also comprise a functional electronic device, such that the resulting structure forms an electrical or sensing connection to such a device. Similarly, the template material may be positioned adjacent to an electronic substrate material, comprising such a device, such that later formed channels or tunnels have access to devices capable of acting as chemical sensors or other electronic components.

In some embodiments, further elaborated below, at least one, and preferably all, of the ink materials, the template materials, or additives thereof are biocompatible. In some cases, at least one, and preferably all, of the ink materials, the template materials, or additives thereof are suitable for implanting into a mammal, preferably a human.

To this point, the disclosure has been described in terms of methods, with some reference to descriptions of intermediate and final articles, so it should be apparent that the disclosure also includes those articles comprising a structure prepared by any of the methods described herein whether as an intermediate or final structure or device. Such exemplary non-limiting structures may provide the basis for, or be incorporated into, such devices as blood analyzers, micro-/nano-fluidic conduction or mixing devices, macro-, micro-, or nano-scale reaction vessels, artificial/replacement tissue scaffolds, tissue models, pumps, balloons, sensors (e.g., for toxins/pathogens, biomarkers), filters, and cell culture platforms. In other embodiments, the exemplary non-limiting structures may provide the bases for, or be incorporated into, such devices as shaped implantable tissue graft scaffolds, implantable cellular matrices, drug release reservoirs, model tissues, implantable (hydro)gels, including those for filling/bulking spaces energy storage devices, wound dressings, and sorption devices. Such devices are considered within the scope of the present disclosure.

Supramolecular (Hydro)Gel Materials

To the extent that the present disclosure is said to be directed to settable, shear-thinning, self-healing gels, including (hydro)gels, these comprise non-covalent crosslinks (giving rise to the ability to deform and flow into liquids under shear-stress and recover back into the gels or (hydro) gels upon stress removal). Supramolecular (hydro)gels, as described herein, exhibit the property of self-healing, as described above. In some cases, these also comprise (hydro) gels, comprising chemical moieties which provide for the ability to form chemical covalent crosslinks which can then stabilize the (hydro)gel network. In certain embodiments, this recovery from shear is complete within minutes or even seconds.

Various embodiments of these (hydro)gels are described in PCT/US13/52641, filed Jul. 30, 2013, which is incorporated by reference in its entirety for all purposes.

Various embodiments, then, provide settable (curable), shear-thinning, and self-healing (hydro)gels, each (hydro) gel comprising a hydrophilic polymer network, said hydrophilic polymer network comprising non-covalent crosslinks and potentially a set of chemical moieties being capable of participating in at least one chemical covalent cross-linking reaction.

As described herein, a shear-thinning (hydro)gel is a (hydro)gel capable of self-assembling into a gelled network by interaction of its associated non-covalent linkages. When subjected to a mechanical shear (such as when forced to flow through a needle, catheter, or cannula), at least some of the non-covalent linkages within the (hydro)gel disassociate, leading to a disassembly of the gel network and a temporary thinning of the gel (lowering of the viscosity). Upon the removal of the mechanical shear force, the original gel re-assembles/recovers to a state (e.g., viscosity, stiffness, or diffusivity) the same as, or close to, it pre-shear state. Without intending to be bound by the correctness of any particular theory, this property is believed to be responsible, at least in part, for their self-healing nature. The term "shear-thinning (hydro)gels" are used in the literatures to describe such gels where the recovery of the (hydro)gel after shear can be nearly instantaneous or be as long as hours. While the present disclosure contemplates (hydro)gels which are included within this broad context, particular independent embodiments include those characterized as "rapid healing" or "rapid recovery" (hydro)gels, where, upon the removal of the mechanical shear force, the original gel recovers within 30 minutes, preferably within about 20, 10, 5 or about 1 minute, or within about 60, 45, 15, 10, 5, or about 1 second. The types of shear-thinning (hydro)gels falling within this narrower category are summarized in Guvendiren, et al., "Shear-thinning (hydro)gels for biomedical applications," Soft Matter, 2012, 8, 260-272, which is incorporated by reference herein in its entirety for all purposes. All of the (hydro)gels described within this Guvendiren article, modified to incorporate the chemical moieties capable of participating in at least one chemical covalent cross-linking reaction, as could be accomplished by the skilled artisan, are considered separate embodiments of the present disclosure.

For the sake of absolute clarity, in specific embodiments, the settable shear-thinning (hydro)gel comprises a peptide-based (hydro)gel, a protein-based (hydro)gel, a blended polymer (hydro)gel, a colloidal (hydro)gel, or a guest-host-based (hydro)gel.

In particular embodiments, each settable, shear thinning, self-healing (hydro)gel comprises a guest-host-based (hydro)gel, comprising a host-polymer and a guest-polymer, linked through a plurality of host-guest pairings of non-covalent bonding moieties (plurality here refers to number of crosslinks, not necessarily types of non-covalent cross-links). A subset of these embodiments provides that the host-polymer comprises a first hydrophilic polymer comprising a plurality of a moieties having a hydrophobic cavity; and the guest-polymer comprises a second hydrophilic polymer comprising a plurality of hydrophobic anchoring moieties (again here, plurality here refers to number of crosslinks, not necessarily types of non-covalent crosslinks) More specific embodiments provide that the moieties capable of providing a hydrophobic cavity comprise a calixarene, a cucurbit[n]uril, or a cyclodextrin, in each case optionally substituted with one or more pendant alkyl, alkanol (e.g., hydroxypropanol), alcohol, alkoxy, aromatic, sugar moieties or vinyl groups. Embodiments described as comprising an optionally substituted cyclodextrin, include those wherein the cyclodextrin is an alpha, beta, or gamma-cyclodextrin, preferably an optionally substituted beta-cyclodextrin.

Another subset of embodiments wherein a settable, shear thinning, self-healing (hydro)gel of the present disclosure comprises a guest-host-based (hydro)gel includes those wherein the hydrophobic anchoring moiety comprises a linear, branched, cyclic, or polycyclic $C_{6\text{-}20}$ hydrocarbon, $C_{6\text{-}20}$ aryl or alkylaryl, hetero or alkylaromatic hydrocarbon moieties. In one preferred embodiment, the hydrophobic anchoring moiety comprises an adamantane.

Certain other embodiments described as involving a guest-host strategy, include those wherein the host-guest pairing of moiety comprise an alpha-cyclodextrin/hexyl group pair, an alpha-cyclodextrin/polyethylene oxide group pair, a beta-cyclodextrin/adamantane group pair, a beta-cyclodextrin/cyclohexyl group pair, a beta-cyclodextrin/benzyl group pair, a gamma-cyclodextrin/cyclodecyl group pair, a cucurbit[6]uril/hexanediamine group pair, or a cucurbit[6]uril/spermine group pair.

Within those embodiments described by a guest-host relationship, the first and second polymers associated with the host-polymer and guest-polymer, respectively, may each comprise any of the polymers described below, but preferred embodiments are those wherein at least one of the first or second hydrophilic polymers comprises hyaluronic acid. In other preferred embodiments, both the first and second hydrophilic polymers both comprise hyaluronic acid.

In a specific, non-limiting example, the host-polymer moiety comprises a polymer comprising hyaluronic acid to which is attached a plurality of a beta-cyclodextrin moieties; and the guest-polymer comprises a polymer comprising hyaluronic acid to which is attached a plurality of a adamantine groups; and potentially one set of chemical moieties capable of chemically, covalently cross-linking the (hydro) gel is an acrylic or methacrylate group. When the components are mixed, the hydrophobic adamantine becomes non-covalently bound inside of the hydrophobic beta-cyclodextrin cavity to yield physical cross-links and self-assembly to form a settable, shear-thinning (hydro)gel. Secondary covalent cross-linking of the material is obtainable by the photocatalytic, free-radical crosslinking of the acrylate groups.

In certain embodiments, the host-polymer comprises a moiety having a hydrophilic cavity linked to a first hydrophilic polymer; and the guest-polymer comprises a hydrophilic anchoring moiety linked to a second hydrophilic polymer. Such a hydrophilic cavity may comprise a crypt and/or crown ether.

In other embodiments, the settable, shear thinning (hydro) gel of the present disclosure operates by a two-component Dock- and Lock (DnL) self-assembling (hydro)gelation mechanism, using bio-conjugate materials. Such a mechanism, and the associated class of shear thinning (hydro)gels, is described in H. D. Lu, M. B. Charati, I. L. Kim, J. A. Burdick, Injectable Shear-Thinning Hydrogels Engineered with a Self-Assembling Dock-and-Lock Mechanism, Biomaterials, 33:2145-2133, 2012, which is incorporated by reference herein for all purposes. All of the (hydro)gels described within this Lu article, modified to incorporate the chemical moieties capable of participating in at least one chemical covalent cross-linking reaction, as could be accomplished by the skilled artisan, are considered separate embodiments of the present disclosure. In certain of these embodiments, the (hydro)gel comprises a docking and dimerization domain (rDDD), comprising a dimer of RIIα cAMP dependent PKA recombinant protein, linked together by a hydrophilic peptide spacer containing integrin binding domains. These (hydro)gels may also or alternatively comprise a locking anchoring domain (LOCK-AD), wherein the LOCK-AD comprises an A-kinase anchoring polypeptide modified with solubilizing amino acid sequences conjugated hydrophilic polymer backbone. These rDDD and LOCK-AD moieties may be linked by any of the hydrophilic polymers described below, but preferably comprise polyethylene glycol or hyaluronic acid. In some embodiments, chemical moieties being capable of participating in at least one chemical covalent cross-linking reaction in these DnL (hydro)gels are included and comprise an acrylate or methacrylate group at the peptide N terminus or along the hydrophilic polymer backbone, said acrylate or methacrylate group capable of polymerizing with exposure to light.

As described above, various embodiments, provide settable (curable), shear-thinning (hydro)gels, each (hydro)gel comprising a hydrophilic polymer network, said hydrophilic polymer network comprising non-covalent crosslinks and potentially a set of chemical moieties being capable of participating in at least one chemical covalent cross-linking reaction. The types of chemical moieties which may accomplish this "spontaneous" covalent crosslinking may be described in terms of the chemistries described below, but preferred embodiments are those where the reactants are chosen such that the kinetics of the covalent cross-linking are "slow" with respect to mixing and application to the intended site. That is, the term "slow" reflects that the chemical covalent crosslinking provides an observable effect on the properties of the gel only at times in excess of 30 minutes. In but one example, systems comprising a hydrophilic polymer modified with vinyl sulfone and another modified with a thiol may be used.

In comparison, separate embodiments provide those settable (curable), shear-thinning (hydro)gels, wherein the at least one chemical covalent cross-linking reaction is initiated by an internal or external (both relative to the (hydro) gel itself) trigger. In these embodiments, the shear-thinning (hydro)gels may be described as "selective settable" (hydro) gels, the term "selective" referring to the fact that the user may select when and how to initiate the chemical covalent cross-linking reactions (beyond the act simple mixing).

The hydrophilic polymer network of the settable shear thinning (hydro)gels may also comprise more than one— i.e., at least two—sets of chemical moieties, each set being capable of independently participating in at least one chemical covalent cross-linking reaction. That is, in various aspects of the present disclosure, a given (hydro)gel may contain one, two, or more sets of chemical moieties capable of participating in a chemical covalent crosslinking reaction. In separate embodiments, these occur spontaneously or as triggered. Each covalent cross-linking reaction may occur by a similar mechanism (e.g., a condensation reaction), albeit with different chemical moieties, or by different mechanisms. In either case the reactions may be independently triggered (e.g., by different wavelengths of light or application of different stimuli), by an internal or external stimulus or stimuli, or operate at different rates (e.g., two condensation reactions may have different kinetics by virtue of different nucleophiles, electrophiles, steric hindrance, etc.).

For each mechanism, the chemical covalent crosslinking results in a covalently cross-linked (hydro)gel having a mechanical stability that is higher than the mechanical stability of the shear-thinning (hydro)gel before chemical cross-linking. In separate embodiments, this "higher" mechanical stability may be described in terms of improved resistance to bio-erosion—defined in terms of disassociation of the non-covalent linkages; i.e., improved resistance correlating with longer times necessary to realize degradation of the polymer network—or increased viscosity, stiffness or higher storage or loss modulus of the polymer network. Within each of these property classes, this higher stability reflects an improvement or increase in at least one physical property of at least about 10%, at least about 25%, at least about 50%, or at least about 100%, or at least about 2 times, at least about 5 times, or at least about 10 times relative to the corresponding property of the shear-thinning (hydro)gel. So as to be clear, in one exemplary embodiment, FIG. 9 shows that a cross-linked DnL gel remains stable (i.e., at a normalized erosion of ca. 10%) for more than 8 weeks, whereas the non-cross-linked (hydro)gel is virtually completely degraded within days. In another example, FIG. 10 illustrates that the storage modulus of a modified cyclodextrin/adamantine/hyaluronic acid (hydro)gel network increased from ca. 2000 to more than about 10,000 Pa after crosslinking the pendant methacrylate groups.

In other embodiments, the chemical covalent crosslinking moieties are capable of, or actually, resulting in a covalently cross-linked (hydro)gel having a mechanical stability that is higher than the mechanical stability of the shear-thinning (hydro)gel before chemical cross-linking and/or the chemical covalent crosslinking reaction provides a covalently cross-linked (hydro)gel exhibiting reduced diffusivity of an entrained material relative to the diffusivity exhibited by the shear-thinning (hydro)gel before chemical cross-linking. As contemplated herein, the entrained material may include a pharmaceutically active drug or neutraceutical, a population of cells, a nanoparticle, quantum dot, or magnetic material. The diffusivity rate would be measured by standards means, for example by measuring the release of a macromolecule of known molecular weight (e.g., a dextran or bovine serum albumin) form a (hydro)gel into solution or by measuring the uptake of the same molecules into the (hydro)gel.

As described above, the settable, shear-thinning (hydro) gels comprise a hydrophilic polymer network, comprising hydrophilic polymers or copolymers containing hydrophilic polymer subunits. These polymers may comprise natural, synthetic, biocompatible, biodegradable, non-biodegradable, and/or biosorbable building blocks. Unless specifically restricted to one or more of these categories, the polymers may comprise materials from any one of these categories. For performance reasons, it may be desirable to incorporate biodegradable or porogenic materials into the design.

The term "polymer" is not intended to necessarily refer to a single polymer molecule; rather it is intended to connote a mixture of individual molecules, said mixture having a distribution of molecular weights, as is understood by those skilled in the art. The present invention is not limited to any particular molecule weight distribution, provided the distribution provides a mixture suitable for the purposes described herein. For example, a polymer comprising hyaluronic acid refers to a mixture of individual polymer molecules, each molecule comprising hyaluronic acid.

The phrase "synthetic polymer" refers to polymers that are not found in nature, even if the polymers are made from naturally occurring biomaterials. Examples include, but are not limited to, poly(amino acids), copoly(ether-esters), polyalkylenes, oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polysiloxanes, and combinations thereof.

Suitable synthetic polymers for use according to the teachings of the present disclosure can also include biosynthetic polymers based on sequences found in collagen, elastin, thrombin, fibronectin, starches, poly(amino acid), polypropylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include collagen-based materials, chitosan, hyaluronic acid and alginate.

The phrase "biocompatible polymer" refers to any polymer (synthetic or natural) which when in contact with cells, tissues or body or physiological fluid of an organism does not induce adverse effects such as immunological reactions and/or rejections and the like. It will be appreciated that a biocompatible polymer can also be a biodegradable polymer.

The phrase "biodegradable polymer" refers to a synthetic or natural polymer which can be degraded (i.e., broken down) in the physiological environment such as by enzymes, microbes, or proteins. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. Aliphatic polyesters, poly(amino acids), polyalkylene oxalates, polyamides, polyamido esters, poly(anhydrides), poly(beta-amino esters), polycarbonates, polyethers, polyorthoesters, polyphosphazenes, and combinations thereof are considered biodegradable. More specific examples of biodegradable polymers include, but are not limited to, collagen (e.g., Collagen I or IV), fibrin, hyaluronic acid, polylactic acid (PLA), polyglycolic acid (PGA), polycaprolactone (PCL), poly(lactide-co-glycolide) (PLGA), polydioxanone (PDO), trimethylene carbonate (TMC), polyethylene glycol (PEG), Collagen, PEG-DMA, alginate or alginic acid, chitosan polymers, or copolymers or mixtures thereof.

The phrase "non-biodegradable polymer" refers to a synthetic or natural polymer which is not degraded (i.e., broken down) in the physiological environment. Examples of non-biodegradable polymers include, but are not limited to, carbon, nylon, silicon, silk, polyurethanes, polycarbonates, polyacrylonitriles, polyanilines, polyvinyl carbazoles, polyvinyl chlorides, polyvinyl fluorides, polyvinyl imidazoles, polyvinyl alcohols, polystyrenes and poly(vinyl phenols), aliphatic polyesters, polyacrylates, polymethacrylates, acyl-substituted cellulose acetates, non-biodegradable polyurethanes, polystyrenes, chlorosulphonated polyolefins, polyethylene oxides, polytetrafluoroethylenes, polydialkylsiloxanes, and shape-memory materials such as poly (styrene-block-butadiene), copolymers or mixtures thereof.

The phrase "biosorbable" refers to those polymers which are absorbed within the host body, either through a biodegradation process, or by simple dissolution in aqueous or other body fluids. Water soluble polymers, such as poly (ethylene oxide) are included in this class of polymers.

The term "co-polymer" as used herein, refers to a polymer of at least two chemically distinct monomers. Non-limiting examples of co-polymers which may be used within the (hydro)gels of the present disclosure include, PLA-PEG, PEGT-PBT, PLA-PGA, PEG-PCL and PCL-PLA. The use of copolymers or mixtures of polymers/copolymers provides a flexible means of providing the required blend of properties. In but one non-limiting example, functionalized poly (β-amino esters), which may be formed by the conjugate addition of primary or secondary amines with di-acrylates, can provide a range of materials exhibiting a wide array of advantageous properties for this purpose. Such materials are described, for example, in Anderson, et al., "A Combinatorial Library of Photocrosslinkable and Degradable Materials," Adv. Materials, vol. 18 (19), 2006, this reference being incorporated by reference in its entirety.

In certain preferred embodiments, the settable shear-thinning (hydro)gels comprise an agarose, alginate, RGD-modified alginate, amylase, amylpectin, cellularose, chitosan, collagen, dextran, fibrin, gelatin, glycogen, heparin, hyaluronic acid, oligo(poly(ethylene glycol)fumarate), poly (ε-caprolactone), poly(ethylene glycol), poly(acrylamide), poly(β-aminoester), poly(caprolactone), multi-arm polyethylene glycol, poly-hydroxyethyl acrylate, poly(hydroxyethyl methacrylate), poly(N-isopropylacrylamide), poly (glycolic acid), poly(lactic acid), poly(lactic acid-glycolic acid), oligo(poly(ethylene glycol)fumarate), poly(vinyl alcohol), or a poly(vinyl acid).

With the respect to the chemical moieties capable of chemical covalent crosslinking, the term "at least one set" refers to the fact that typically, but not necessarily, are the chemical moieties are different chemical groups which react together to form a cross-link; i.e., from this perspective, the "at least one set" may be envisioned as comprising a matched pair of chemical groups. For example, a set may comprise a carboxylic acid (or equivalent) and an amine or alcohol (or equivalent), together capable of forming an amide or ester cross-linked linkage. In another example, a set may comprise a thiol group and a vinyl group, together capable of forming a thiol ether on reaction with light. Another set may comprise a hydrazide and an aldehyde or ketone, capable of forming a hydrazone. Or a set may comprise simply a single radical polymerizable moiety, such as an acrylate or methacrylate.

In individual embodiments, each of the different chemical groups which may react together to form a covalent cross-link within the network may be attached to the same or a different polymer within the polymer network. In non-limiting examples relating to the guest-host-based (hydro) gels described above, for a given set of chemical cross-linkable moieties, (a) one chemical group may be attached to the first polymer while the associated "matching" chemical group is attached to the second polymer, or (b) both chemical groups may be attached to either the first or second polymer or (c) a combination of the (a) and (b). Where more than one set of chemical covalent cross-linkable moieties are present, each set may be independently arranged are described above.

These at least one set of chemical covalent cross-linkable moieties may be attached as a pendant to at least one polymer of the network, either directly to the polymer backbone or via a linking group. In some embodiments, this linking group may be biodegradable (e.g., under physiological conditions), such that after the (hydro)gel is cross-linked, the linking group may degrade with time, thereby reducing the physical strength of the original cross-linked performance or releasing any cargo contained within the cross-linked (hydro)gel.

In other embodiments, the chemical covalent cross-linkable moieties may be embedded within the polymer backbone of at least one polymer of the network. Olefin or epoxy moieties may be examples of this strategy.

In other embodiments, the settable, shear thinning, self-healing (hydro)gel may comprise moieties capable of fluorescing or phosphorescing after exposure to light. Such moieties are known in the art, for example a Cy7.5 dye. Such a marker would be useful, for example, to measure degradation (or stability) performance of the (hydro)gel in use, or trigger-able upon exposure to a specific analyte in a sensor application.

In certain embodiments, where the chemical moieties capable of chemical covalent crosslinking are activated, or "triggered" by exposure to radiation, for example light of a specific wavelength or wavelengths (i.e., the (hydro)gel may contain multiple such chemical sets, each triggerable by a different wavelength of light). In such case, the stimulus/ stimuli may be light having a wavelength within the near infrared to ultraviolet range. See, e.g., Tan, et al., *J. Biomed Mad. Res.*, vol. 87 (4), 2008, pp. 1034-1043, which is incorporated by reference in its entirety, for examples of chemical moieties triggerable by light. In those compositions wherein the chemical moieties are light activated, it would also be advantageous that the (hydro)gel further comprises a photo-initiator; for example, 1-[4-(2-hydroxyethoxy)-phenyl]-2-hydroxy-2-methyl-1-propane-1-one, available from Ciba Specialty Chemicals, Inc. as IRGACURE 2959. Other exemplary photo-initiators include 2,4, 6-trimethylbenzoyldiphenyl phosphine oxide, 2-hydroxy-2-methyl-1-phenyl-propanone, oligo (2-hydroxy-2-methyl-1-(4-(1-methylvinyl)vinyl) propanone), and 2,4,6-trimethylbenzophonone.

In other embodiments, the external stimulus to the chemical covalent crosslinking reaction may be radiation in the microwave range (i.e., in the range of about 1 MHz to about 10 GHz). In still other embodiments, the external stimulus may be a change in pH or temperature, a free radical initiator, or a combination thereof. Where the chemical covalent cross-linking reaction is a free radical polymerization, the (hydro)gel may further comprise a thermal radical initiator. Exemplary free radical initiators include azobisisobutyronitrile, dilauroyl peroxide lauroyl acid, dioctanoyl peroxide caprylic acid, didecanoyl peroxide n-decanoic acid, di-n-propionyl peroxide propionic acid, bis(3,5,5-trimethylhexanoyl) 3,5,5-trimethyl peroxide hexanoic acid, dibenzoyl peroxide benzoic acid, bis(2,4-dichlorobenzoyl) 2,4 dichlorobenzoic acid peroxide, bis(o-methylbenzoyl) peroxide o-methyl benzoic acid, acetyl cyclohexane sulphonyl cyclohexane sulphonic peroxide acid, t-butylperoxypivalate pivalic acid, t-butyl peroxy-2-ethylhexanoate 2-ethyl caproic acid, t-butyl peroxy isobutyrate isobutyric acid, t-butyl peroxybenzoate benzoic acid, and mixtures thereof.

In certain embodiments, the covalent crosslinking reaction is a condensation reaction, Michael addition, or a free radical polymerization reaction. In related embodiments, the at least one set of chemical moieties capable of participating in a covalent chemical crosslinking reaction comprises an acrylate, acrylamide, optionally protected alcohol, aldehyde, alkyne, optionally protected amine, anhydride, azide, carboxy, epoxy, ester, hydrazide, ketone, maleimide, methacrylate, styrenyl, optionally protected thiol, or vinyl or vinyl sulfone group. In still further related embodiments, the product of the chemical covalent cross-linking reaction is an ester, ether, amide, hydrozone, polyacrylate, polymethacrylate, thioamide, thioester, thioether, or urethane. This skilled artisan would appreciate how to modify the desired polymer to attached or incorporate, the chemical covalent cross-linkable moiety.

Other embodiments describe these additional materials as comprising biofactors, therapeutic agents, particles (e.g., nanoparticles, quantum dots, or magnetic materials), or cells.

In one set of embodiments, these additional materials comprise at least one therapeutic compound or agent, capable of modifying cellular activity. Similarly, agents that act to increase cell attachment, cell spreading, cell proliferation, cell differentiation and/or cell migration in the scaffold may also be incorporated into the (hydro)gels. Such agents can be biological agents such as an amino acid, peptides, polypeptides, proteins, DNA, RNA, lipids and/or proteoglycans. These agents may also include growth factors, cytokines, proteases, and protease substrates.

Additionally and/or alternatively, the (hydro)gels of the present disclosure may comprise an antiproliferative agent, an immunosuppressant drug, and/or a non-thrombogenic or anti-adhesive substance.

The cells which can be used according to the teachings of the present disclosure may comprise non-autologous cells or non-autologous cells (e.g. allogeneic cells or xenogeneic cells), such as from human cadavers, human donors or xenogeneic (e.g. porcine or bovine) donors.

The cells may comprise a heterogeneous population of cells or a homogeneous population of cells. Such cells can be for example, stem cells, progenitor cells, or differentiated cells. Stem cells may include adipose derived stem cells, embryonic stem cells, bone marrow stem cells, cord blood stem cells, mesenchymal stem cells, adult stem cells, and pluripotent or induced pluripotent stem cells. Mesenchymal stem cells are preferred.

Furthermore, such cells may be live or non-viable and/or of autologous origin or non-autologous origin, such as postpartum-derived cells (as described in U.S. application Ser. Nos. 10/887,012 and 10/887,446). Typically the cells are selected according to the tissue being generated.

In additional to the settable, shear thinning (hydro)gels (i.e., which exists before the covalent crosslinking reaction (s) has occurred or is complete), individual embodiments of the present disclosure include those (hydro)gel compositions, based on the previous descriptions, which have undergone at least one of the covalent cross-linking reactions, either partially or completely. This includes embodiments where any number of the at least one set of the chemical moieties capable of covalent crosslinking of settable, shear thinning (hydro)gel has reacted, either partially or entirely.

In separate embodiments, the cured (hydro)gels exhibit a higher stability or lower diffusivity than the pre-cured (i.e., settable, shear thinning) (hydro)gel. In several of these embodiments, the cured, covalently cross-linked (hydro)gel exhibits a mechanical stability that is higher than the mechanical stability of the (pre-cured) shear-thinning (hydro)gel (i.e., before covalent crosslinking). In separate embodiments, this "higher" mechanical stability may be described in terms of improved resistance to bio-erosion—defined in terms of disassociation of the non-covalent linkages; i.e., improved resistance correlating with longer times necessary to realize degradation of the polymer network—or increased viscosity, stiffness or higher storage or loss modulus of the polymer network. Within each of these property classes, this higher stability reflects an improvement or increase in at least one physical property of at least about 10%, at least about 25%, at least about 50%, or at least about 100%, or at least about 2 times, at least about 5 times, or at least about 10 times, relative to the corresponding property of the shear-thinning (hydro)gel. So as to be clear, in one exemplary embodiment, FIG. 9 shows that a cross-linked DnL gel remains stable for more than 8 weeks (normalized erosion ca. 10%), whereas the non-cross-linked cogener is virtually completely degraded within days. In another example, FIG. 10 illustrates that the storage modulus of a modified cyclodextrin/adamantine/hyaluronic acid (hydro) gel network increased from ca. 2000 to more than about 10,000 Pa after crosslinking the pendant methacrylate groups.

Further, the settable, shear-thinning (hydro)gels and associated cured (hydro)gels may be applied in-vivo and/or ex-vivo. Various embodiments provide that the settable or cured (hydro)gels are adapted to be medically acceptable for use in a mammal, including those where the mammal is a human. Such embodiments include those where the materials are at least biocompatible, and preferably approved by the United States Food and Drug Administration in the United States (or a corresponding regulatory agency in other countries).

The materials described herein may be used to control encapsulated cell behavior, improve delivered cell retention, and control cellular release rates. These materials can also be used to tune encapsulated drug release profiles and pharmacokinetics.

Additional exemplary applications of the present disclosure include those where the settable, shear-thinning (hydro) gels and associated cured (hydro)gels:
  scaffolds in tissue engineering;
  vehicles for cell encapsulation and delivery;
  sustained- or controlled release drug delivery systems;
  biosensors, including those responsive to specific molecules, such as glucose or antigens;
  contact lenses;
  adhesives, including medical and electronic adhesives
  biosealants;
  dressings for healing of burn or other hard-to-heal wounds.
  and reservoirs in topical drug delivery; particularly ionic drugs, delivered by iontophoresis Certain embodiments also provide methods of preparing a controlled or sustained release formulation of a pharmaceutically active drug, neutraceutical, cell population, or particle array in a patient, each method comprising introducing into the patient a composition comprising a settable, shear-thinning (hydro)gel as described herein, and a pharmaceutically active drug, neutraceutical, cell population; or particle. Other embodiments further comprise triggering at least one chemical covalent crosslinking reaction.

Other independent embodiments provide methods of preparing a controlled release formulation of a pharmaceutically active drug, neutraceutical, or cell population in a patient, each method comprising introducing into a patient the composition comprising (a) a settable shear-thinning (hydro)gel comprising a network hydrophilic polymers, said hydrophilic polymer network comprising non-covalent crosslinks and at least one set of chemical moieties being capable of participating in at least one chemical covalent cross-linking reaction; and (b) a pharmaceutically active drug, neutraceutical, or cell population.

EMBODIMENTS

Embodiment 1

A method of manufacturing a three-dimensional (3-D) structure, said method comprising:
  delivering a volume of a first ink material into a volume of at least one template material thereby forming a two- or three dimensional patterned volume of the first ink material within the volume of the at least one template material, the at least one template material comprising a self-healing supramolecular gel capable of maintaining the shape and dimensional stability of the two- or three dimensional pattern of the delivered volume of the first ink material.

Embodiment 2

The method of Embodiment 1, further comprising delivering a volume of a second ink and optionally subsequent volumes of subsequent ink materials (a) into the volume of the at least one template material; (b) into a volume of at least one of an earlier delivered ink material, or (c) into both the volume of the at least one template material and a volume of at least one of the earlier delivered ink materials, thereby forming a two- or three dimensional patterned volume of the second and optionally subsequent ink material, the at least one template material comprising a self-healing supramolecular gel capable of maintaining the shape and dimensional stability of the two- or three dimensional pattern of the delivered volumes of the ink materials.

Embodiment 3

The method of Embodiment 1 or 2, wherein the first, second, or optionally subsequent ink materials each comprises a supramolecular gel that is compositionally different than the supramolecular gel of at least one of the template materials.

Embodiment 4

The method of Embodiment 2 or 3, as applied to claim 2, wherein each of the first, second, or optionally subsequent ink materials is compositionally different from the others.

Embodiment 5

The method of any one of Embodiments 1 to 4, wherein at least one of the ink materials is delivered by injection into the respective volume of the preceding ink or template material.

Embodiment 6

The method of any one of Embodiments 1 to 5, wherein the at least one ink material is injected using a needle, cannula, catheter, or tubing.

Embodiment 7

The method of any one of Embodiments 1 to 6, wherein at least one of the ink materials is a shear thinning material that sets to a solid or semi-solid upon delivery into the respective volume of preceding ink or template material.

Embodiment 8

The method of any one of Embodiments 1 to 7, wherein any one of the least one of the ink materials, the template material, or any combination thereof independently comprise a pharmaceutically active drug or neutraceutical; a population of cells (including mammalian stem cells and progenitor cells); a peptide or peptide derivative; one or more types of nanoparticles (carbon, metallic, semiconductor, or inorganic oxide, carbide, or nitride) or quantum dots; a fluorescent or phosphorescent material; a magnetic material; or combination thereof.

Embodiment 9

The method of any one of Embodiments 1 to 8, wherein any one of the at least one ink materials, the template material, or any combination thereof independently comprise a [selectively] settable, shear-thinning supramolecular gel comprising a polymer network, said polymer network comprising non-covalent crosslinks and at least one set of chemical moieties being capable of participating in at least one chemical covalent cross-linking reaction.

Embodiment 10

The method of any one of Embodiments 1 to 8, wherein any one of the at least one ink materials, the template material, or any combination thereof independently comprise a [selectively] settable, shear-thinning (hydro)gel comprising a hydrophilic polymer network, said hydrophilic polymer network comprising non-covalent crosslinks and at least one set of chemical moieties being capable of participating in at least one chemical covalent cross-linking reaction.

Embodiment 11

The method of Embodiment 9 or 10, further comprising independently triggering at least one chemical covalent crosslinking reaction within any one of the at least one ink materials, the template material, or any combination thereof.

Embodiment 12

The method of any one of Embodiments 1 to 11, further comprising selective removing at least a portion of any one of the at least one ink materials, the template material, or any combination thereof.

Embodiment 13

The method of Embodiment 12, wherein the selective removal of at least a portion of any one of the at least one ink materials, the template material, or any combination thereof results in a structure comprising the template material having channels, tunnels, internal cavities or voids.

Embodiment 14

The method of Embodiment 12 or 13, wherein the selective removal of at least a portion of any one of the at least one ink materials, the template material, or any combination thereof results in a structure comprising the template material having channels, tunnels, internal cavities, or voids that are interconnected in one, two, or three dimensions within the structure.

Embodiment 15

The method of Embodiment 13 or 14, wherein at least one channel, tunnel, internal cavity, or void has at least one cross-sectional dimension in a range of from 100 nm to about 10 millimeter.

Embodiment 16

The method of any one of Embodiments 12 to 15, comprising selectively removing at least a portion of the template material.

Embodiment 17

The method of Embodiment 16, wherein the selective removal of at least a portion of any one of the at least one ink materials, the template material, or any combination thereof results in a shaped structure comprising at least one of the ink materials (either cured or uncured).

Embodiment 18

The method of any one of Embodiments 1 to 17, wherein at least one, and preferably all, of the ink materials, the template materials, or additives thereof are biocompatible.

Embodiment 19

The method of any one of Embodiments 1 to 18, wherein at least one, and preferably all, of the ink materials, the template materials, or additives thereof are suitable for implanting into a mammal, preferably a human.

Embodiment 20

An article comprising a structure prepared by the method of any one of Embodiments 1 to 19.

Embodiment 21

The article of Embodiment 20 that is a blood analyzer, micro-/nano-fluidic conduction or mixing device, reaction vessel, artificial/replacement tissue, tissue model, pump, balloon, sensor (e.g., for toxins/pathogens, biomarkers), filter, or cell culture platform.

Embodiment 22

The article of Embodiment 20 that is a shaped implantable tissue graft scaffolds, implantable cellular matrix, drug release reservoirs, model tissue, implantable gel for filling/bulking spaces energy storage devices, wound dressing, or sorption device.

EXAMPLES

The following Examples are provided to illustrate some of the concepts described within this disclosure. While each Example is considered to provide specific individual embodiments of the methods, materials, and equipment associated therewith, and in some cases expands the descriptions of the various embodiments described elsewhere, none of the Examples should be considered to limit the more general embodiments described herein.

Example 1

The present examples are described in terms of Ad/CD (hydro)gels that can be crosslinked via photopolymerization of methacrylate moieties. These are described schematically in FIG. 1 through FIG. 8. But again the methods and structures are not limited to these systems and the properties can be easily extrapolated to other systems of materials used in this method of 3-DP.

Working with a printer and a first version of custom designed extrusion hardware, structures have been printed having features on the orders of tens of microns. The resolution of any construct is ultimately going to be dependent on both hardware and materials; with the current materials system, resolution is limited primarily by the hardware that has been used. There is no intrinsic material limit to these feature sizes, and it is reasonably expected that features having dimensions less than 10 microns in size are achievable.

Example 2

Additional Comments

In considering broad uses of the technology: the printed and support materials can be modified or simply mixed with other materials, chemical components, or biological components, such as cells. Either the printed material or support material could be used as a removable vehicle to carry another material which has a means of stabilizing itself—for example, collagen might be mixed with either the printed gel or the support gel, allowed to crosslink by its own mechanisms, and then the supramolecular materials removed to leave a pure collagen gel. As another example, a photocrosslinkable polyethylene glycol (PEG) might be incorporated in a component of the supramolecular construct and then crosslinked, leaving a PEG gel, deposited by printing, once the supramolecular components were removed. Either the supramolecular support or printed material could conceivable contain an agent which would induce crosslinking in the other material. An agent could be immobilized on the polymeric backbone of a supramolecular ink which in turn might catalyze reactions that occur in the region where that ink was printed, for example using an enzyme to locally catalyze the polymerization of material. In short, this method potentially enables the printing of anything, anywhere, with the supramolecular components either participating or being eliminated from the final construct.

Example 3

Additional Comments Concerning Potential Commercial Uses and Applications

The inventive methods are applicable to any product capable of being created by additive manufacturing or application of 3-DP/additive manufacturing technology. Because the supramolecular material does not need to participate in the final structure, the method enables the 3-D patterning of a supramolecular construct that serves as a template for the formation a final structure.

Specifically with respect to bioprinting applications, the ability to print high-resolution gel constructs where components can be positioned in 3-D at will, including open channel-like structures, will enable the creation of scaffolds which might be implanted in patients to aid in tissue regeneration. By including cells within a construct during printing, high-resolution tissue-like constructs are possible. These constructs can be used to study cellular processes in highly defined 3-D environments, to create pseudo-tissues for drug screens or as models of healthy or diseased tissue, or to create functional tissue-like structures that can be implanted or perhaps used in external devices to augment or replace native tissue function. By including conductive elements within the construct, electrophysical applications might be possible—for example studies of neural circuits or the printing of flexible, 3-D electrode materials.

Example 4

(i) Material Syntheses

Sodium hyaluronate (HA, 90 kDa) was purchased from Lifecore (Chaska, Minn.). Unless otherwise noted, all other chemicals were purchased from Sigma-Aldrich. $^1$H-NMR spectra were acquired at 360 MHz (Bruker). Chemical shifts are reported relative to the solvent peak.

MeHA synthesis: Methacrylated HA (MeHA) was prepared by the esterification of the primary hydroxyl on N-acetyl-β-D-glucosamine residues with methacrylic anhydride (MA). Briefly, HA (5 g, 12.7 mmol, 1.0 eq) was dissolved in deionized water (350 mL) and stirred on ice. The pH was adjusted to 8.5 and MA (9.056 mL, 60.8 mmol, about 4.8 eq, about 20 eq relative to targeting modification) was added. The pH was maintained at pH 7.5-8.5 with addition of NaOH for 3 hours while stirring. The temperature was maintained at 4° C. overnight. The pH was returned to 7.5 the next day and the material was dialyzed and lyophilized $^1$H-NMR was used to determine a functionalization of ~25% from integration of the vinyl group ($\delta$=5.8, 1 H and $\delta$=6.25, 1H) with calibration to the HA backbone ($\delta$=3.20-4.20, 10H).

Tetrabutyl ammonium salt of hyaluronate formation: Tetrabutylammonium salts of HA (HA-TBA) and MeHA (MeHA-TBA), which are soluble in organic solvents, were prepared by dissolving either HA or MeHA in deionized water at 2.0 wt/v %. Dowex-100 resin was used for ion exchange, resulting in the acidified form of HA, which was neutralized by tetrabutylammonium hydroxide, frozen, and lyophilized.

CD-HA synthesis: HA was modified with β-cyclodextrin (CD-HA) as previously described. Briefly, 6-(6-aminohexyl) amino-6-deoxy-β-cyclodextrin (β-CD-HDA), an amine-functionalized cyclodextrin, was synthesized according to previous reports and conjugated to HA-TBA via anhydrous amidation in DMSO with (benzotriazol-1-yloxy)tris(dimethylamino)phosphonium hexafluorophosphate (BOP) as a coupling reagent. Quantities of reagents varied proportionally to the quantity of disaccharides in the HA-TBA used (1 eq), where 0.5 eq and 0.8 eq of each of β-CD-HDA and BOP were used for 25% and 40% modified HA, respectively. Purification was performed by extensive dialysis against deionized water, filtration to remove insoluble byproducts from the reaction, and lyophilization to yield the final product. Functionalization was determined by integration of the hexane linker ($\delta$=1.20-1.75, 12H), which was calibrated to the methyl singlet of HA ($\delta$=2.1, 3 H).

CD-MeHA synthesis: HA modified with both methacrylate and β-cyclodextrin moieties (CD-MeHA) was prepared by a procedure similar to that above. MeHA-TBA was used in place of HA-TBA as the base material. In $^1$H-NMR, the CD peaks obscured those of the HA backbone, so calibration was performed to the methyl peak of HA. CD functionalization was again determined by integration of the hexane linker ($\delta$=1.35-1.85, 12H).

Ad-HA synthesis: HA functionalized with adamantane (Ad-HA) was also prepared as previously reported. Anhydrous esterification of the HA-TBA disaccharide unit (1 eq) with 1-adamantane acetic acid (3 eq) was done in DMSO in the presence of 4-dimethylaminopyridine (DMAP; 1.5 eq) and di-tert-butyl dicarbonate (BOC$_2$O; 0.47 eq for 25% mod and 0.79 eq for 40% mod). The reaction proceeded for 24 hours at 45° C. A purified material was obtained by dialysis against deionized water, precipitation in acetone, further dialysis, and finally lyophilization. $^1$H-NMR was used to quantify functionalization by integration of the ethyl multiplet of adamantane ($\delta$=1.40-1.70, 12H), which was calibrated to the HA backbone ($\delta$=3.10-4.10, 10H).

Ad-MeHA synthesis: HA was modified with both methacrylates and adamantanes (Ad-MeHA) according to the procedure described above for the modification of HA with adamantane alone, but with MeHA-TBA as the base material. Modifications were determined as described for the synthesis of Ad-HA.

Fluorescent modification of HA-derivatives: To allow direct visualization of printed inks or support materials, methacrylated polymer components were fluorescently labeled via a fluorescent peptides. Peptides consisting of the sequence GCKKG-fluorophore were prepared through standard solid phase peptide synthesis (PS3 automated peptide synthesizer, Protein Technologies). Peptides were synthesized off a glycinol 2-chlorotrityl resin using FMOC protected amino acids (Novabiochem). The free acid of either 5(6)-carboxyfluorescein or rhodamine B was reacted to the amine terminus of the peptide by introducing and conjugating the fluorophore to the peptide as though it were a terminal amino acid. The peptide was cleaved from the resin with trifluoroacetic acid, triisopropyl silane, and water (95/2.5/2.5). It was then recovered from solution by precipitation from cold diethyl ether. MALDI-TOF mass spectrometry confirmed the formation of the desired peptide sequence (Applied Biosystems Voyager 6030). Spectrophotometry (Tecan infinite M200 spectrophotometer) was used to acquire absorbance and emission spectra from dilute aqueous solutions of the fluorescent peptides.

In order to couple a fluorescent peptide to adamantane-modified HA, the desired peptide (7.25 µmol, 0.04 eq) was dissolved in minimal deionized water and added dropwise to a solution of Ad-MeHA (75 mg, 0.2 mmol, 1 eq) dissolved in triethanolamine buffer (10 mL, pH 10). The reactions proceeded at room temperature for 2 hours, after which they were purified by dialysis and precipitation. Lyophilization yielded the final products.

(ii) (Hydro)Gel Formation (Hydro)gels were prepared by dissolution of the individual macromers in water or PBS at the desired concentration. For (hydro)gel formation by guest-host assembly, the two component solutions were combined and mixed to ensure a homogenous (hydro)gel. The (hydro)gel was then centrifuged to remove entrapped air. When including cells, one fifth of the final volume was reserved for resuspending a quantity of cells, as determined from counting using a hemocytometer, to yield the desired final cell concentration. One-half of the cell-containing volume was mixed with each component prior to combining to form a (hydro)gel. In all (hydro)gels, adamantane and β-cyclodextrin were present in equimolar concentration.

When either the ink or support (hydro)gel was methacrylated for covalent stabilization, both the Ad-HA and CD-HA macromers were methacrylated in that (hydro)gel. When a (hydro)gels were fluorescently labeled, only one third of the Ad-HA macromer mass used in the gel was labeled. The degree of modification of the labeled material was matched to the gel, so that the fluorescent material was 40% modified with adamantane if used in the support material, and 25% modified if used in the ink.

(iii) Live/Dead Staining

NIH 3T3 fibroblasts were encapsulated in gels at a concentration of 1 million cells per mL for cell viability studies. The cells were incorporated into gels and placed into syringes as described previously, filaments of materials containing cells were printed into support gels and placed in cell culture medium, and the constructs were incubated at 37° C. until analysis with a Live/Dead assay. A standard calcein AM/ethidium homodimer-1 Live/Dead kit (Life Technologies) was used according to manufacturer's protocol.

(iv) Printer Modification

A stepper motor-based extruder supplied with a 3D printer (X-Truder extruder and Revolution XL printer from Quintessential Universal Building Device, Inc.) was modified to drive a worm gear coupled to a lead screw, which actuated a syringe plunger via a 3D-printed coupling. A custom syringe extruder was coupled to the printer's thermoplastic extruder (FIG. 11A, dashed box and FIG. 11B). This modification, or similar, could be made to most commercially available or custom-built printers, simply by designing a syringe extruder to couple to hardware on hand. Images of the CAD model built are shown in FIG. 11C. The full custom assembly can be seen in the upper and lower images on the left side of FIG. 11C—the upper left image is a front view, approximately as seen in FIG. 11B, and the lower left image is a rear view. The colored components were custom built and printed, and the grey components represent parts that were purchased from commercial vendors (McMaster-Carr, Haydon Kerk Motion Solutions, SDP/SI, and MiSUMi). A simplified design could be achieved by mounting a NEMA 14 stepper motor to a printer's XY printhead carriage to directly drive the worm (described below), but this design aimed to avoid complete disassembly of the thermoplastic extruder by taking advantage of an option to couple the syringe extruder through an accessible gear on the X-truder's stepper motor shaft.

In FIG. 11C, the yellow component is the element that coupled the custom syringe extruder to the X-truder, which is driven by a NEMA 14 stepper motor. The blue and green are the front and back elements that together formed an open gear box. The assembly of these three components is seen in the upper right image, with the large grey circle in the foreground representing the gear that interfaced with the X-truder's gear. This gear drove a shaft that was mounted in a ball bearing (not shown) in the recess in the front gear box component (blue). A worm (not pictured) was mounted on this shaft and drove a worm gear (shown) mounted to a shaft that in turn was coupled (coupling not shown) to the vertical lead screw that extends out of the green component of the gear box. The lead screw was coupled to the syringe plunger actuation component (orange) by a flanged lead nut (not shown). The two orange components screw together to drive a syringe plunger as the lead nut moves along the lead screw. The lower right image shows, from below (as though looking up from the print surface), the components that assemble to hold the syringe. The two orange components screwed together around the lead nut and moved along the lead screw to actuate the plunger, while the red components held the shaft of the syringe. The needle protruded below through the hole seen in the lowest part of the red components. The red components were secured to the blue and green components of the gear box (as shown in the left two images). These components were printed using standard 3DP techniques: they were exported from Solidworks as STL files, processed into G-code by Slic3r, and printed using Repetier.

(v) Rheological Characterization: Rheological properties of the inks used were measured using an AR2000 rheometer (TA Instruments) with a 20 mm diameter cone and plate geometry (59 min 42 s cone angle, 27 μm gap). Oscillatory frequency sweeps (0.01-100 Hz; 1% strain), oscillations in applied strain (stepping between 1% and 250%, or between 1% and 250% strain at 10 Hz), and strain sweeps (0.006%-500%) at 0.1, 1.0, and 10 Hz were performed at 25° C.

(vi) Results

The development of a (hydro)gel-based 3DP approach permitted the printing of shear-thinning (hydro)gel "inks" directly into self-healing "support" (hydro)gels, where both (hydro)gels are based on supramolecular assembly through guest-host complexes. The direct writing of guest-host (hydro)gels ("GHost writing") was possible because of their noncovalent and reversible bonds that could be disrupted by application of a physical stimulus such as shear stress and that reform rapidly upon removal of the stimulus. Such properties permitted their use as injectable (hydro)gels, and consequently as inks in extrusion-based 3DP. These same properties enabled the use of a guest-host (hydro)gel as a support matrix, which deformed to accommodate extruded material and self-healed to maintain material localization. Importantly, the GHost writing printing the passage of the needle and stabilization of printed inks (FIGS. 15 and 17).

Importantly, the GHost writing printing platform was built on broadly accessible 3DP technology, including a commercially available 3D printer, standard 3DP software, and a modified stepper motor-driven thermoplastic extruder, which was adapted to drive the plunger of a syringe for material extrusion (FIG. 11).

Figure 12C:
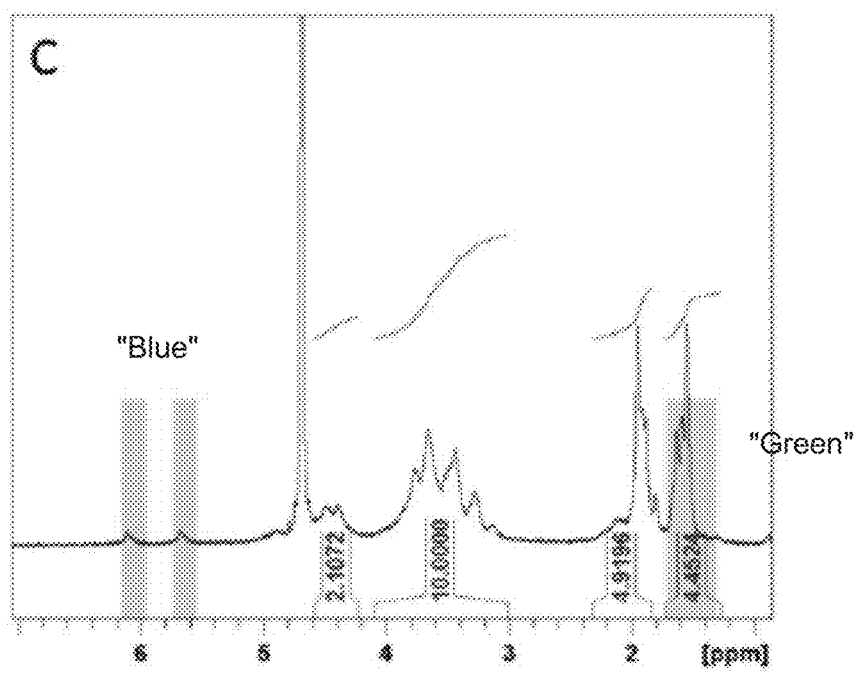
Figure 13C:
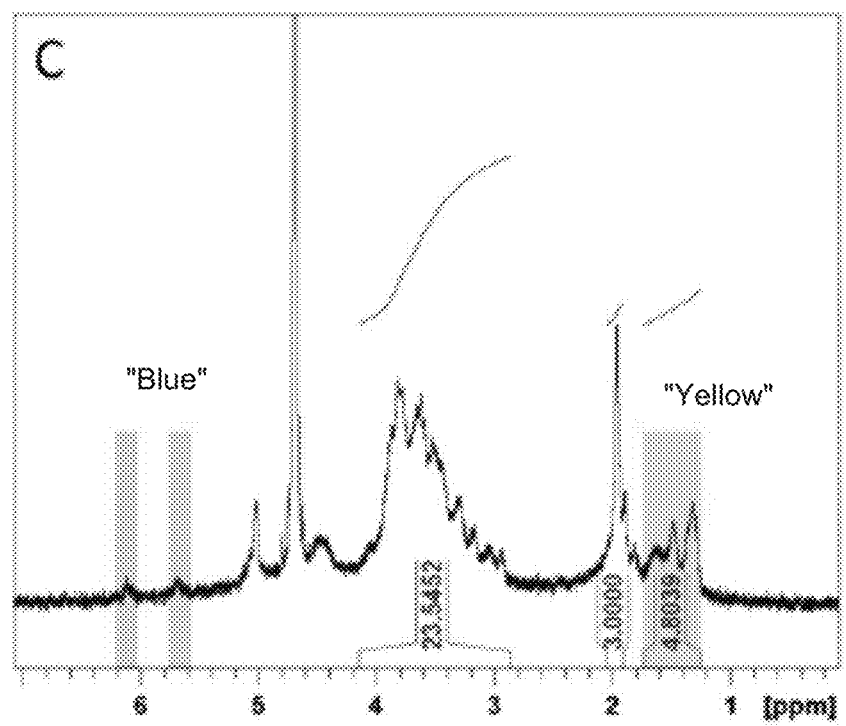

The supramolecular (hydro)gels used were based on modified HA, which was selected for its amenability to chemical modification and for its biocompatibility. Specifically, HA was modified with either adamantane (Ad) or β-cyclodextrin (β-CD) (Ad-HA and CD-HA, FIG. 11) and supramolecular assemblies rapidly formed upon mixing of Ad-HA and CD-HA through intermolecular guest-host bonds (between Ad and β-CD moieties). HA-based supramolecular (hydro)gel properties can be altered through modulation of the degree of modification of the HA backbone with the guest or host moiety (FIGS. 12(A-C) and 13(A-C)), through the concentration of material in the (hydro)gel, and through the ratio of guest-to-host moieties in the final gel. FIG. 12(A-C) show that integration of the ethyl multiplet of adamantine $-\delta=1.40$-$1.70$, 12 H (highlighted green)—gives the degree of modification relative to the HA backbone ($\delta=3.10$-$4.10$, 10 H). Methacrylate functionalization was determined from integration of the vinyl group in the methacrylate $-\delta=5.82$, 1 H and $\delta=6.25$, 1 H (highlighted blue)—relative to the HA backbone, and here was about 0.2. FIG. 13(A-C) shows that integration of the hexane linker $-\delta=1.20$-$1.75$, 12 H (highlighted gold)—gives the degree of modification relative to the methyl singlet of HA ($\delta=2.1$, 3 H). Methacrylate functionalization (highlighted blue) was assumed unchanged from original modification (ca. 0.2).

Figure 5:
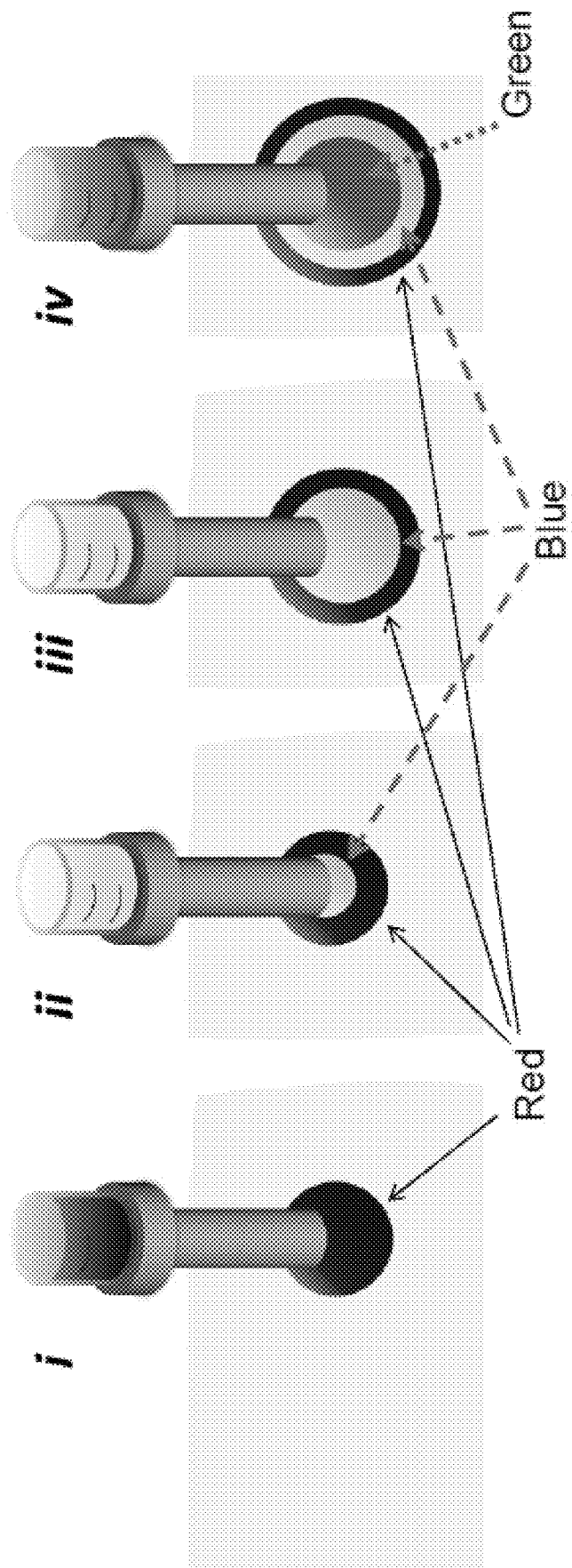
Figure 14:
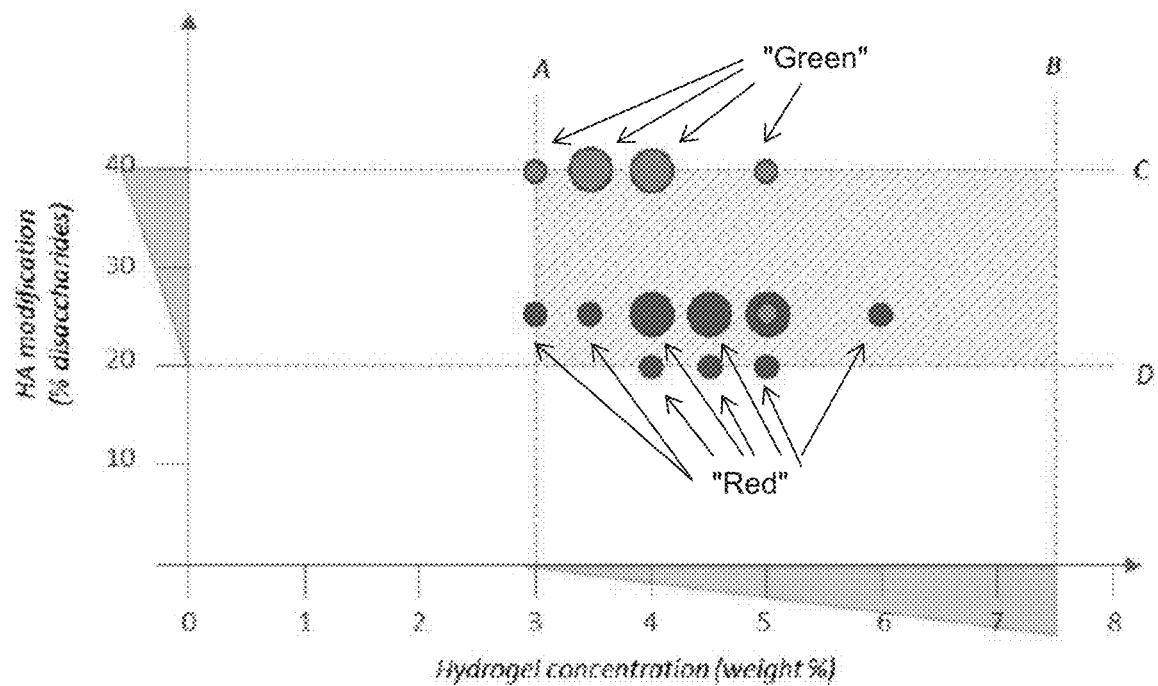
FIG. 14 is a diagram illustrating the explored ink and support (hydro)gel formulations, using guest-host (hydro) gels of the modification and concentrations indicated on the axes and a 1:1 ratio of CD:Ad within the (hydro)gels. Red dots represent ink formulations and green dots represent support gels. The hashed area represents a region in which useable (hydro)gels can be obtained. The larger dots indicate formulations that were deemed most useful, on the basis of printability and print fidelity.

Since the support (hydro)gel assemblies were self-healing, they deformed when a syringe needle was inserted to inject the (hydro)gel ink and rapidly healed around the printed ink (FIG. 5). Likewise, the printed ink retained the printed structure within the support gel (FIG. 5). Thus, the GHost writing process allowed the printing of supramolecular inks into any position within a 3D space initially occupied by the support gel. The (hydro)gel formulations used to demonstrate GHost writing were selected from many possible options (FIG. 14) that, based on the degree of polymer modification and concentration in solution, exhibit requisite dynamic bonding (FIGS. 15A and 15B) and shear-thinning and self-healing properties (FIGS. 15C and 15D). FIG. 14A illustrates that no gelation was observed below 3 wt/v % using HA derivatives with the degrees of modifications indicated. FIG. 14B illustrates that extrusion through a needle or movement of a needle through a support gel were limited to above 7.5 wt/v % due to high moduli, viscosity, and yield stress. FIG. 14C shows that higher degrees of modification are currently unexplored owing to polymer solubility and limited dynamic behaviors. FIG. 14D shows that limited gelation was observed below 20% modification.

For the extruded inks, Ad-HA and CD-HA were used with 25% of HA repeat units modified (Ad 25-HA and CD 25-HA) that were mixed at Ad:CD of 1:1 and at a total concentration of 5 wt/v %. FIGS. 15(A-B) show the frequency sweeps which indicate that increased polymer concentration or modification resulted in an increase in moduli and decrease in material relaxation. However, only increased modification (40%) resulted in materials that did not undergo observed bulk relaxation. FIG. 15C shows the shear-thinning behavior of all formulations through continuous flow experiments, illustrating reduced viscosity with increasing shear rate. FIG. 15D shows, correspondingly, that shear stress at high shear rates is mitigated by shear-thinning behavior. This property is essential towards identifying extruding inks (e.g., 25% modified, 5 wt/v %), which have lower maximum shear stress, and thus require less force to extrude.

This formulation provided viscoelastic properties that enabled extrusion through a variety of needle diameters and maintained print fidelity after dispensation into the support matrix (FIG. 16). FIG. 16A shows that, as with the support material, with increasing strain the loss modulus (G") begins to dominate over the elastic modulus (G'), indicating a transition from gel-like to fluid-like behavior necessary for ink extrusion. FIG. 16B shows that oscillating between low (1%) and high (250%) strain shows rapid material transition from gel-like to fluid-like behavior with rapid recovery, necessary for localization of extruded material.

Figure 17C:
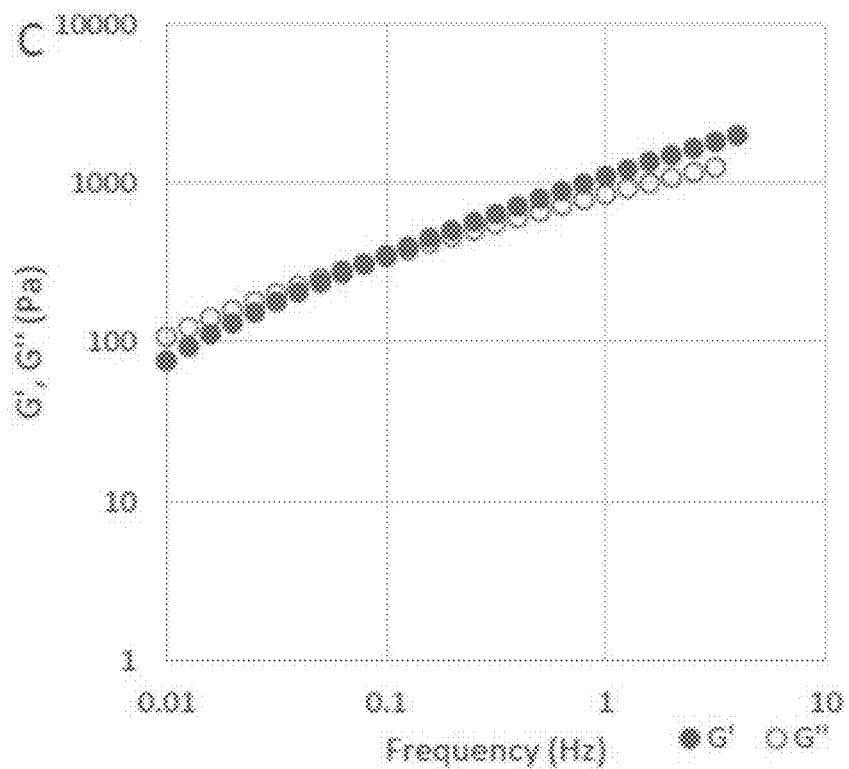

For the support gel, Ad-HA and CD-HA were used with 40% of the HA repeat units modified (Ad 40-HA and CD 40-HA) that were mixed at Ad:CD of 1:1 and at a total concentration of 4 wt/v %. Rheological examination (FIG. 15) demonstrates that increased polymer modification results in increased material stability (i.e., loss of bulk relaxation behavior). This formulation therefore provided a stable gel whose bulk resisted deformation from needle motion during printing, but still exhibited shear-yielding and self-healing properties (FIG. 17) that are essential for the passage of the needle and stabilization of printed inks (FIGS. 15 and 17). FIG. 17A shows that, with increasing strain, material properties (G', G") decrease the loss modulus (G") begins to dominate over the elastic modulus (G'), indicating a transition from gel-like to fluid-like behavior. FIG. 17B shows that oscillating between low (1%) and high (250%) strain shows rapid material transition from gel-like to fluid-like behavior with rapid recovery. FIG. 17C shows that, at low frequencies, material behavior becomes fluid-like, important in the use of this gel composition as a support material as it assists in allowing the needle to pass through the support.

Figure 3A:
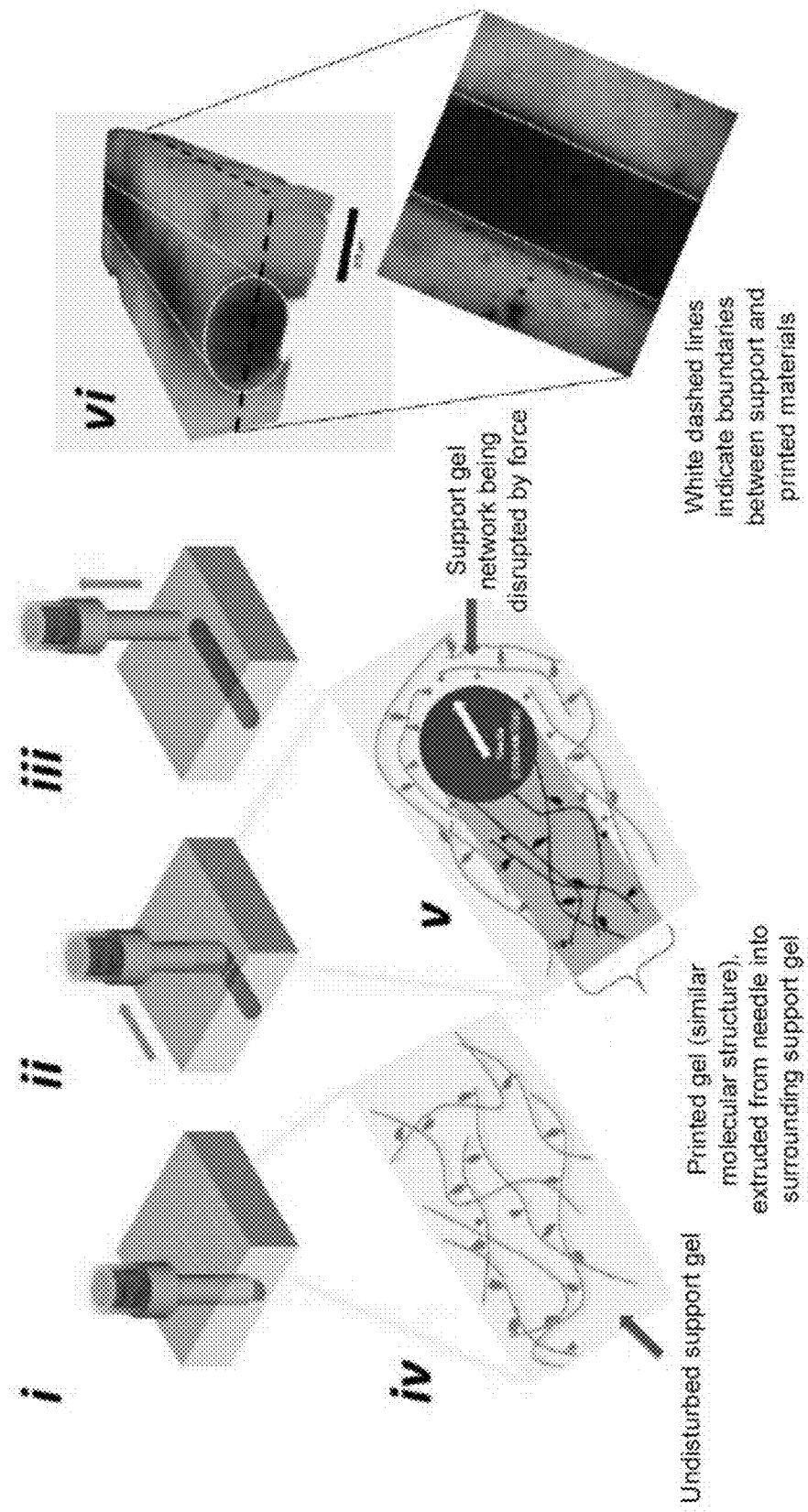
FIG. 3A illustrates an example of the printing of supramolecular ink into a supramolecular support. Either the support or ink can be used alone, but here the use of both is illustrated. i) Needle from which supramolecular ink will be extruded is inserted into a supramolecular (hydro)gel, whose bonds disrupt to allow insertion in response to the force exerted upon them by the needle. ii) Needle moves through the support (hydro)gel and deposits material. Bonds in the support material are disrupted by forces resulting from the needle motion and the addition of material into the (hydro)gel. Bonds within the ink are disrupted by shear forces applied during extrusion. iii) Removal of needle from the (hydro)gel. Bonds have reformed (and are dynamically reforming throughout the printing process), leaving stable structures behind. iv) Support (hydro)gel structure prior to disruption by needle motion. v) Top view of ink (shaded) deposition into support gel. As the needle moves in the direction of the arrow, bonds in the support (hydro)gel yield. Behind the needle where there is no more motion, bonds reform. The deposited ink also forms a supramolecularly stabilized network after extrusion has ceased. vi) A 3-D reconstruction of images of a fluorescently labeled ink printed into a fluorescently labeled support with an image of the midplane, showing no mixing of the ink and support.
Figure 3B:
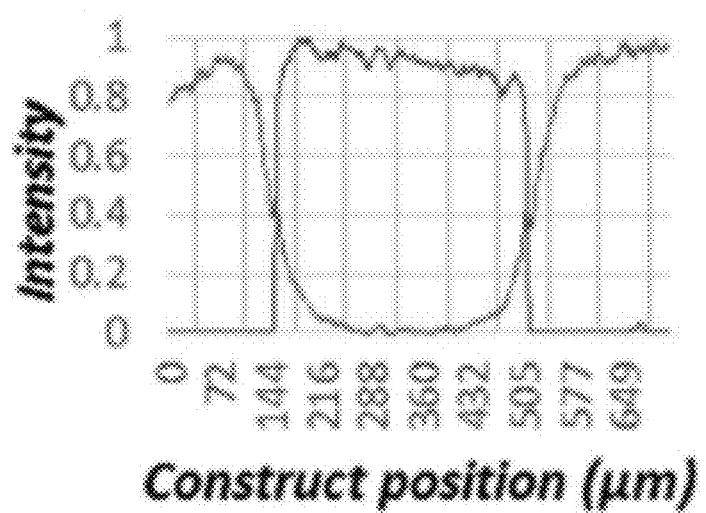
FIG. 3B is a graph illustrating the confocal cross-section and signal intensity profile, indication no mixing of printed ink with the support material.

For visualization, fluorescent labels were introduced onto the Ad-HA macromers by first modifying with methacrylate groups that could undergo a Michael addition reaction with thiol-modified fluorophores (i.e., rhodamine B for the ink and 5,6-carboxyfluorescein for the support gel). When the ink gel was printed into the support gel, confocal microscopy clearly showed distinct regions of the two gels with no mixing at the interface (FIG. 3). To control the dimensions of the printed structure, a constant speed of needle motion was maintained and the needle diameter and extrusion rate was varied such that the volume of material that flowed out of the needle scaled with the diameter. Linear supramolecular filaments (FIG. 2A) with diameters including 950, 370, and 35 µm were printed using 20, 27, and 34 gauge needles, respectively. A single needle could also be used deposit filaments of various diameters by adjusting the volume of gel extruded per unit distance traveled (FIG. 19), as allowed by the printer hardware and the physical properties of the gels.

Figure 4:
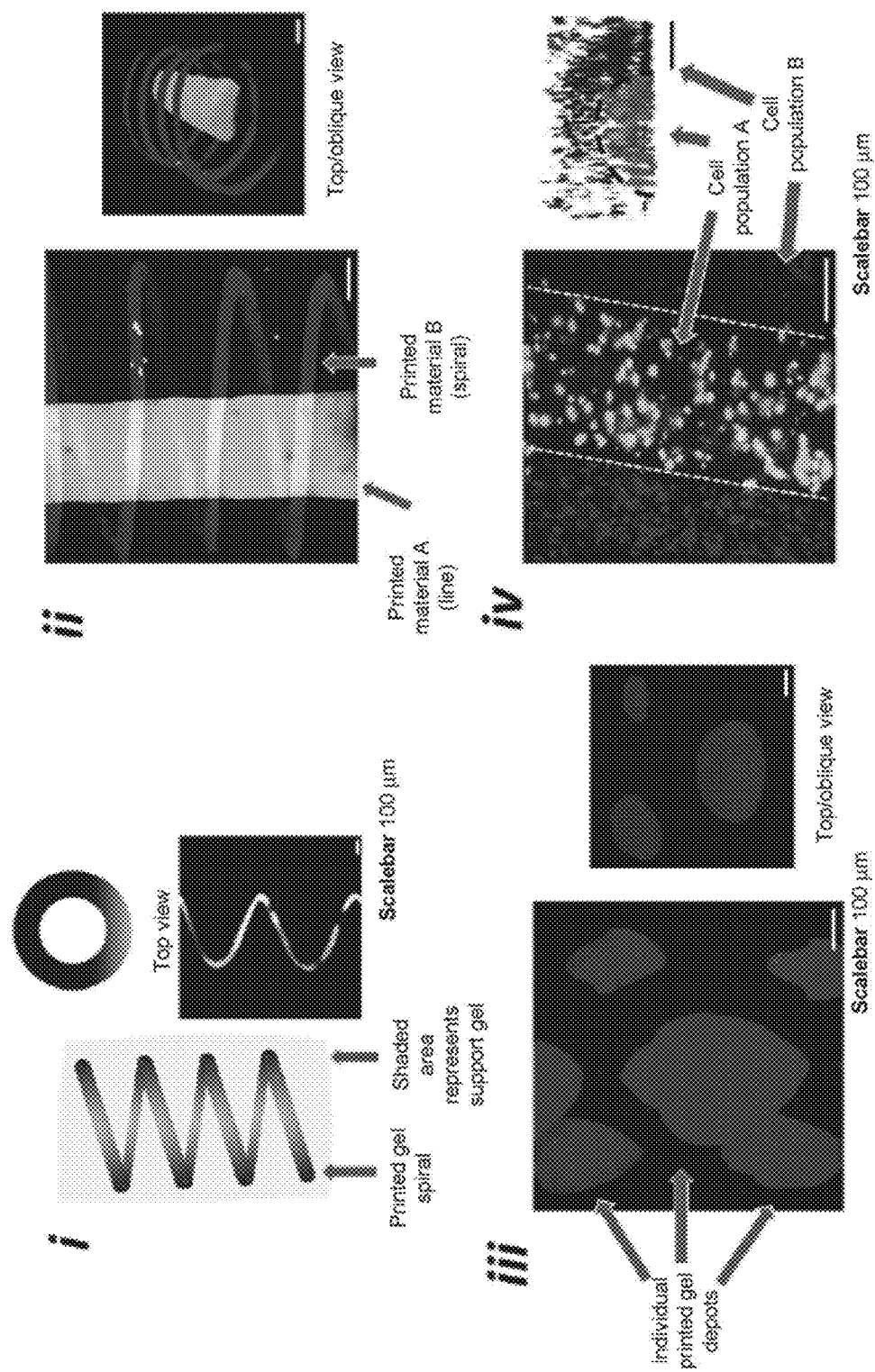
FIG. 4 illustrates several printed structures enabled by this printing method. i) A schematic of a spiral printed into a support (hydro)gel, with a 3D reconstruction of a fluorescently-labeled ink spiral printed into a support gel (not fluorescent, shaded or black). ii) An image of the structuring of two materials printed relative to one another in the same (hydro)gel. Here, one ink (material A, line) was surrounded by a second material (material B, spiral), which was printed in a spiraling pattern around the first. iii) Unattached depots of material were printed into arbitrary space relative to one another. These depots were of varying sizes and arranged such that their midpoints were equidistant from the center of a circle, as illustrated in the top view. iv) One cell population A was printed into another B to illustrate the ability to pattern multiple cell types in 3-D space, just as the inks might be printed. This figure illustrates how ink compositions could be varied, so that the structures printed might include any number of chemical or biological features printed anywhere in 3-D space.
Figure 20:
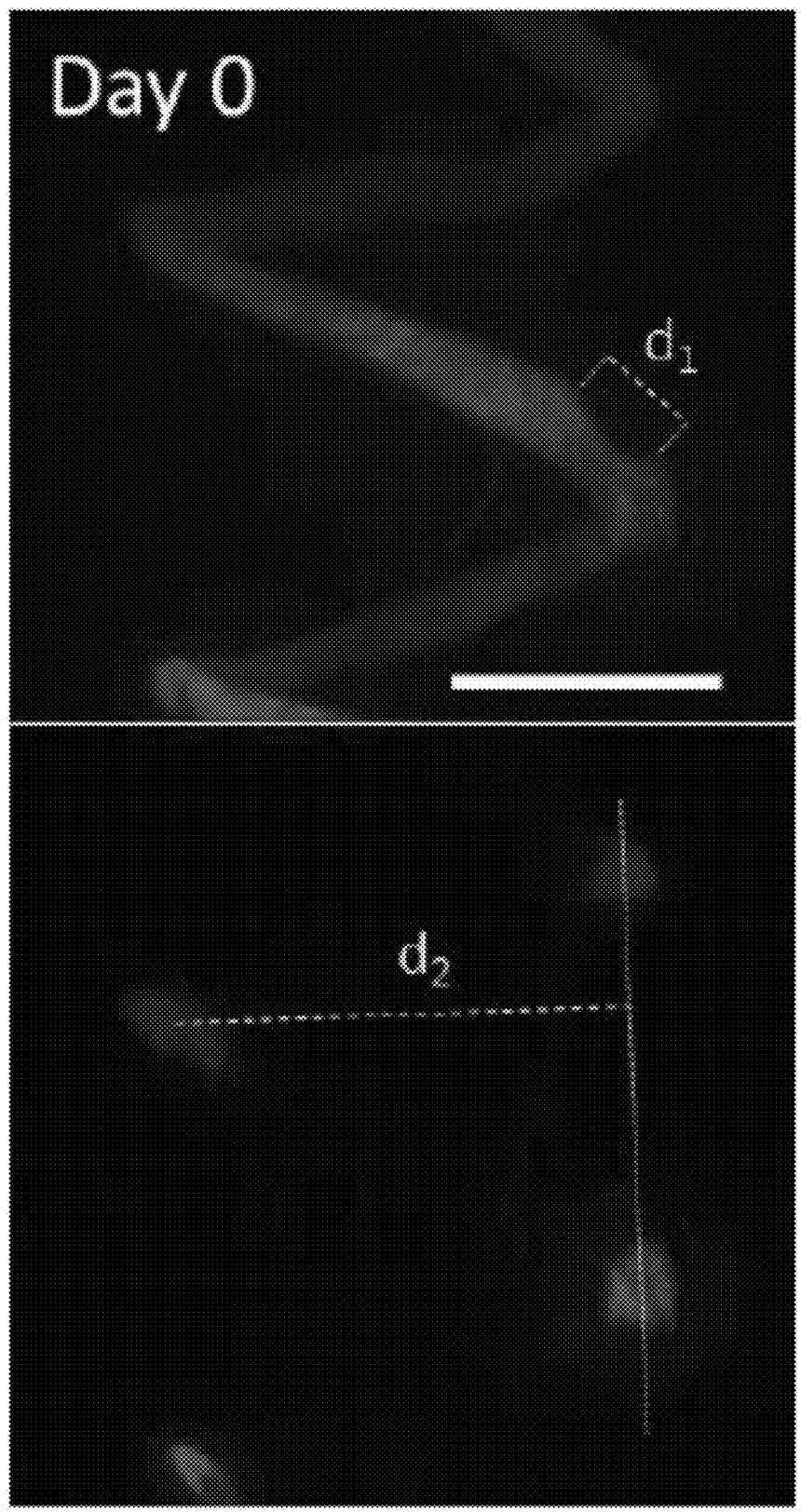
FIG. 20 are images illustrating the stability of a spiral structure printed into a support gel over one week. Both the support and ink gels are networks crosslinked only by supramolecular bonds (support: 40% modified CD-HA and Ad-HA, guest:host ratio of 1:1, and 4 wt/v % (hydro)gel concentration; ink: 25% modified CD-HA and Ad-HA, guest:host ratio of 1:1, and 5 wt/v % (hydro)gel concentration). Measurements of a small defect in the printed gel (d1) and spiral diameter (d2) remain constant over seven days, indicating no measurable evolution of the printed structure. Tilt along the z-axis creates variation in z-repeat distance between the Day 0 and 7 images. Scalebars: 500 µm.
Figure 20:
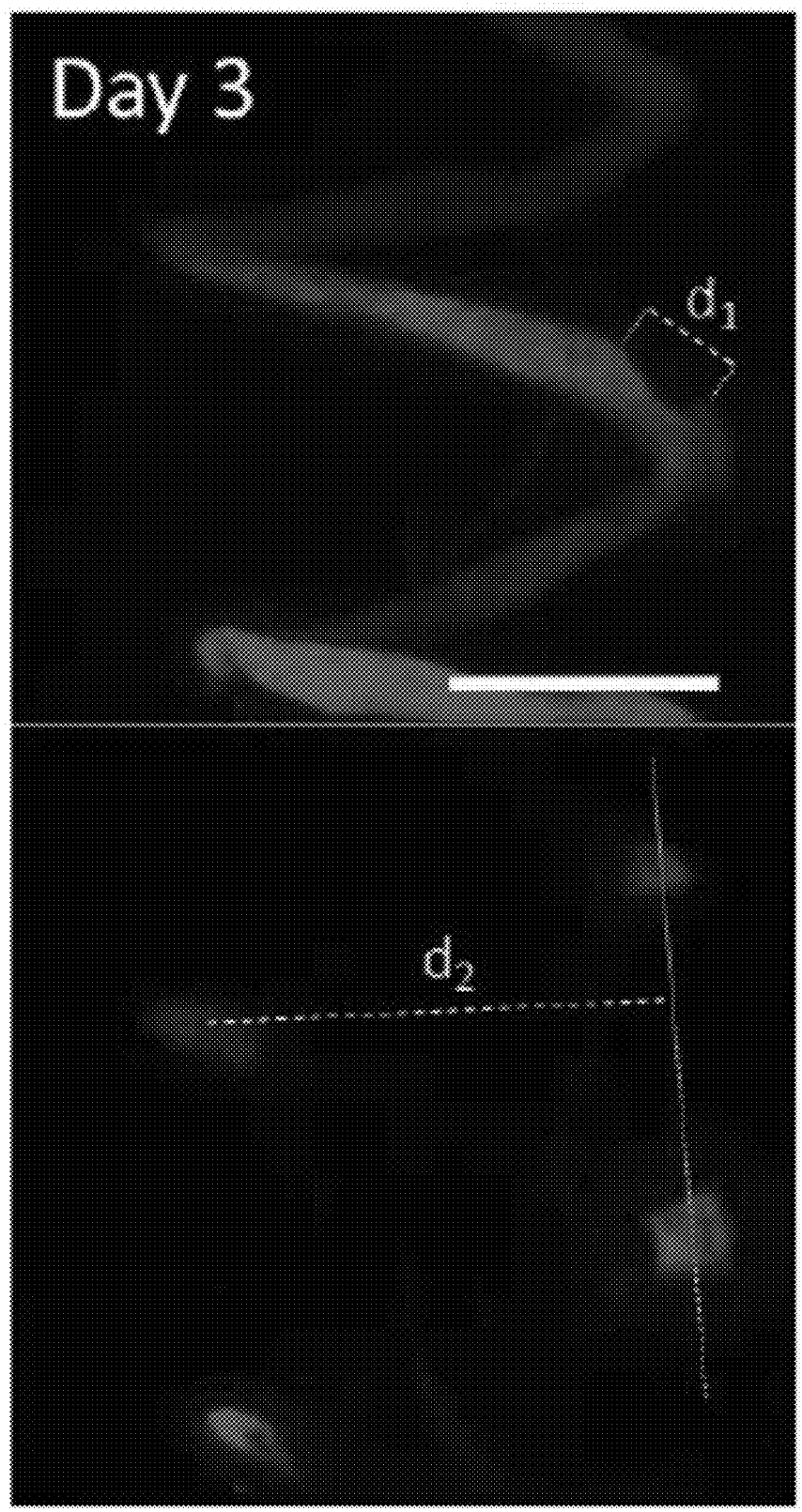
Figure 20:
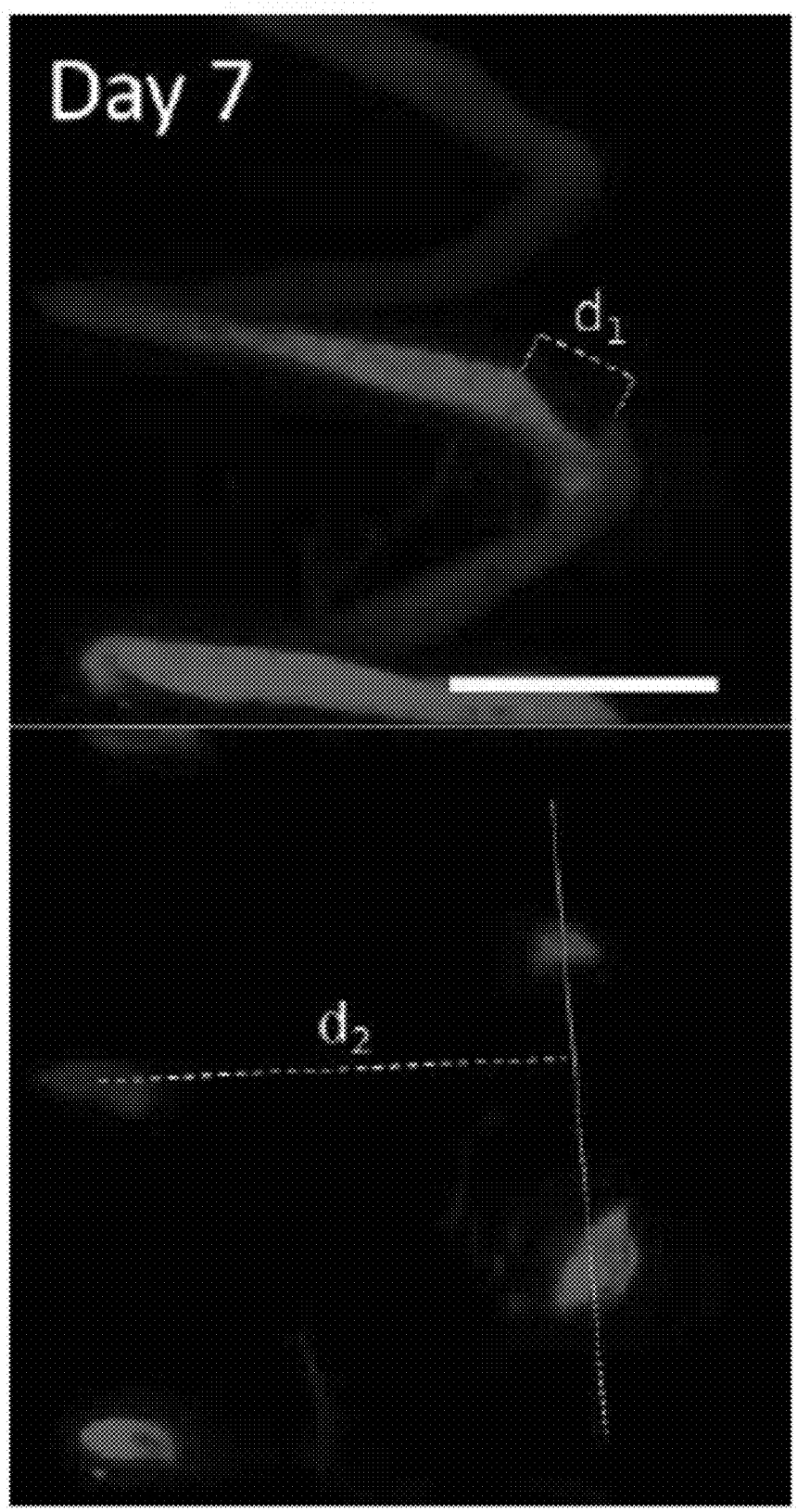

GHost writing enabled 3D structuring of materials in a manner that is not possible using standard printing methods that layer material atop previously deposited materials. Since the space contained a support matrix, as opposed to air, printing could be performed continuously in any direction in 3D space. This was illustrated by the printing of a spiral structure into a support (hydro)gel (FIG. 4). Likewise, it was possible to print multiple inks and structures into the same support gel, as illustrated by the printing of both a filament and a spiral structure into the same material (FIG. 4). Once printed, supramolecular crosslinking maintained stable (hydro)gel structures over the course of several days (FIG. 20).

With GHost writing, patterns were not limited to (hydro) gels deposited along the path of the needles, but could also include discrete volumes, or pockets, of material deposited at a point in 3D space where the needle is positioned during an extrusion without X, Y, or Z translation (FIG. 4). A series of material pockets of three different sizes was printed in a spiraling arrangement, where the material was only extruded when the needle was stationary. The average volumes of the regions were calculated from z-stack confocal images, and were found to be about 13 nL, 30 nL, and 106 nL for each of the three depot sizes, scaling with the programmed volumes of material specified for extrusion. This method of extruding materials into depots could allow the patterning of cell pockets or sources of concentrated materials that might diffuse from that source to establish a gradient within the (hydro)gel.

Figure 21:
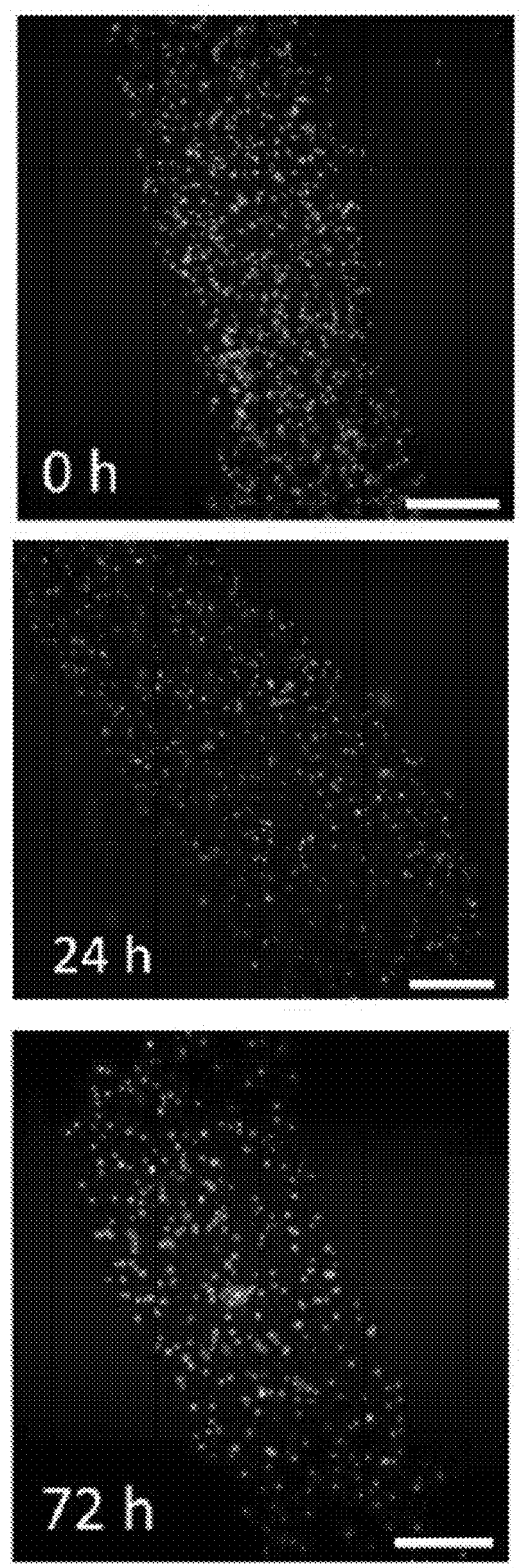
FIG. 21 are images illustrating the viability of 3T3 fibroblasts within printed filaments (Ad25-HA/CD25-HA supramolecular (hydro)gel) as measured with Live/Dead staining immediately after printing, and after 24 or 72 hours of culture. Scalebars: 500 µm.
Figure 21:
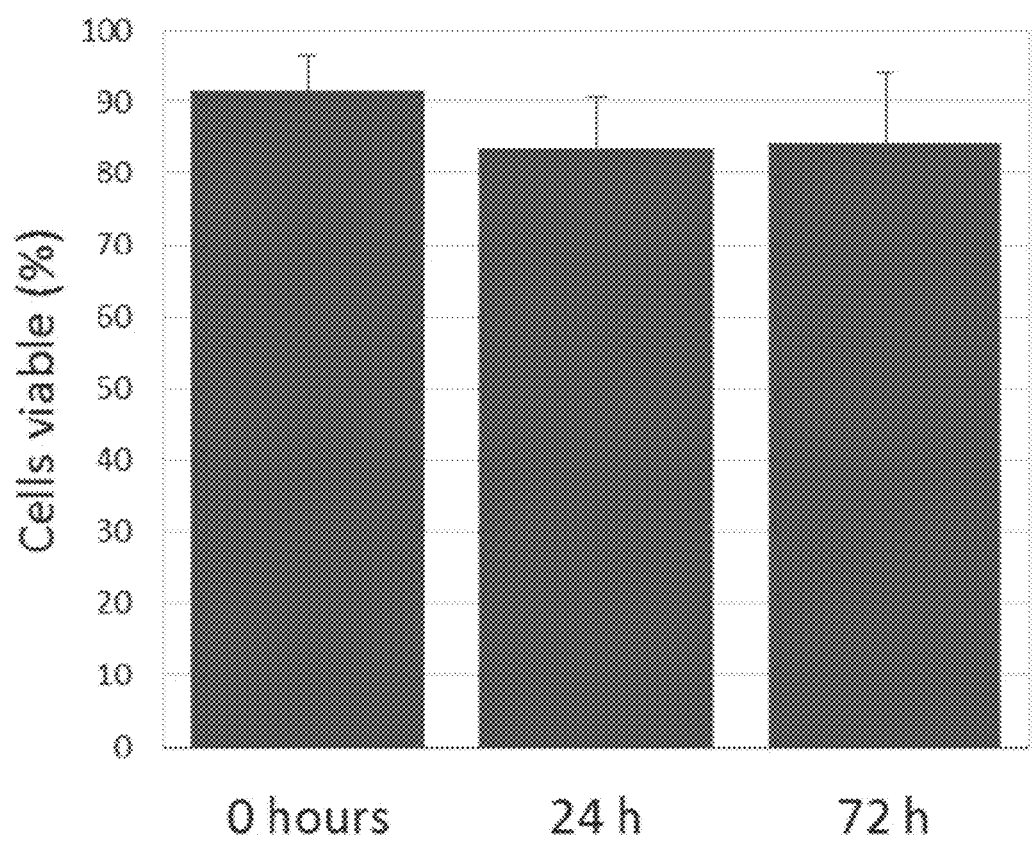

Multicellular structures were also patterned using the Ghost writing process by incorporating cells into the support gel, the printed material, or both. Labeling a population of mesenchymal stem cells (MSCs) with a green CellTracker dye and a population of 3T3 fibroblasts (3T3s) with a red CellTracker dye permitted visualizing distinct populations of cells after printing an MSC-containing ink into a 3T3-containing support (FIG. 4). The MSCs were localized to regions into which they were printed, and were surrounded in 3D space by the second cell population of 3T3s. The inclusion of cells does not affect the printing process, beyond requiring printing under standard sterile culture conditions if the cellular constructs are to be maintained. The printing process was also nontoxic to cells (>90% viable) and there was minimal loss in viability observed over several days in culture (FIG. 21). Such results are not surprising, as the potential cell-protective capacity of shear-thinning (hydro)gels for injection has been previously established, and the materials display characteristic shear-thinning behaviors (FIG. 15).

The dynamic bonds used in the support and ink gels enabled the shear-thinning and self-healing properties central to Ghost writing, but may lack mechanical properties necessary for longterm stability or perfusion. However, the gels can be designed to have a secondary, covalent crosslinking mechanism (e.g., light-mediated crosslinking) in either the ink or support materials to selectively stabilize against physical or chemical perturbations. This secondary stabilization was utilized within either the support or printed materials to design voids or freestanding 3D structures, respectively, by removal of the unstabilized gels. This approach can be used to introduce channels for applications in cellular constructs whose dimensions exceed more than a couple hundred micrometers and require perfusion to facilitate both the convection of nutrients throughout the construct and the removal of metabolic waste.

Figure 7:
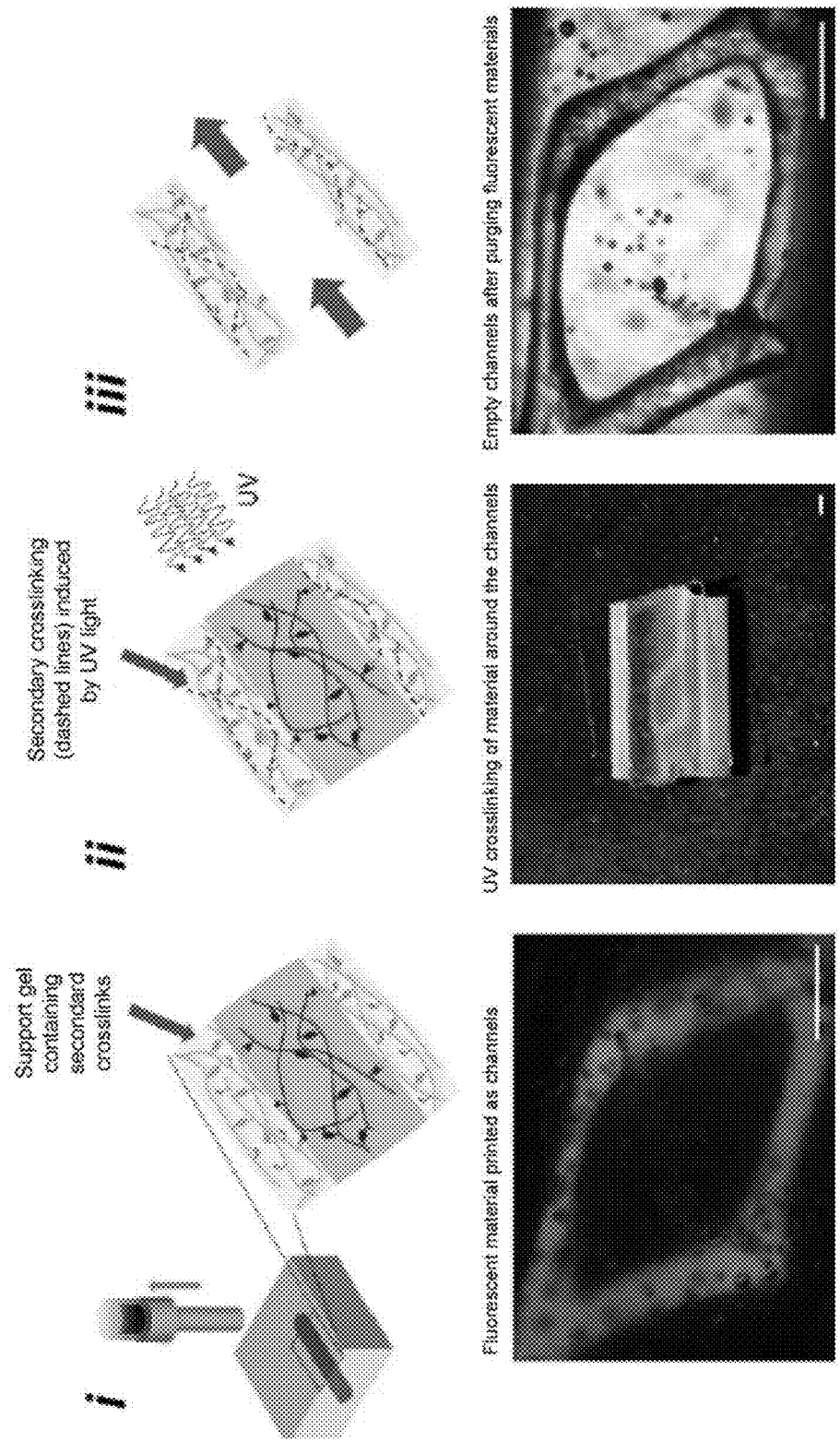
Figure 8:
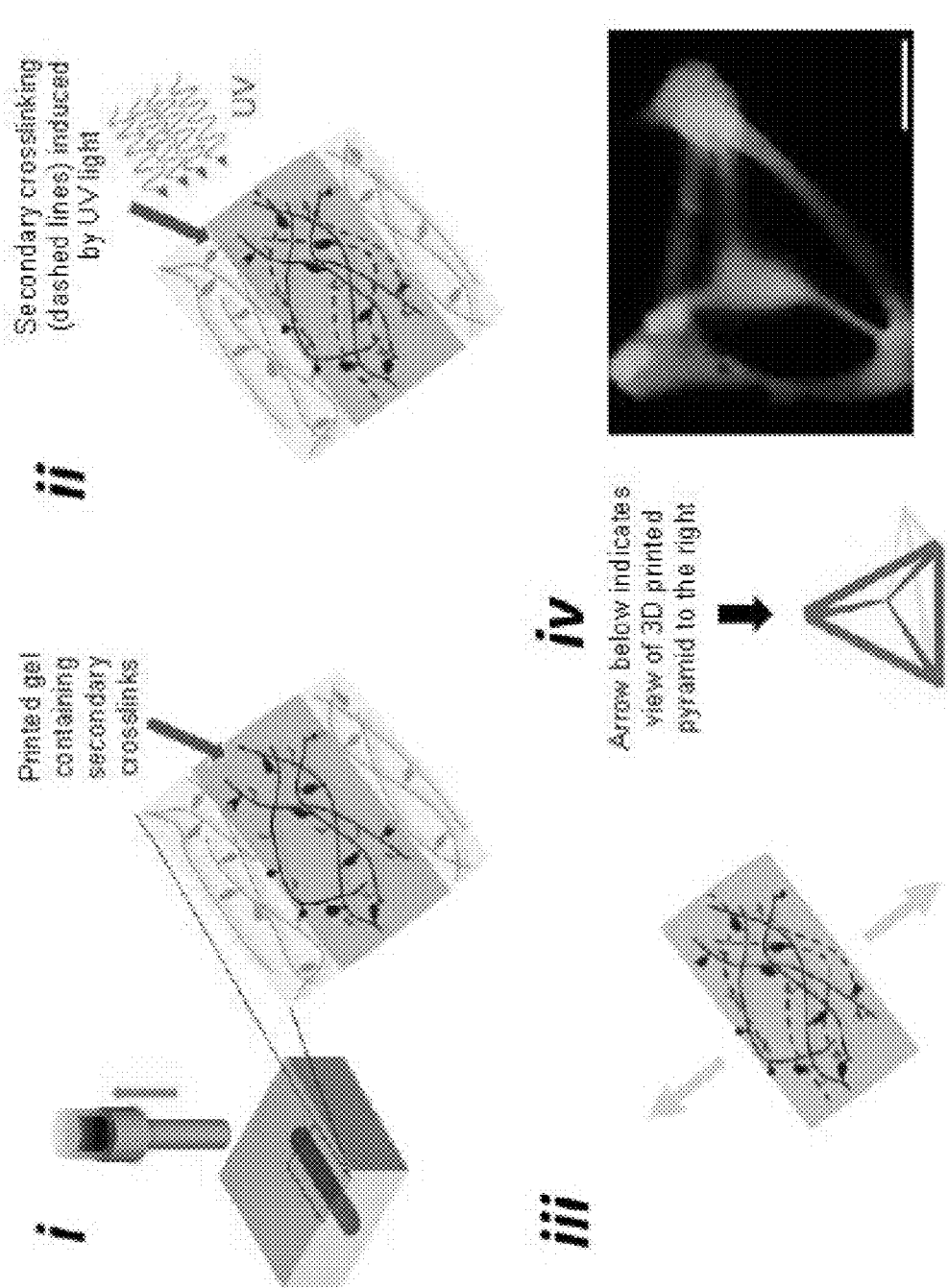

To accomplish this, methacrylates (≈20% of repeat units) were introduced into the HA macromers which were then modified with either Ad or CD moieties. This yielded materials (Ad-MeHA and CD-MeHA, FIGS. 2 and 6) that formed (hydro)gel networks through both supramolecular bonding (to enable GHost writing) and covalent crosslinking (for mechanical stabilization), induced by photopolymerization in the presence of UV light and a radical generating photoinitiator. The photocrosslinking of methacrylate modified materials has been used extensively for the encapsulation of viable cells within (hydro)gels. Importantly, such secondary modification, including by methacrylates, does not affect the guest-host (hydro)gel properties prior to inducing covalent crosslinking. Following photopolymerization, an increase in the storage modulus was observed and dynamic material behaviors ceased (FIG. 22). As before, shear-thinning (hydro)gel inks were printed into self-healing support (hydro)gels, where the support gels contained methacrylate groups (FIG. 7). After printing a bifurcating and rejoining structure of the fugitive ink, the constructs were exposed to UV light to stabilize the support gel. The printed ink was then removed by flow applied through needles inserted into the gel in the inlet and outlet of the channel structure, leaving behind an open channel with the printed pattern and dimensions. These channels were perfusable with fluid (FIG. 7).

As another illustration of the versatility of the printing platform, inks capable of secondary, covalent crosslinking were printed into support gels that did not undergo stabilization. A pyramidal (hydro)gel (FIG. 8) composed of six filaments with an average diameter of 260 μm that joined at four vertices was printed within a support gel. After exposure to light, the support gel was washed away by disrupting guest-host bonds with a solution containing excess β-CD, which competes with CD-HA to bind with Ad-HA, causing dissociation of any (hydro)gel not stabilized by covalent bonds.

The application of supramolecular (hydro)gels to 3D bioprinting, as both an ink and support matrix, allows the specification and printing of diverse (hydro)gel structures—materials, voids, and cells—at high resolution, anywhere in the 3D space of the construct. (Hydro)gels that exemplify the necessary material properties for this approach are illustrated here; however, there are numerous (hydro)gels that may be amenable to the technique. The dynamic nature of the guest-host crosslinking that permits both shear-thinning and self-healing properties is central to this approach. This new technique opens up many opportunities in 3DP, including the printing of multiple materials and complex structures at high resolutions, as well as the formation of free-standing structures or constructs that have open channels. Further development of supramolecular gels for inks and supports, expansion of secondary crosslinking mechanisms, and refinement of printing hardware would enable increasing complexity and functionality to be designed into supramolecular 3DP systems. In the rapidly growing field of additive manufacturing, and bioprinting specifically, Ghost writing-type systems may facilitate the printing of complex (hydro)gel structures whose chemical and cellular compositions can be controlled at increasingly high resolutions.

The following references may be useful in understanding some elements of the present invention or background principles thereof 1. Wu, W, A J DeConinck, and J A Lewis. 2011. "Omnidirectional Printing Of 3D Microvascular Networks." Advanced Materials 23: H178-H183.
2. Kolesky, D B, R L Truby, A S Gladman, T A Busbee, K A Homan, and J A Lewis. 2014. "3D Bioprinting Of Vascularized, Heterogeneous Cell-Laden Tissue Constructs." Advanced Materials 26: 3124-3130
3. Pataky, K., Braschler, T., Negro, A., Renaud, P., Lutolf, M. P. and Brugger, J. (2012), Microdrop Printing of Hydrogel Bioinks into 3D Tissue-Like Geometries. Adv. Mater., 24: 391-396.
4. L. A. Hockaday, K. H. Kang, N. W. Colangelo, P. Y. C. Cheung, B. Duan, E. Malone, J. Wu, L. N. Girardi, L. J. Bonassar, H. Lipson, C. C. Chu, J. T. Butcher, Biofabrication 2012, 4, 035005.
5. C. Ladd, J.-H. So, J. Muth, M. D. Dickey, Adv. Mater. 2013, 25, 5081.
6. F. J. Tölle, M. Fabritius, R. Mülhaupt, Adv. Funct. Mater. 2012, 22, 1136.
7. Y. L. Kong, I. A. Tamargo, H. Kim, B. N. Johnson, M. K. Gupta, T. W. Koh, H. A. Chin, D. A. Steingart, B. P. Rand, M. C. McAlpine, Nano Lett. 2014, 14, 7017.
8. B. G. Compton, J. A. Lewis, Adv. Mater. 2014, 26, 5930.
9. B. M. Wu, S. W. Borland, R. A. Giordano, L. G. Cima, E. M. Sachs, M. J. Cima, J. Controlled Release 1996, 40, 77.
10. V. Mironov, T. Boland, T. Trusk, G. Forgacs, R. R. Markwald, Trends Biotechnol. 2003, 21, 157.
11. B. Derby, Science 2012, 338, 921.
12. J. Malda, J. Visser, F. P. Melchels, T. Jungst, W. E. Hennink, W. J. Dhert, J. Groll, D. W. Hutmacher, Adv. Mater. 2013, 25, 5011.
13. S. V. Murphy, A. Atala, Nat. Biotechnol. 2014, 32, 773.
14. M. C. Cushing, K. S. Anseth, Science 2007, 316, 1133.
15. M. Guvendiren, J. A. Burdick, Curr. Opin. Biotechnol. 2013, 24, 841.
16. T. Boland, X. Tao, B. J. Damon, B. Manley, P. Kesari, S. Jalota, S. Bhaduri, Mater. Sci. Eng., C 2007, 27, 372.
17. X. F. Cui, K. Breitenkamp, M. G. Finn, M. Lotz, D. D. D'Lima, Tissue Eng., Part A 2012, 18, 1304.
18. T. Xu, W. X. Zhao, J. M. Zhu, M. Z. Albanna, J. J. Yoo, A. Atala, Biomaterials 2013, 34, 130.
19. V. Jetze, P. Benjamin, J. B. Thijs, B. Jelle, J. A. D. Wouter, P. W. M. Ferry, M. Jos, Biofabrication 2013, 5, 035007.
20. X. Wang, Y. Yan, Y. Pan, Z. Xiong, H. Liu, J. Cheng, F. Liu, F. Lin, R. Wu, R. Zhang, Q. Lu, Tissue Eng. 2006, 12, 83.
21. A. Skardal, J. Zhang, L. McCoard, X. Xu, S. Oottamasathien, G. D. Prestwich, Tissue Eng., Part A 2010, 16, 2675.
22. A. L. Rutz, K. E. Hyland, A. E. Jakus, W. R. Burghardt, R. N. Shah, Adv. Mater. 2015, 27, 1607.
23. F. Pati, J. Jang, D. H. Ha, S. Won Kim, J. W. Rhie, J. H. Shim, D. H. Kim, D. W. Cho, Nat. Commun 2014, 5, 3935.
24. S. E. Bakarich, M. I. H. Panhuis, S. Beirne, G. G. Wallace, G. M. Spinks, J. Mater. Chem. B 2013, 1, 4939.
25. C. Li, A. Faulkner-Jones, A. R. Dun, J. Jin, P. Chen, Y. Xing, Z. Yang, Z. Li, W. Shu, D. Liu, R. R. Duncan, Angew. Chem. Int. Ed. 2015, 54, 3957.
26. E. A. Appel, J. del Barrio, X. J. Loh, O. A. Scherman, Chem. Soc. Rev. 2012, 41, 6195.
27. M. Guvendiren, H. D. Lu, J. A. Burdick, Soft Matter 2012, 8, 260.
28. b) S. Seiffert, J. Sprakel, Chem. Soc. Rev. 2012, 41, 909.
29. J. A. Burdick, G. D. Prestwich, Adv. Mater. 2011, 23, H41.

30. C. B. Rodell, A. L. Kaminski, J. A. Burdick, Biomacromolecules 2013, 14, 4125.
31. C. Yan, M. E. Mackay, K. Czymmek, R. P. Nagarkar, J. P. Schneider, D. J. Pochan, Langmuir 2012, 28, 6076.
32. B. A. Aguado, W. Mulyasasmita, J. Su, K. J. Lampe, S. C. Heilshorn, Tissue Eng., Part A 2012, 18, 806.
33. H. D. Lu, D. E. Soranno, C. B. Rodell, I. L. Kim, J A Burdick, Adv. Healthcare Mater. 2013, 2, 1028.
34. C. B. Rodell, J. W. MacArthur, S. M. Dorsey, R. J. Wade, L. L. Wang, Y. J. Woo, J. A. Burdick, Adv. Funct. Mater. 2015, 25, 636.
35. M. Radisic, L. Yang, J. Boublik, R. J. Cohen, R. Langer, L. E. Freed, G. Vunjak-Novakovic, Am. J. Physiol.: Heart Circ. Physiol. 2004, 286, H507.
36. N. W. Choi, M. Cabodi, B. Held, J. P. Gleghorn, L. J. Bonassar, A. D. Stroock, Nat. Mater. 2007, 6, 908.
37. A. P. Golden, J. Tien, Lab Chip 2007, 7, 720
38. J. S. Miller, K. R. Stevens, M. T. Yang, B. M. Baker, D. H. Nguyen, D. M. Cohen, E. Toro, A. A. Chen, A. Galie, X. Yu, R. Chaturvedi, S. N. Bhatia, C. S. Chen, Nat. Mater. 2012, 11, 768.
39. K. T. Nguyen, J. L. West, Biomaterials 2002, 23, 4307.
40. J. L. Ifkovits, J. A. Burdick, Tissue Eng. 2007, 13, 2369.
41. S. Sahoo, C. Chung, S. Khetan, J. A. Burdick, Biomacromolecules 2008, 9, 1088.
42. K. A. Smeds, M. W. Grinstaff, J. Biomed. Mater. Res. 2001, 54, 115.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A method of manufacturing a three-dimensional (3-D) structure comprising channels, tunnels, internal cavities or voids, said method comprising:
   delivering a volume of a first ink material into a volume of at least one template material thereby forming a two- or three dimensional patterned volume of the first ink material within the volume of the at least one template material, the at least one template material comprising a self-healing supramolecular gel capable of maintaining the shape and dimensional stability of the two- or three dimensional pattern of the delivered volume of the first ink material; and
   selectively removing at least a portion of the first ink material from the volume of the at least one template material so as to provide the 3-D structure comprising channels, tunnels, internal cavities or voids.

2. The method of claim 1, further comprising delivering a volume of a second ink material and optionally subsequent volumes of subsequent ink materials (a) into the volume of the at least one template material; (b) into a volume of at least one of an earlier delivered ink material, or (c) into both the volume of the at least one template material and a volume of at least one of an earlier delivered ink material, thereby forming a two- or three dimensional patterned volume of the second and optional subsequent ink materials, the at least one template material comprising a self-healing supramolecular gel capable of maintaining the shape and dimensional stability of a two- or three dimensional pattern of all the delivered volumes of the ink materials.

3. The method of claim 2, wherein one or more of the first ink material, second ink material, or optional subsequent ink materials comprise a supramolecular gel that is compositionally different than the supramolecular gel of at least one template material.

4. The method of claim 3, wherein one or more of the first ink material, second ink material, or optional subsequent ink materials is compositionally different from the each of the other ink materials.

5. The method of claim 1, wherein the first ink material is delivered by injection into the volume of the at least one template material.

6. The method of claim 1, wherein the first ink material is injected using a needle, cannula, catheter, or tubing.

7. The method of claim 1, wherein the first ink material is a shear thinning material that sets to a solid or semi-solid upon delivery into a volume of an earlier delivered ink material or the volume of the at least one template material.

8. The method of claim 1, wherein the first ink material, the at least one template material, or any combination thereof independently comprise a pharmaceutically active drug or neutraceutical; a population of cells; a peptide or peptide derivative; one or more types of nanoparticles or quantum dots; a fluorescent or phosphorescent material; a magnetic material; or a combination thereof.

9. The method of claim 1, wherein the first ink material, the at least one template material, or any combination thereof independently comprise a settable, shear-thinning self-healing supramolecular gel comprising a polymer network, said polymer network comprising non-covalent crosslinks and at least one set of chemical moieties being capable of participating in at least one chemical covalent cross-linking reaction.

10. The method of claim 1, wherein said at least one template material is a shear-thinning self-healing supramolecular gel comprising hyaluronic acid.

11. The method of claim 1, wherein the at least one template material is a shear-thinning self-healing supramolecular gel comprising methacrylated hyaluronic acid, hyaluronic acid functionalized with methacrylate and β-cyclodextrin, hyaluronic acid functionalized with methacrylate and adamantane, or a combination thereof, tetrabutyl ammonium salt of hyaluronic acid, or tetrabutyl salt of methacrylated hyaluronic acid.

12. The method of claim 1, wherein the first ink material, the at least one template material, or any combination thereof independently comprise a settable, shear-thinning (hydro)gel comprising a hydrophilic polymer network, said hydrophilic polymer network comprising non-covalent crosslinks and at least one set of chemical moieties being capable of participating in at least one chemical covalent cross-linking reaction.

13. The method of claim 12, further comprising independently triggering at least one chemical covalent crosslinking reaction within the first ink material, the at least one template material, or combination thereof.

14. The method of claim 1, further comprising selectively removing at least a portion of the at least one template material.

15. The method of claim 14, wherein the selective removal of at least a portion of the at least one template material results in a shaped structure comprising the first ink material.

16. The method of claim 1, wherein the selective removal of at least a portion of the first ink material results in a structure comprising the at least one template material, wherein the at least one template material has channels, tunnels, internal cavities or voids.

17. The method of claim 16, wherein the selective removal of at least a portion of the first ink material results in a structure comprising the at least one template material having channels, tunnels, internal cavities, or voids that are interconnected in one, two, or three dimensions within the structure.

18. The method of claim 17, wherein at least one channel, tunnel, internal cavity, or void has at least one cross-sectional dimension in a range of from 100 nm to about 10 millimeters.

19. The method of claim 1, wherein the first ink material, the at least one template material, or additives thereof are biocompatible.

20. The method of claim 1, wherein the first ink material, the at least one template material, or additives thereof are suitable for implanting into a mammal.

21. The method of claim 1, wherein the at least one template material is a shear-thinning self-healing supramolecular gel comprising hyaluronic acid functionalized with β-cyclodextrin and hyaluronic acid functionalized with adamantane.

* * * * *

UNITED STATES PATENT AND TRADEMARK OFFICE
CERTIFICATE OF CORRECTION

PATENT NO. : 10,828,399 B2  
APPLICATION NO. : 15/079257  
DATED : November 10, 2020  
INVENTOR(S) : Burdick et al.

Page 1 of 1

It is certified that error appears in the above-identified patent and that said Letters Patent is hereby corrected as shown below:

In the Claims

Under Column No. 36, Claim No. 10, Line No. 47, Replace:
"10. The method of claim 1, wherein said at least one"
With:
--10. The method of claim 1, wherein the at least one--

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*